United States Patent
Hua et al.

(10) Patent No.: US 12,410,234 B2
(45) Date of Patent: Sep. 9, 2025

(54) COMPOSITIONS AND METHODS FOR RETRIEVING TUMOR-RELATED ANTIBODIES AND ANTIGENS

(71) Applicant: THE TRUSTEES OF THE UNIVERSITY OF PENNSYLVANIA, Philadelphia, PA (US)

(72) Inventors: Xianxin Hua, Wynnewood, PA (US); Xin He, Philadelphia, PA (US); Zijie Feng, Philadelphia, PA (US); Donald L. Siegel, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1217 days.

(21) Appl. No.: 17/050,299

(22) PCT Filed: Apr. 26, 2019

(86) PCT No.: PCT/US2019/029333
§ 371 (c)(1),
(2) Date: Oct. 23, 2020

(87) PCT Pub. No.: WO2019/210155
PCT Pub. Date: Oct. 31, 2019

(65) Prior Publication Data
US 2021/0253728 A1   Aug. 19, 2021

Related U.S. Application Data

(60) Provisional application No. 62/663,074, filed on Apr. 26, 2018.

(51) Int. Cl.
*A61K 47/68* (2017.01)
*A61K 40/11* (2025.01)
*A61K 40/31* (2025.01)
*A61K 40/42* (2025.01)
*C07K 14/705* (2006.01)
*C07K 14/725* (2006.01)
*C07K 16/28* (2006.01)
*A61K 38/00* (2006.01)

(52) U.S. Cl.
CPC ........ *C07K 14/70578* (2013.01); *A61K 40/11* (2025.01); *A61K 40/31* (2025.01); *A61K 40/4201* (2025.01); *A61K 40/4224* (2025.01); *A61K 47/68033* (2023.08); *A61K 47/6849* (2017.08); *C07K 14/7051* (2013.01); *C07K 14/70517* (2013.01); *C07K 14/70521* (2013.01); *C07K 16/2896* (2013.01); *A61K 38/00* (2013.01); *C07K 2317/53* (2013.01); *C07K 2317/565* (2013.01); *C07K 2317/569* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 2009/0175846 A1 | 7/2009 | Mi |
| 2009/0304696 A1 | 12/2009 | Lawson |
| 2013/0266551 A1 | 10/2013 | Campana |
| 2016/0053017 A1 | 2/2016 | Orentas |
| 2016/0340406 A1 | 11/2016 | Zhao |
| 2017/0275362 A1 | 9/2017 | Brentjens |
| 2017/0355757 A1 | 12/2017 | Hu |

FOREIGN PATENT DOCUMENTS

| | | |
|---|---|---|
| EP | 2078202 B1 | 3/2017 |
| KR | 20130138802 A | 12/2013 |
| WO | 2010123874 A1 | 10/2010 |
| WO | 2014167126 A2 | 10/2014 |
| WO | 2017153402 A1 | 9/2017 |
| WO | 2017172981 A2 | 10/2017 |

OTHER PUBLICATIONS

Madsen et al., Comput Struct Biotechnol J. Dec. 5, 2023;23:199-211 (Year: 2023).*
European Patent Office Communication pursuant to Article 94(3) EPC issued in App. No. EP19792926, dated Feb. 18, 2022, 16 pages.
Extended European Search Report issued in App. No. EP19792926, dated May 19, 2022, 14 pages.
Haraguchi et al., "CD13 is a therapeutic target in human liver cancer stem cells", J Clin Invest 2010; 120(9):3326-3339.
International Search Report and Written Opinion issued in App. No. PCT/US19/29333, dated Sep. 16, 2019, 6 pages.
Johnson et al., "Cadherin 17 is frequently expressed by sclerosing variant pancreatic neuroendocrine tumour", Histopathology 2015, 66, 225-233.
June, "Adoptive T cell therapy for cancer in the clinic." 2007, J Clin Invest. 117(6):1466-76.

(Continued)

*Primary Examiner* — Daniel C Gamett
(74) *Attorney, Agent, or Firm* — Saul Ewing LLP; Kathryn Doyle; Alireza Behrooz

(57) ABSTRACT

The present invention includes compositions and methods for retrieving tumor-related antibodies and antigens. In one aspect, the invention includes a method for Sequential Tumor-related Antibody and antigen Retrieving (STAR) which directly and efficiently identifies potent antibodies that can specifically bind to tumor-related antigens on the tumor cell surface. In another aspect, the invention includes a CAR comprising a nanobody, a transmembrane domain, and an intracellular domain, wherein the nanobody is retrieved by a STAR method. In another aspect, the invention includes a CAR T system that targets CD13 and treats acute myeloid leukemia. In another aspect, the invention includes a CAR T system and ADC that targets CDH17 and treats NETs and other types of tumors expressing this antigen, with tolerable toxicities.

17 Claims, 44 Drawing Sheets
Specification includes a Sequence Listing.

(56) References Cited

OTHER PUBLICATIONS

Kaneko et al., "A Bispecific Antibody Enhances Cytokine-Induced Killer-Mediated Cytolysis of Autologous Acute Myeloid Leukemia Cells", The American Society of Hematology, 1993, 9 pages.
Lee et al., "Role of cadherin-17 in oncogenesis and potential therapeutic implications in hepatocellular carcinoma", Biochimica et Biophysica Acta XXX 2010 8 pages.
Muyldermans "Nanobodies: Natural Single-Domain Antibodies", Annu. Rev. Biochem. Mar. 2013, 82:17.1-17.23.
Rodgers, et al., "Switch-mediated activation and retargeting of CAR-T cells for B-cell malignancies", roc Nati Acad Sci U S A 113(4), Jan. 2016, E459-68.
Snow et al., "Expression of cadherin 17 in well-differentiated neuroendocrine tumours", Histopathology 2015, 66, 1010-1021.
SubName: Full=Uncharacterized protein, UniProtKB, (Apr.17, 2012), Database accession No. H3G8L5_PHYRM, URL: UniProt, XP055647775 2 pages.
Zhang et al., "IL-4 Inhibits the Biogenesis of an Epigenetically suppressive PIWI-Interacting RNA to Upregulate CD1a Molecules on Monocytes/Dendritic Cells", J Immunol 2016, 196:1591-1603.

* cited by examiner

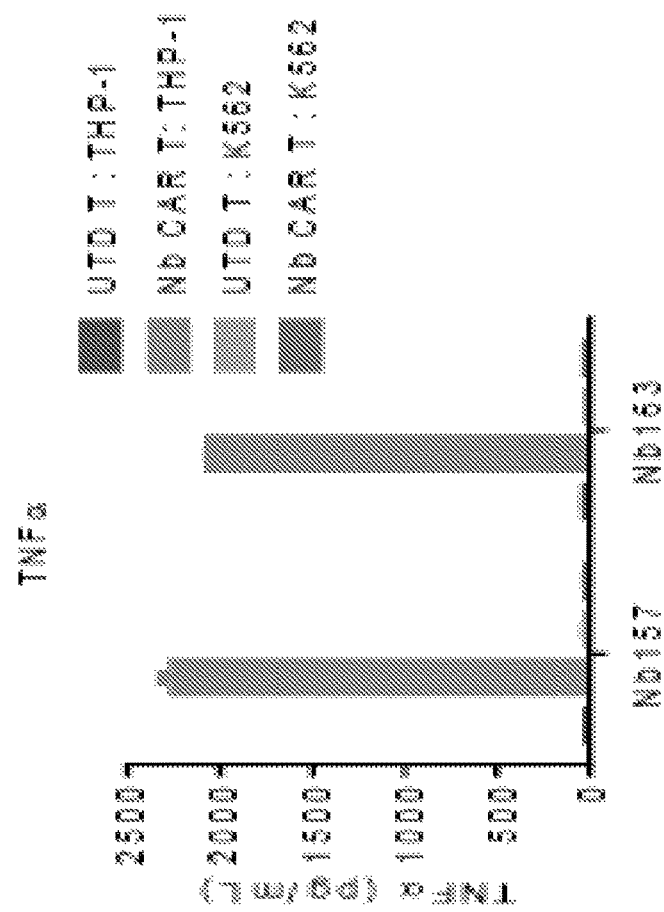
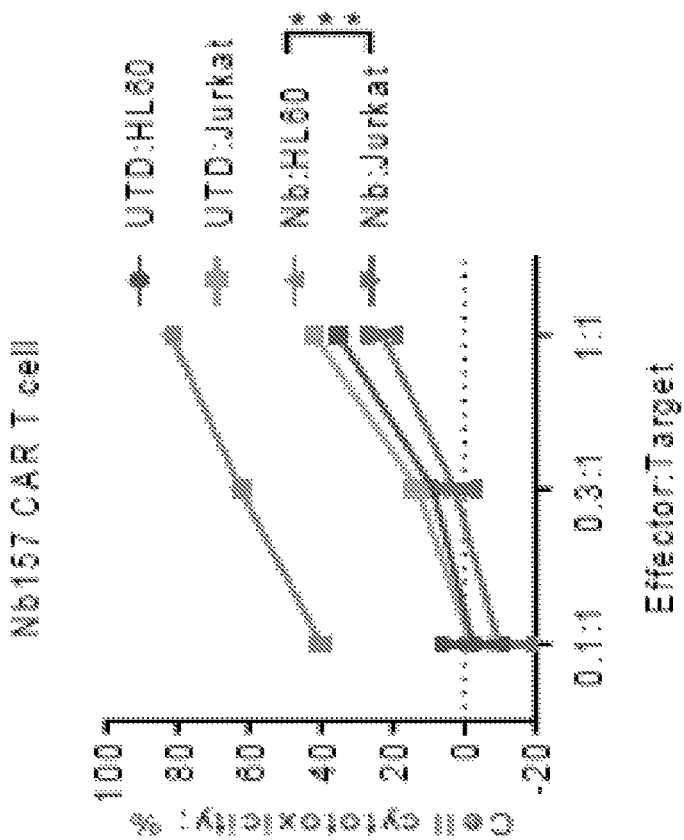
FIG. 2E
FIG. 2D

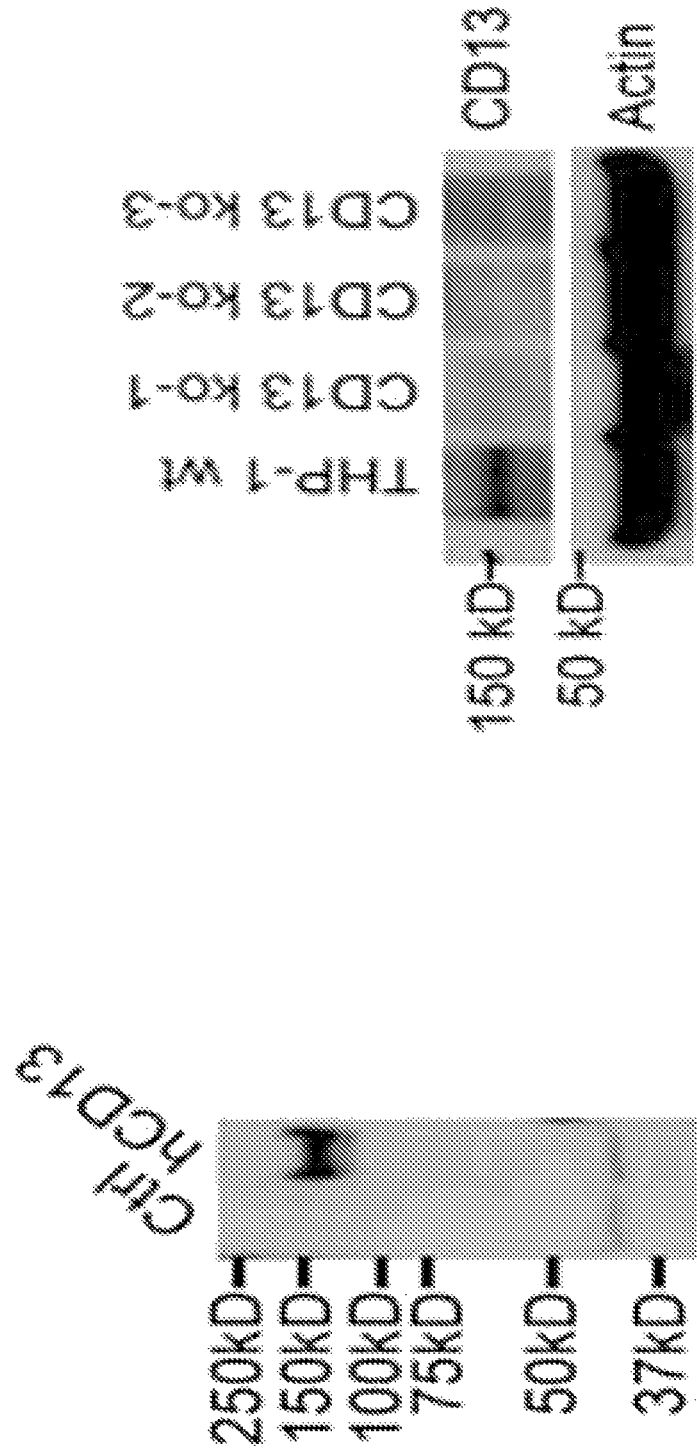

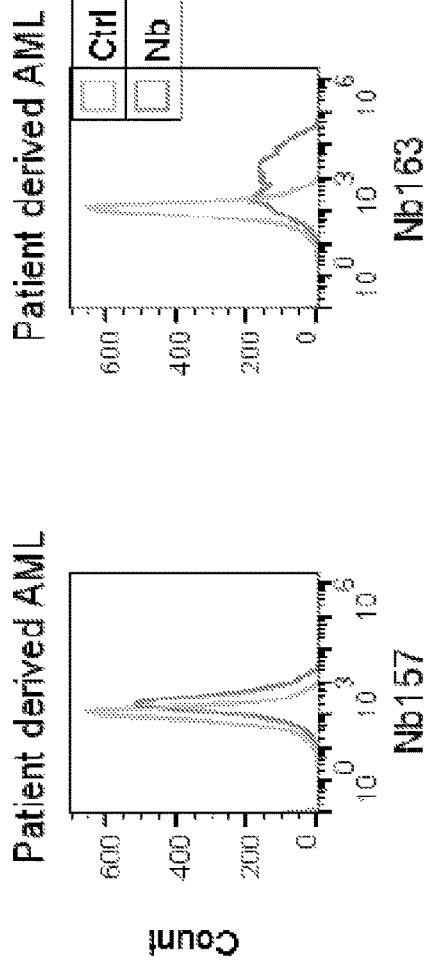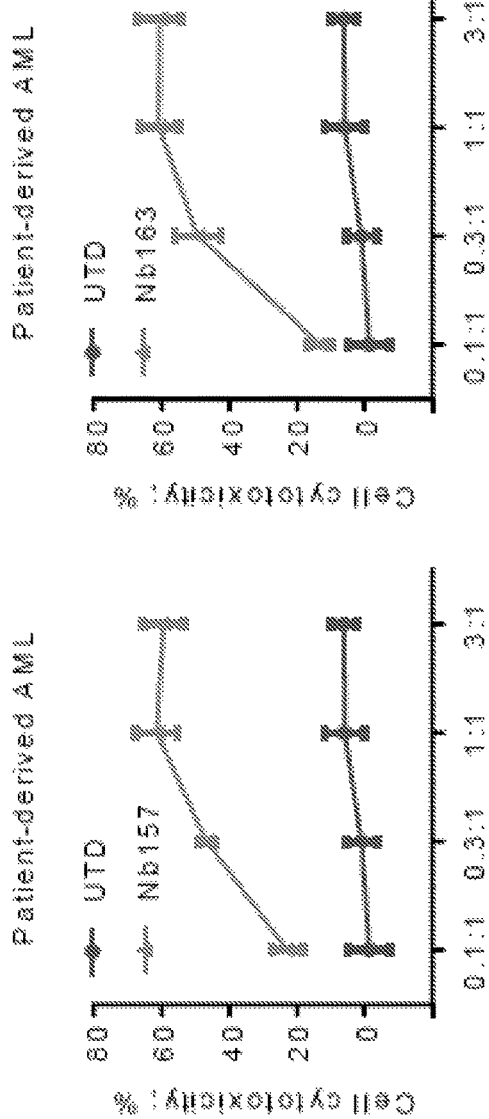
FIG. 5A
FIG. 5B
FIG. 5C
FIG. 5D

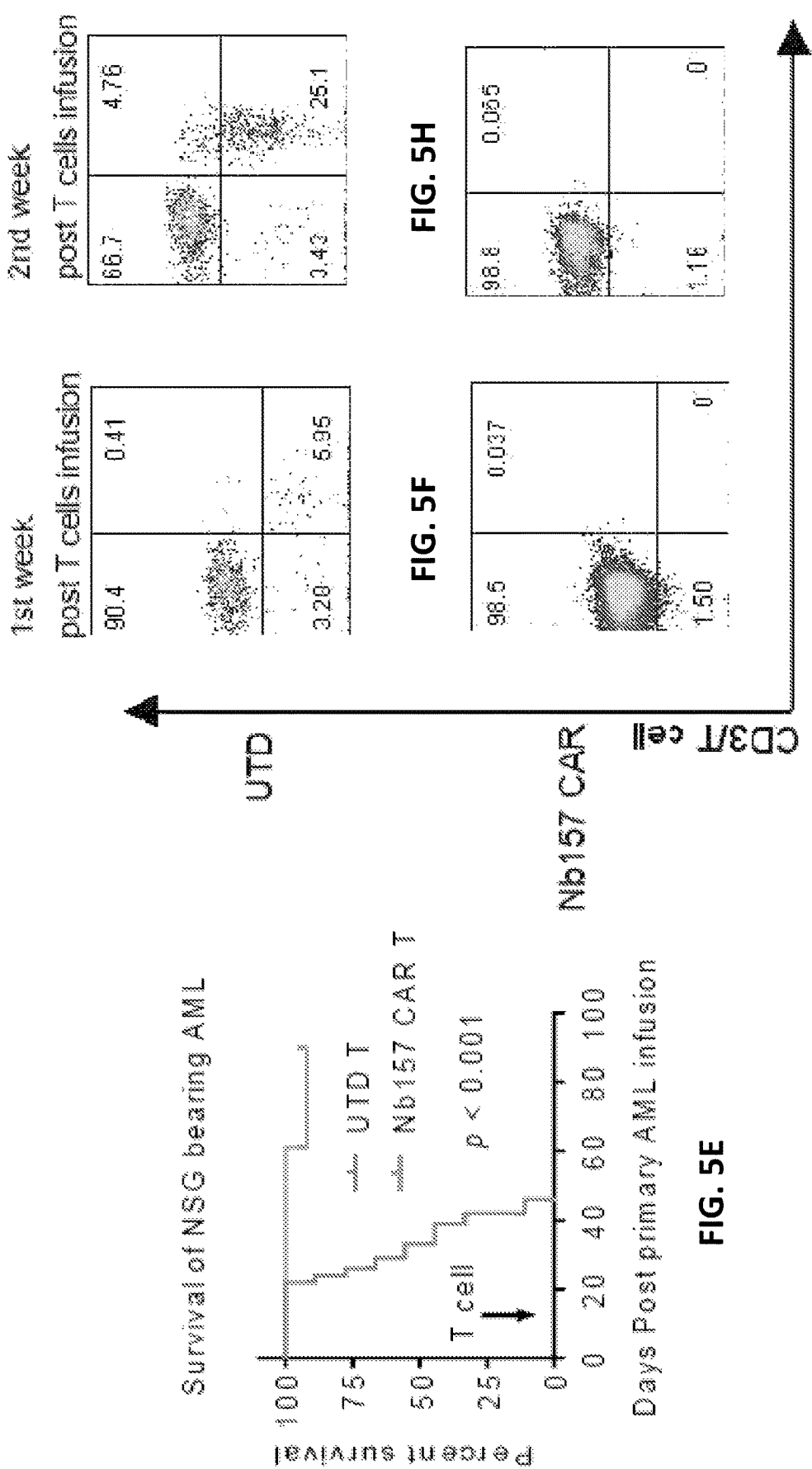

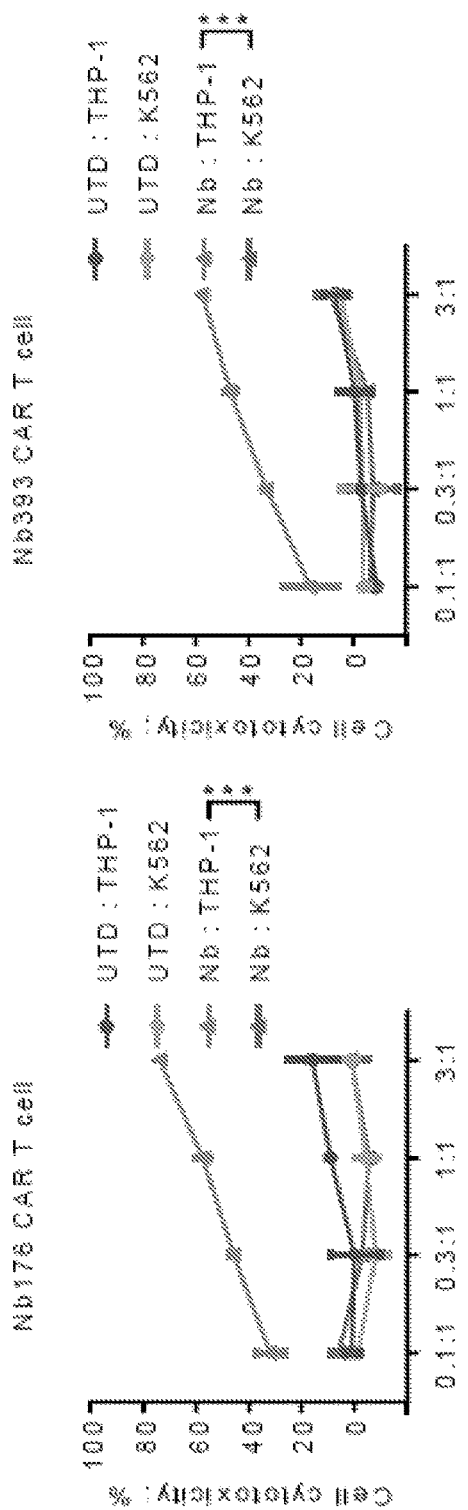
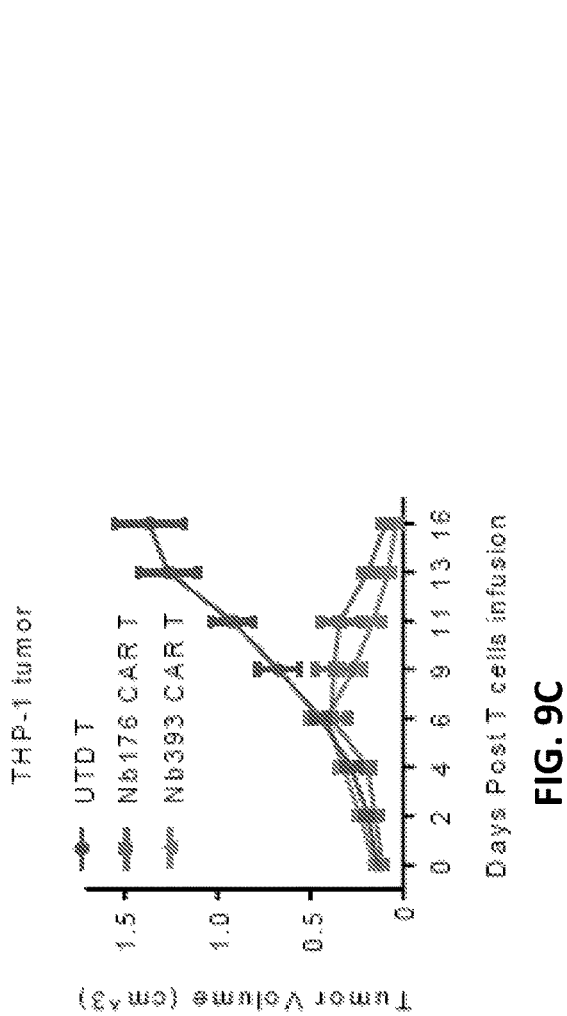
FIG. 9A
FIG. 9B
FIG. 9C

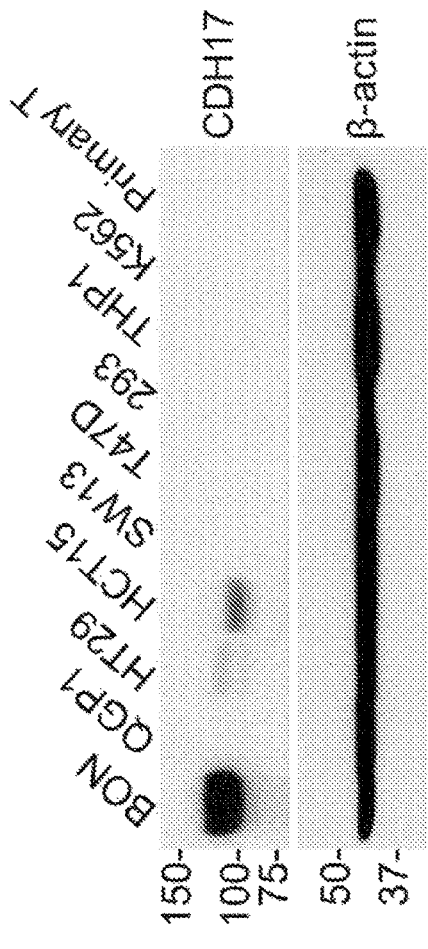
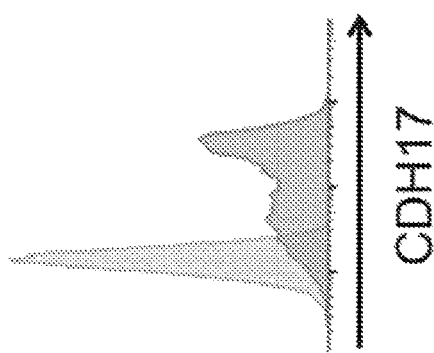
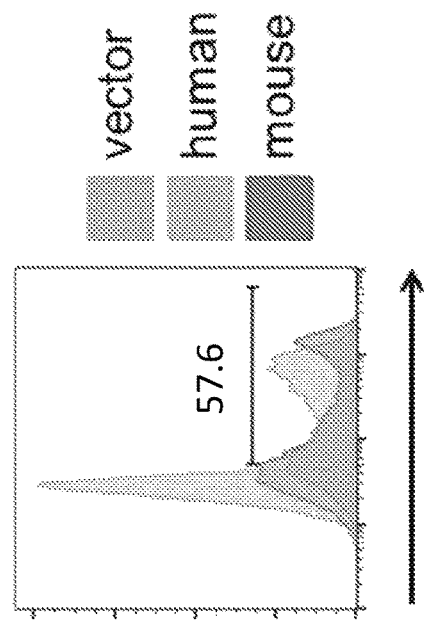
FIG. 12C
FIG. 12D
FIG. 12B

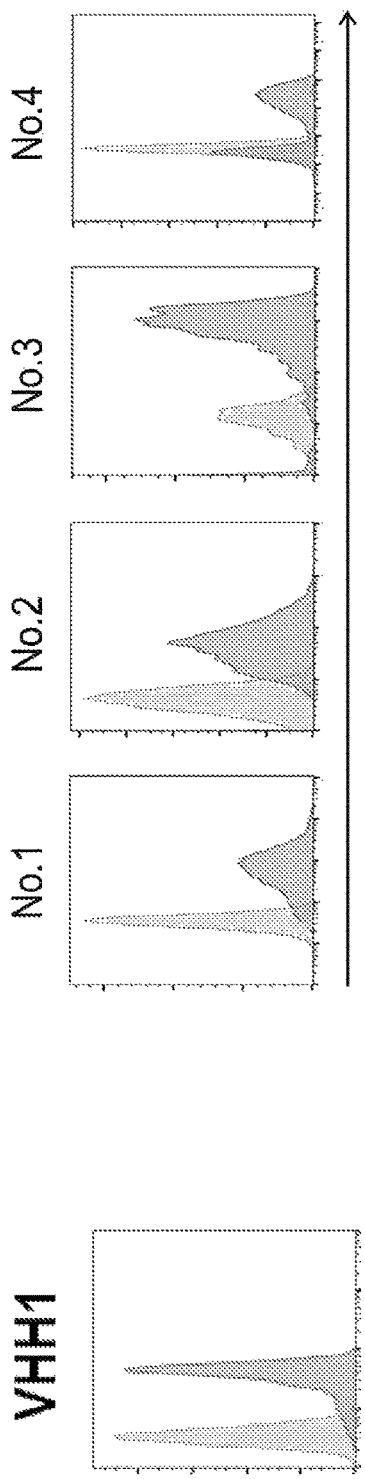
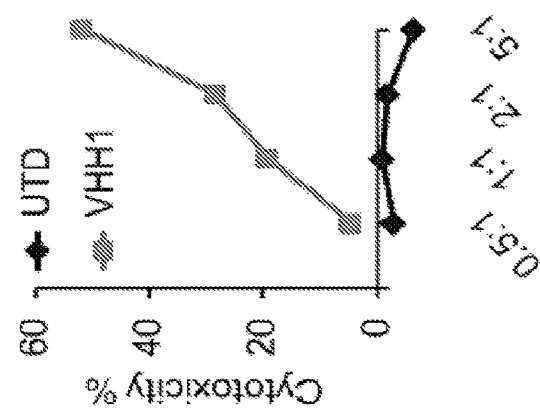
FIG. 13A
FIG. 13B
FIG. 13C
FIG. 13D

DNA seq (SEQ ID NO: 1)

CAGGTGCAGCTGCAGGAGTCTGGGGGAGGATTGGTGCAGCCTGGGGGCTCGGACAAGACT
CTCCTGTGTATCGTCCCCGCACCTTTAGTTATTATGACATGGGCTGGTTCCGCCAGGCTC
CAGGGAAGGAGCGTGAGTTCGTAGCACTGCTTAGTTGGAATGGGGAAAATGCAGAGTAT
TCAGACTCCGTGATGGGCCGTTTCACCGTCTCCCGAGGAATACCCAGAATTCGGTGAA
TCTGCAAATGAACAACCTGAAACCTGAAACCTCGAAGGCAGATCTATTACTGCGCAGTGACGC
ACGGTGGAGCGCGGCCGTTCGTTCCGTTCGGGCCAGGGACCCAGGTCACCGTCTCCTCA

Protein seq (SEQ ID NO: 2)

QVQLQESGGGLVQPGGSTRLSCVSSRTFSYYDMGWFRQAPGKEREFVALLSWNGENAEY
SDSVMGRFTVSRGNTQNSVNLQMNNLKPEDTGIYYCAVTHGGARSVRSWGQGTQVTVSS

▓ Specific amino acids differences between VH and VHH

FIG. 14

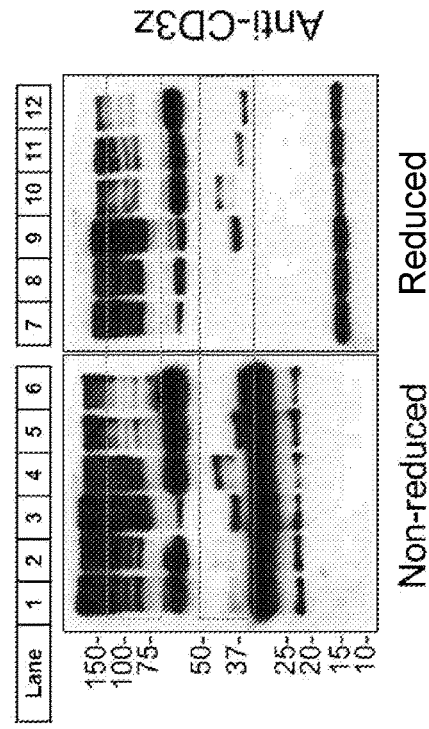
FIG. 17D
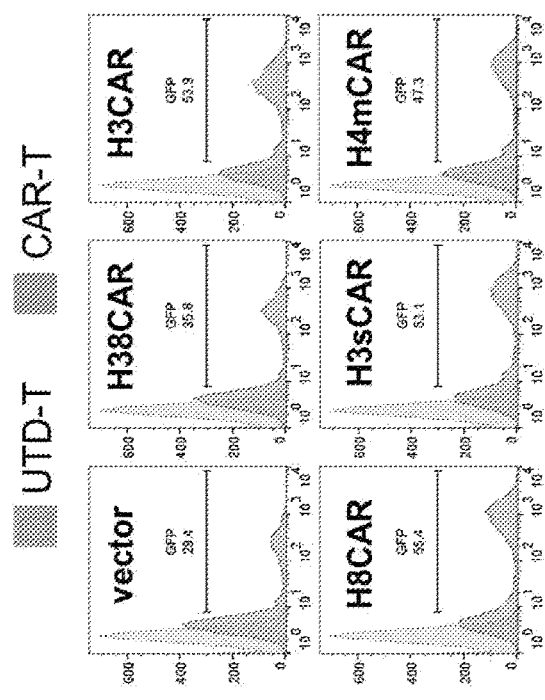
FIG. 17A
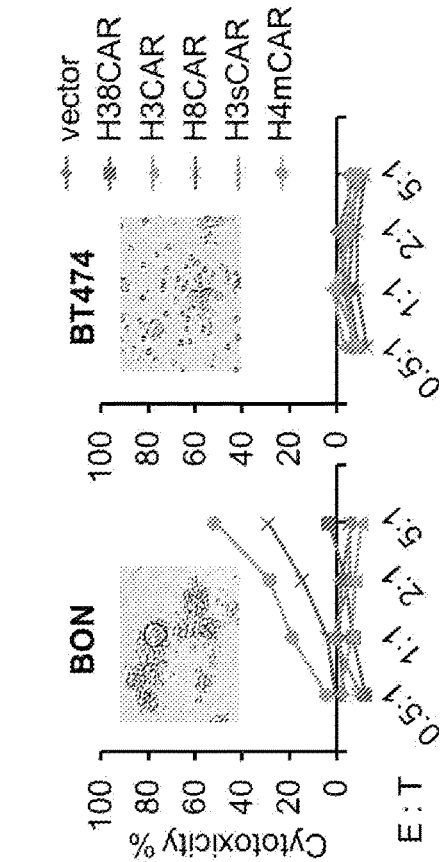
FIG. 17E
FIG. 17B
FIG. 17C

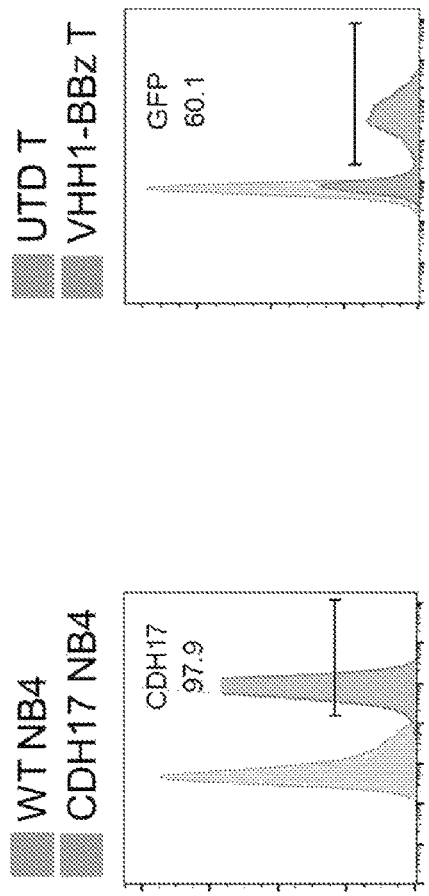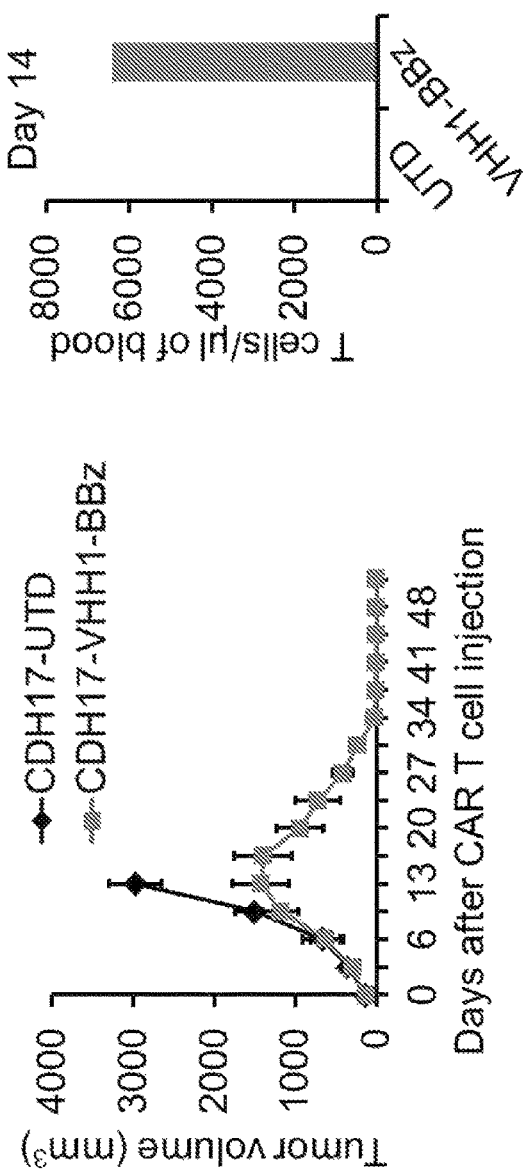
FIG. 18A
FIG. 18B
FIG. 18C
FIG. 18D

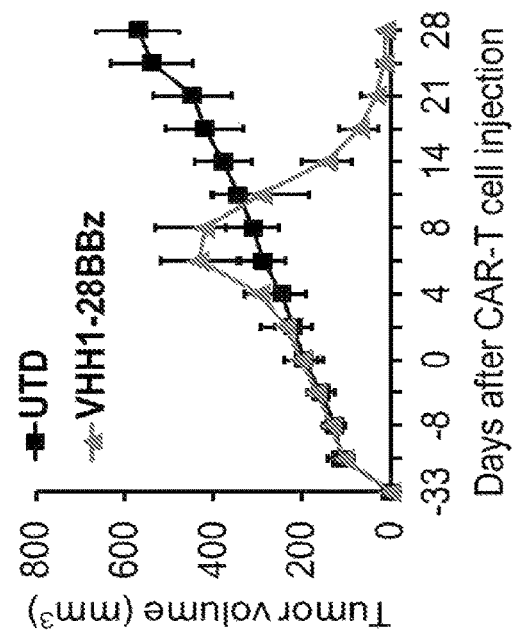
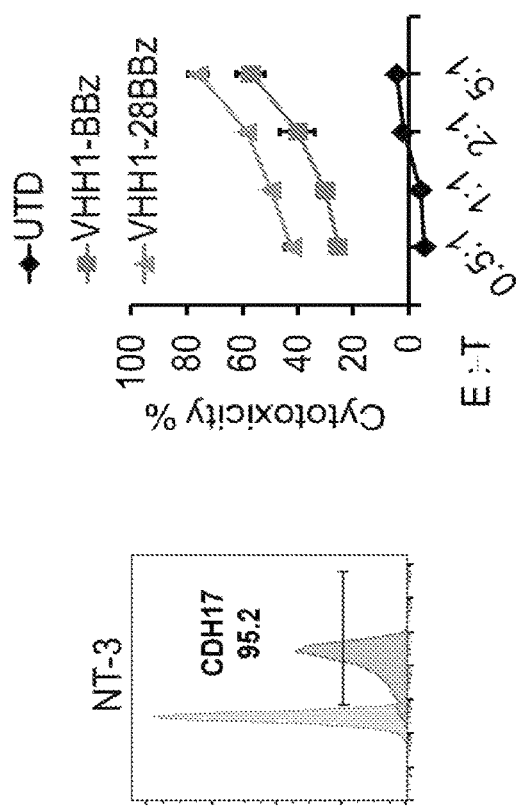
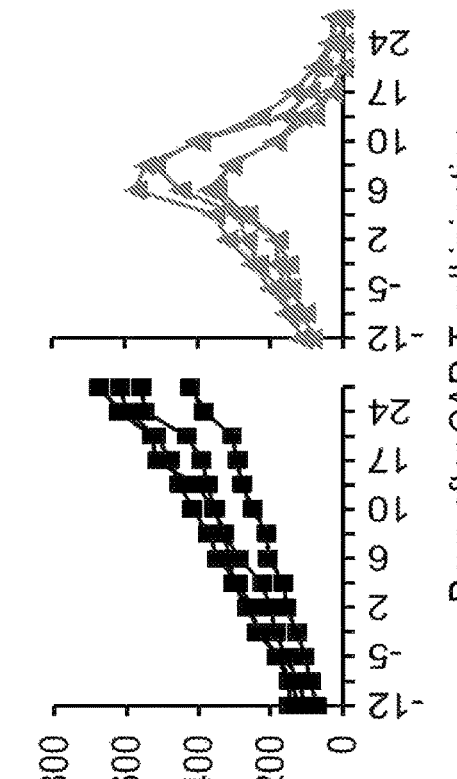
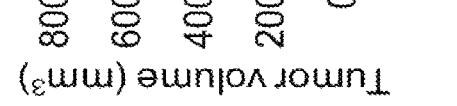
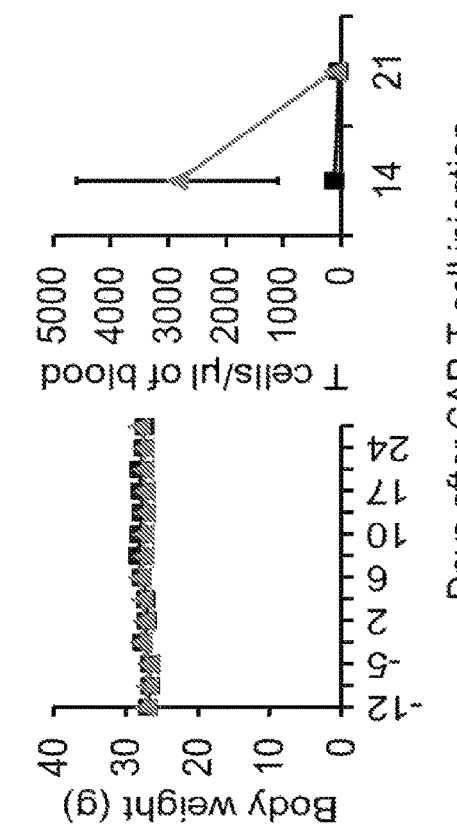
FIG. 20A
FIG. 20B
FIG. 20C
FIG. 20D
FIG. 20E
FIG. 20F

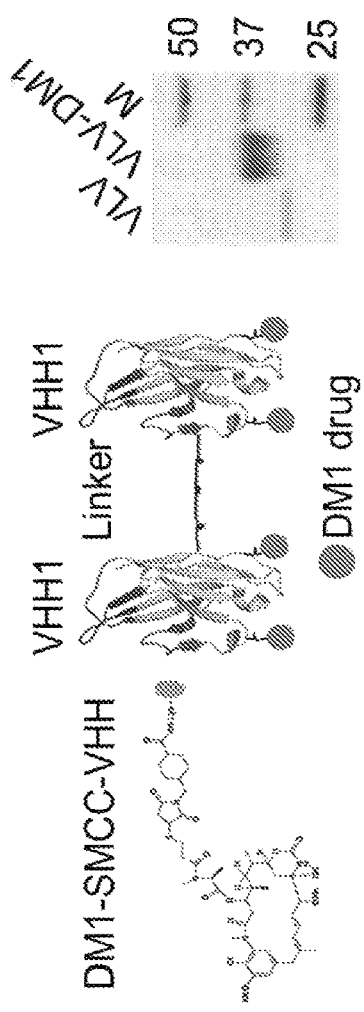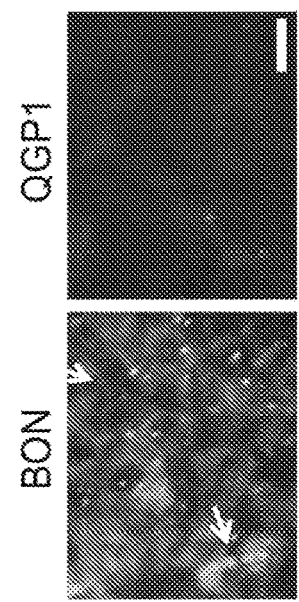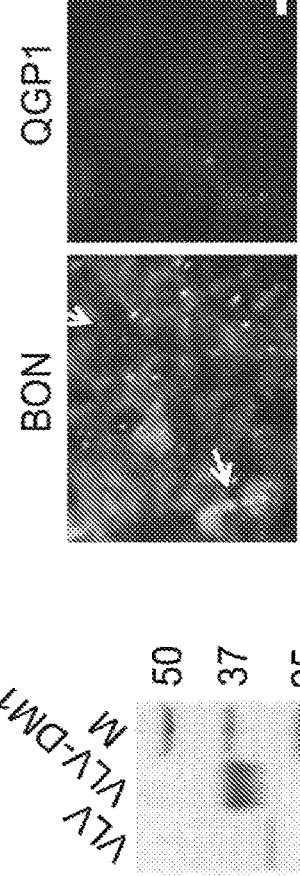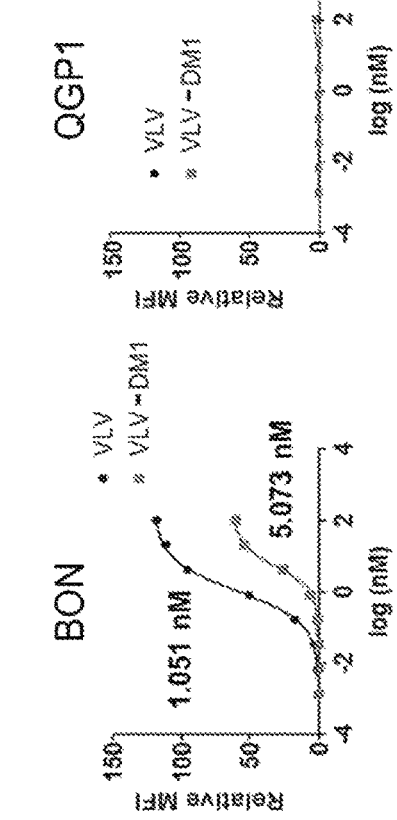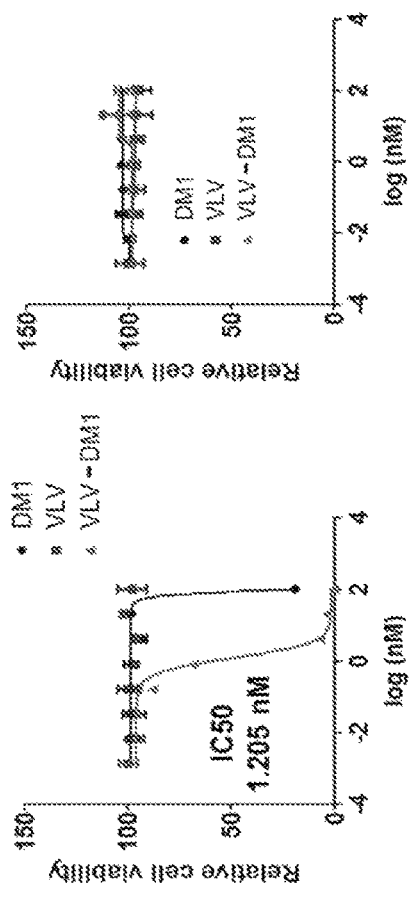
FIG. 21A FIG. 21B FIG. 21C FIG. 21D FIG. 21E FIG. 21F FIG. 21G

COMPOSITIONS AND METHODS FOR RETRIEVING TUMOR-RELATED ANTIBODIES AND ANTIGENS

CROSS-REFERENCE TO RELATED APPLICATIONS

The present application is a 35 U.S.C. § 371 national phase application from, and claims priority to, International Application No. PCT/US2019/029333, filed Apr. 26, 2019, and published under PCT Article 21(2) in English, which is entitled to priority under 35 U.S.C. § 119(e) to U.S. Provisional Application No. 62/663,074 filed Apr. 26, 2018, all of which applications are incorporated herein by reference in their entireties.

STATEMENT REGARDING FEDERALLY SPONSORED RESEARCH OR DEVELOPMENT

This invention was made with government support under CA178856 awarded by the National Institutes of Health. The government has certain rights in the invention.

BACKGROUND OF THE INVENTION

Cancer immunotherapy has made striking progress and changed the course of cancer therapy. Adoptive T cell cancer therapy (ACT) using chimeric antigen receptor (CAR)-expressing T cells can eradicate relapsed or refractory B-cell lymphoma or B-cell lymphocytic leukemia through targeting CD19. The CAR construct has an ectodomain, generally consisting of a single-chain variable fragment (scFv) derived from a monoclonal antibody (mAb), anchored to the cells via a transmembrane domain, followed by the intracellular costimulatory 4-1BB and/or CD28 endomains, and CD3 zeta signaling domain. CAR T cells act like "serial killers" to eliminate the cancer cells. Despite the remarkable success in CAR T therapy targeting the B cell-specific marker CD19, this success has not yet been applied to other types of cancers such as acute myeloid leukemia (AML) and neuroendocrine tumors (NETs). One big hurdle in expanding the CAR T approach to achieve this goal, among other factors such as the repressive microenvironment in solid tumors, is often lack of choices of the mAbs that can both bind the TAAs and enable CAR T cells to eliminate the targeted cancer cells.

The extracellular domain of a cell surface protein with cancer-specific mutations or overexpression could be targeted by CAR T technology. However, besides the difficulties in identifying the remedial marker on tumor cell surface, the availability of mAbs suitable for developing CAR T therapy against many potential targets is very limited. Moreover, many mAbs, when incorporated into the CAR, are not capable of endowing T cells with cytotoxicity, which requires the appropriate engagement between the T cell and target cell to elicit a productive immunological synapse to kill the cancer cells. Furthermore, the high heterogeneity within cancers and high homogeneity between tumors and normal tissues make single antibody/target-based therapy even less impressive. Therefore, it is imperative to effectively generate diverse antibodies that can redirect CAR T cells to specifically kill the cancer cells. Conventional antibodies cannot bind certain antigen surfaces due to the large size of the tetrameric variable heavy chain and light chain (VH and VL) in an antibody, coupled with the possible challenge in generating the optimal scFv. In this regard, the camelid family of animals like llamas can produce heavy chain-only antibodies (VHH), with the small size of 15 kD in the single domain (aka nanobodies or Nbs), that bind various epitopes including small cavities. To expedite the development of CAR T cells targeting tumor cell surface proteins systematically, it is ideal to generate numerous tumor-associated and CAR-compatible mAbs and to identify the recognized antigens, which would both expand the CAR T choices and uncover previously unappreciated cell surface antigens/targets to develop potent cancer immunotherapy. However, such a system remains to be established.

Chemotherapy-resistant Acute Myeloid Leukemia (AML) is highly aggressive with few choices of effective therapy, and thus faces poor prognosis. CAR T cells targeting CD33, a cell surface lectin, and CD123, a subunit of IL3 receptor, were tested for suppressing AML in clinical relevant models, but the clinical application was hindered by the side effects on normal hematopoietic stem cells (HSC) and other normal tissues.

A need exists for methods of isolating potent cancer killing or diagnostic antibodies. More specifically, there is an urgent need to develop potent antibodies against AML-specific and NET-specific surface targets to improve AML and NET therapy without causing devastating side effects. The present invention satisfies these needs.

SUMMARY OF THE INVENTION

In one aspect, the invention includes a chimeric antigen receptor (CAR) comprising a nanobody, a transmembrane domain, and an intracellular signaling domain.

In another aspect, the invention includes a switchable CAR system comprising a nanobody fused to a peptide neoepitope (PNE) molecule and a CAR. The CAR comprises a PNE-specific scFV, a transmembrane domain, and an intracellular signaling domain.

In yet another aspect, the invention includes a modified T cell or precursor thereof, comprising any of the CARs or switchable CAR systems disclosed herein.

In still another aspect, the invention includes a composition comprising an antibody drug conjugate (ADC) comprising a nanobody conjugated to a drug or a toxin or a radioisotope.

Another aspect of the invention includes a method for treating cancer in a subject in need thereof. The method comprises administering to the subject a modified T cell or precursor thereof comprising any of the CARs, or switchable CAR systems, or compositions comprising an ADC disclosed herein.

Yet another aspect of the invention includes a method for generating a plurality of tumor-specific and CAR T cell-compatable nanobodies. The method comprises immunizing a camelid animal with a tumor cell line, isolating PBMCs from the animal, performing phage display, selecting the tumor specific nanobodies, inserting the selected nanobodies into a CAR expressing vector thereby generating a nanobody CAR library, transducing human primary T cells with the nanobody CAR library, injecting the library into an animal and selecting the nanobodies that cause T cell enrichment in the tumor in vivo.

In various embodiments of the above aspects or any other aspect of the invention delineated herein, the nanobody is retrieved by a sequential tumor-related antibody and antigen retrieving (STAR) method.

In certain embodiments, the nanobody specifically binds to CD13. In certain embodiments, the nanobody specifically binds to CDH17. In certain embodiments, the nanobody specifically binds to the first domain of CDH17.

In certain embodiments, the nanobody is selected from the group consisting of VH157, VH163, and VHH1.

In certain embodiments, the nanobody comprises the amino acid sequence sequence of any one of SEQ ID NOs: 2, 19, or 24. In certain embodiments, the nanobody is encoded by the nucleotide sequence of SEQ ID NO: 1. In certain embodiments, the nanobody comprises a CDR1 region comprising the amino acid sequence of any one of SEQ ID NOs: 3, 25, or 28. In certain embodiments, the nanobody comprises a CDR2 region comprising the amino acid sequence of any one of SEQ ID NOs: 4, 26, or 29. In certain embodiments, the nanobody comprises a CDR3 region comprising the amino acid sequence of any one of SEQ ID NOs: 5, 27, or 30.

In certain embodiments, the CAR further comprises a hinge domain selected from the group consisting of a CD8 hinge, an IgG3s hinge, and an IgG4m hinge. In certain embodiments, the hinge domain comprises the amino acid sequence of any one of SEQ ID NOs: 20 or 38.

In certain embodiments, the transmembrane domain is selected from the group consisting of CD8, CD28, and ICOS. In certain embodiments, the transmembrane domain comprises SEQ ID NO: 21.

In certain embodiments, the intracellular signaling domain comprises 4-1BB and CD3 zeta. In certain embodiments, the intracellular signaling domain comprises SEQ ID NO: 22.

In certain embodiments, the CAR comprises the amino acid sequence of any one of SEQ ID NOs: 17, 23, 34 or 36. In certain embodiments, the CAR is encoded by the nucleotide sequence of any one of SEQ ID NOs: 33 or 35.

In certain embodiments, the nanobody is fused to the N-terminal region of the PNE. In certain embodiments, the nanobody is fused to the C-terminal region of the PNE.

In certain embodiments, the drug or toxin or radioisotope is selected from the group consisting of maytansinoid (DM1), SSTR2-binding octreotide, a toxin, paclitaxel, auristatin, MMAE, MMAF, dauxrubicin, duocarmycin A, 5-fluoruracil, methotrexate, tutbulin polymerization inhibitors, ravtansine (DM4), Ricin A, 90Y, 177Lu, and 111In.

In certain embodiments, the ADC comprises nanobody VHH1 conjugated to DM1. In certain embodiments, the ADC comprises a first VHH1 nanobody linked to a second VHH1 nanobody (VLV) conjugated to DM1.

In certain embodiments, the cancer is acute myeloid leukemia (AML). In certain embodiments, the cancer is a neuroendocrine tumor (NET). In certain embodiments, the cancer is colorectal cancer.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIG. 1A: Flow chart of AML specific CAR compatible nanobodies in vivo screening. Llama was immunized with AML cell line THP-1. Nanobody library was generated from the llama PMBC including B cells by molecular cloning. Two rounds of conventional cell-based phage display were applied, which took T-ALL cell line Jurkat or chronic myelogenous leukemia (CML) cell line K-562 as negative absorption, followed by one round of count-selection. The resultant THP-1 specific nanobodies were inserted into a chimeric antigen receptor expressing lenti-vector to generate Nb-CAR library. Human primary T cells were transduced by the Nb-CAR library and injected into THP-1 or K562 borne NSG mice to perform the in vivo selection. Nbs that can adapt T cells to enrich in the tumor were PCR-amplified and sequenced. FIG. 1B: 10 million THP-1 cells or 5 million K562 cells were transplanted into NSG mice subcutaneously, followed by treatment of untransduced (UTD) T cells or Nb-lib-CAR T cells. 2 weeks later, Nbs from tumor infiltrated T cells were isolated and identified by PCR amplification. FIG. 1C: Top 5 frequent Nbs in the THP-1 tumor were listed and tested for their recognition to the THP-1 cells, Jurkat cells, or K-562 cells.

FIGS. 2A-2K are series of a diagram and graphs depicting the finding that all the nanobodies isolated by the STAR system empower CAR T cells to potently kill AML cells in vitro. FIG. 2A: Schematic diagram of Nb CAR structure, including signal peptide (SP), IgG4 mutant (IgG4m) hinge, CD8 transmembrane domain (TM), 4-1BB and CD3zeta domain. FIGS. 2B-2D: Nb CAR showed potent and specific cytotoxicity against THP-1 or HL60 cells in a dose dependent manner, but not to K562 or Jurkat cells. Untransduced (UTD) T cells did not exert obvious killing. (One-way ANOVA: *, p<0.05, , p<0.01,*, p<0.001, ns, p>0.05). FIGS. 2E-2F: THP-1 cells stimulated Nb157 or Nb163 CAR T cells, but not UTD T cells, to release cytokines including TNFα and IFNγ. FIG. 2G: Only THP-1 cells induced the Nb157 or Nb163 CAR T cells to degranulate, i.e. CD107a localization to the cell membrane, after 4 hour co-culture. FIGS. 2H-2K: THP-1 cells potently stimulated the Nb157 or Nb163 CAR T cells to proliferate after 4 days co-culture.

FIGS. 3A-3B: 10 million THP-1 cells were transplanted into NSG mice subcutaneously. The tumor reached 150 mm$^3$ after about 14 days. 3 million Nb157, Nb163 CAR or UTD T cells were injected intravenously into the mice separately. The tumor engraftments were monitored every other day. n=4. Scale bar was 10 mm. FIG. 3C: Hematoxylin and eosin stain of THP-1 xenograft after Nb157, Nb163 CAR or UTD T cells treatment. Scale bar was 100 um. FIG. 3D: 3 million Nb157 CAR or UTD T cells were injected intravenously into NSG mice bearing HL60 tumor separately. The tumor engraftments were monitored every other day. (n=4. One-way ANOVA: ***, p<0.001). FIG. 3E: 5 million K562 cells were transplanted into NSG mice subcutaneously. The tumor reached 150 mm$^3$ after about 10 days. 3 million Nb157, Nb163 CAR or UTD T cells were injected into NSG mice separately. The tumor engraftments were monitored every other day. (n=4. One-way ANOVA: ns, p>0.05). FIG. 3F: 1.5 million Nb157, Nb163 CAR or UTD T cells were injected intravenously into NSG mice bearing THP-1 tumor separately. The tumor engraftments were monitored every other day until the tumors were gone completely. n=4.

FIGS. 4A-4F are series of images and graphs illustrating the identification of CD13 as a target to kill AML cells by CAR T cells. FIG. 4A: Experiment schema: About 3000 cell membrane protein cDNAs were purified and transfected into HEK293T cells separately, followed by flow analysis with the nanobodies expressing phage and FITC-labeled secondary antibody against phage M13 protein. FIG. 4B: Flow analysis of nanobodies binding to the HEK293T cells with CD13 overexpression. FIG. 4C: CD13 cDNA expression confirmed in HEK293T cells by western blot. FIG. 4D: Western blot to confirm the gRNA/CRISPR guided CD13 knockout effect in THP-1 cells. Three independent gRNAs were transduced into THP-1 separately, followed by puromycin selection and single individual clone expansion. FIG. 4E: Flow analysis of Nb157 or Nb163 binding CD13 knockout THP-1 cells. FIG. 4F: Killing assay of Nbs CAR T cells to the THP-1 wild type (wt) or THP-1 cd13-ko.

FIGS. 5A-5K are series of images and graphs depicting that Nb157 CAR T cells exhibit antitumor activity in patient-derived AML cells in a NSG mouse model. FIGS. 5A-5B: Both Nb157 and Nb163 recognized the patient derived AML cells by flow analysis. FIGS. 5C-5D: Both Nb157 and Nb163 CAR T cells specifically killed the patient derived AML cells in vitro in a dose dependent manner. FIG. 5E: Nb157 CAR T cells efficiently prolonged the survival of NSG mice bearing patient derived AML. In brief, 20 million of Patient derived AML cells were injected into NSG mouse, followed by 3 million of Nb157 CAR T cells or UTD T cells treatment. The survival of mice was monitored. Each group n=10. FIGS. 5F-5I: Patient derived AML in NSG bone marrow and spleen were monitored after Nb157 CAR T cell treatment by staining with anti-human CD45/CD3/CD33, followed by flow cytometry analysis. FIGS. 5J-5K: At the end points of each group of experiment, the mice spleens were harvested and fixed by paraformaldehyde, followed by immunofluorescence staining of the anti-human CD3/CD33 and DAPI (Nuclear).

FIGS. 6A-6B: Schematic diagram of switchable CAR T system. The Nb157 was expressed and purified by fusing with PNE, a fourteen amino acid peptide, either at N terminal or C terminal of the Nanobody. Primary human T cells were engineered by lentivirus transduction of scFv CAR that recognized PNE specifically. FIG. 6C: Test the affinity of Nb157, Nb157-N-PNE or Nb157-C-PNE against THP-1 cells by flow cytometry analysis. FIG. 6D: Killing assay of Nb157-PNE-mediated sCAR system against THP-1 cells in series of switch concentrations. The ratio of sCAR T to THP-1 was 2:1 and assay was performed after 16 hours incubation. FIG. 6E: 10 million THP-1 cells were transplanted into NSG mice subcutaneously to form the 150 mm³ of tumors. 5 million sCAR or UTD T cells were injected intravenously into NSG mice separately, followed by treatment of 0.25 mg/kg of Nb-C-PNE protein or PBS every other day. The engraftment volumes were monitored by measuring the lengths and widths of the tumors. FIG. 6F: sCAR potently improved the survival of NSG mice bearing the patient derived AML cells. Each group n=6. FIGS. 6G-6H: 20 million patient derived AML cells were injected into NSG mouse, followed by sCAR T cells treatment 2 weeks after AML infusion. Nb157-PNE or PBS were injected i.v. every other day for 7 weeks. The primary leukemia or CAR T cells in the mouse peripheral blood were monitored by staining with CD33 or CD3 fluorescence labeled antibodies.

FIG. 8A: Western blot with anti-human CD3z to show the Nb CAR expression in primary T cells transduced by the lentivirus. Beta-Mercaptoethanol (BME) is suitable for reducing protein disulfide bonds, to make the dimer protein to monomer. FIG. 8B: Cytometry flow showed GFP expression in primary T cells transduced with Nb CAR lentivirus. FIG. 8C: HL60 cells, not Jurkat cell, stimulated Nb157 CAR T cell to secrete IFN-gamma. Primary T cells were activated and transduced by the Nb157 CAR lentivirus, followed by incubation with HL60 cells or Jurkat cells in different E/T ratios. 16 hour later, IFN-gamma in the supernatant was detected by ELISA.

FIGS. 9A-9G are series of images and graphs showing that Nb176 and Nb393 CAR T cells performed potent suppression against THP-1 tumor in vitro and in vivo. FIGS. 9A-9B: Nb176 and Nb393 CARs showed potent and specific cytotoxicity against THP-1 cells in a dose dependent manner, but not to K562 cells. Untransduced (UTD) T cells do not exert obvious cytotoxicity. FIGS. 9C-9D: 10 million THP-1 cells were transplanted into NSG mice subcutaneously. The tumor reached 150 mm³ after about 14 days. 3 million Nb176, Nb393 CAR or UTD T cells were injected intravenously into NSG mice separately. The tumor engraftments were monitored every other day. Scale bar was 10 mm. FIG. 9E: Hematoxylin and eosin stain of THP-1 xenograft after Nb176, Nb393 CAR or untransduced T cell treatment. Scale bar was 100 um. FIG. 9F: 5 million K562 cells were transplanted into NSG mice subcutaneously. The tumor reached 150 mm³ after about 14 days. 3 million Nb157, Nb163 CAR or UTD T cells were injected intravenously into NSG mice separately. The tumor engraftments were monitored every other day. 9 days after T cells treatment, the K562 tumor tissues were harvested and recorded. Scale bar was 10 mm. FIG. 9G: Hematoxylin and eosin stain of K562 xenograft after Nb157, Nb163 CAR or untransduced T cell treatment. Scale bar was 200 um.

FIGS. 10A-10B: Patient derived AMLs and Nb CAR T cells in mouse peripheral blood were monitored weekly by staining with anti-human CD45/CD33 or CD45/CD3. FIG. 10C: CAR positive T cells in mouse bone marrow and spleen were detected by tracking GFP from the hCD45+/hCD3+/hCD33− subset two weeks after T cells infusion. FIG. 10D: Memory T cells in mouse peripheral blood were detected 3 weeks after T cells infusion. CD45RA-CD62L+ are the central memory T cells, CD45RA-CD62L− are the effector memory T cells. N=3 and Student t test was applied, *, p<0.05.

FIG. 11A: VHH157-N-PNE and VHH157-C-PNE fusion protein were purified from TOP10 through IPTG induction, Ni-chelating affinity and imidazole elution. Elution samples were analyzed by SDS-PAGE and Coomassie blue staining. FIG. 11B: Western blot of primary T cells transduced by sCAR lentivirus or viehcle, with anti-human CD3z. Beta-Mercaptoethanol (BME) which can break the disulfide bonds between proteins, to make dimer protein into monomer. FIG. 11C: sCAR T cells were prepared by transducing primary T cells with lentivirus. PNE peptide was synthesized with FITC to label. sCAR or UTD T cells were incubated with different concentrations of PNE-FITC, followed by flow cytometry analysis. FIG. 11D: 10 million THP-1 cells were transplanted into NSG mice subcutaneously. The tumor reached 150 mm³ after about 14 days. 0.25 mg/kg of VHH157-C-PNE, VHH157-N-PNE or control PBS was administrated into THP-1 tumor bearing NSG mice intravenously every other day. Tumor size was monitored every other day. N=4 and ns was not significant. FIG. 11E: Mice borne patient derived AML were sacrificed 3 weeks after sCAR T with or without Nb157-C-PNE adjuvant and spleens were harvested.

FIGS. 12A-12D are a series of graphs and images depicting isolation of VHH1 from a llama-derived signal domain antibody phage display naive library by panning to BON cells, as described in FIG. 1A. VHH1 was isolated from phage library and specifically bound human neuroendocrine tumor (NET) BON cells in vitro, but not other tumor cells such as breast cancer cells or leukemia cells, by positive or negative pannings, as illustrated in FIG. 1. FIG. 12A shows about 3000 cell surface protein cDNAs were transfected into 293 cells, followed by flow analysis with VHH1. FIG. 12B depicts the antigen of VHH1 is CDH17 (through DNA sequencing individual phage clones that specifically bound BON cells), as identified by screening the transfected cells. Flow analysis of VHH1 binding to CDH17 overexpressed in 293 cells is shown. FIG. 12C shows Western blot analysis of CDH17 protein expression in NET BON cells but not in breast cancer cell line T47D and leukemia cell lines such as THP-1 cells. FIG. 12D shows human and mouse CDH17 cDNAs were transfected into 293 cells, followed by flow analysis with VHH1. The result indicates that VHH1 can bind both human and mouse CDH17 on cell surface.

FIGS. 13A-13D show a series of images and graphs depicting that VHH1 bound to BON cells as well as patient-derived metastatic pancreatic neuroendocrine tumors (PNETs), can direct CAR T cells to kill BON cells in vitro. FIG. 13A: Flow cytometry analysis showed that VHH1 antibody bound BON cells. FIG. 13B shows that CDH17 is highly expressed on the cell surface of tumor cells from PNET patients, using flow cytometry analysis of VHH1 binding to 4 human PNET samples taken via biopsy from liver, indicating CDH17 as a PNET cell surface marker vulnerable to CAR T attack for therapy. FIG. 13C shows a schematic diagram of VHH-CAR structure, consisting of VHH1 sequence (as detailed in FIG. 14), with an optimized linker, IgG4m hinge (as detailed in FIGS. 15-16), CD8 transmembrane domain (TM), 4-1BB and CD3zeta domain. To determine the impact of the VHH1 CAR T cells on killing the target cells, human primary T cells were transduced with either vector CAR or the VHH1-CAR-expressing lentiviruses. Positive VHH1-CAR T cells were determined by flow cytometry analysis of GFP expression, and used to kill BON cells with the LDH release assay. The results showed that the VHH1 CAR Ts, but not untransduced control T cells (UTD), substantially killed the target cells (FIG. 13D).

FIG. 14 depicts the DNA (SEQ ID NO: 1) and protein (SEQ ID NO: 2) sequences of the VHH1 nanobody. CDR domains of VHH1 are shown in the boxes (SEQ ID NOs: 3-5). Specific amino acid differences between VH and VHH are underlined.

FIG. 15A is a schematic of VHH1-CAR structures with different lengths of hinges. The VHH1-CAR includes different hinge lengths, CD8 transmembrane domain (TM), 4-1BB and CD3zeta domain, followed by IRES-GFP as a marker to demonstrate the percentage of cells expressing the CAR. FIG. 15B shows JRT3 cells were transduced with either vector CAR or the VHH1-CAR lentiviruses with different hinge lengths. Positive VHH1-CAR JRT3 cells were determined by flow cytometry analysis of GFP expression.

FIGS. 16A and 16C show flow cytometry analysis of VHH1 specifically bound to BON cells (FIG. 16A), but not BT474 breast cancer cells (FIG. 16C). FIGS. 16B and 16D show VHH1-CAR JRT3 cells with short hinge specifically killed BON cells (FIG. 16B), but not BT474 cells (FIG. 16D), using LDH release assay. FIG. 16E shows Western blot detection of VHH1-CAR expression in JRT3 cells with anti-human CD3zeta. Ponceau S (PS) was used as an endogenous control. Reduced monomer was shown in the red box. Non-reduced dimer was shown in the black box. FIG. 16F shows a summary of killing efficacy of VHH1-CAR JRT3 cells with different hinge lengths on BON cells.

FIGS. 17A-17E are series of images and graphs depicting human primary VHH1-CAR T cells with an IgG4m hinge killed BON cells most effectively. FIG. 17A shows results from human primary T cells transduced with either vector CAR or the different length hinge VHH1-CAR lentiviruses. Positive VHH1-CAR T cells were determined by flow cytometry analysis of GFP expression. FIGS. 17B-17C show VHH1-CAR T cells with CD8 or IgG4m hinges specifically killed BON cells (FIG. 17B), but not BT474 cells (FIG. 17C), measured using LDH release assay. Microscopic observation of T cell aggregates around Bon cells (FIG. 17B), but not BT474 cells (FIG. 17C). FIG. 17D shows Western blot detection of VHH1-CAR expression in primary T cells with anti-human CD3zeta. Reduced monomer is shown in the grey box. Non-reduced dimer is shown in the black box. FIG. 17E shows a summary of killing efficacy of VHH1-CAR T cells with different hinge lengths on BON cells.

FIGS. 18A-18D show a series of graphs depicting CDH17CAR T cells eliminated CDH17-expressed NB4 tumors in vivo. FIG. 18A shows flow analysis of VHH1 binding to WT or sorted ectopic CDH17 expressing NB4 cells. FIG. 18B shows results from human primary T cells transduced with or without VHH1-CAR lentiviruses. Positive VHH1-CAR T cells were determined by flow cytometry analysis of GFP expression. FIG. 18C shows results from NSG mice with CDH17-NB4 xenograft treated with either UTD or VHH1-BBz CAR-T cells with injection of the T cells 5 times at day, 0, 3, 7, 22 and 24, 10-18 million VHH1-BBz CAR-T cells each time. FIG. 18D shows T cell numbers per ul in peripheral blood of NSG mice with CDH17-NB4 xenograft treated with either UTD or VHH1-BBz CAR-T cells as determined by flow cytometry at Day 14 after CAR T cell injection. These results indicate the CDH17CAR T cells specifically regressed the tumor in CDH17-dependent manner.

FIG. 19A shows flow analysis of VHH1 binding to WT or sorted ectopic CDH17 expressing SKOV3 cells. FIG. 19B shows results from human primary T cells transduced with or without VHH1-CAR lentiviruses. Two types of CDH17 (or VHH1) CARs were generated: VHH1-BBZ is a second generation of CAR including 41-BB and CD3 zeta intracellular domains (FIG. 19B, left), and VHH1-28BBz is a third generation CAR comprising the intracellular CD28, 41-BB and CD3 zeta domains (FIG. 19B, right). Positive VHH1-CAR T cells were determined by flow cytometry analysis, using a rabbit anti-VHH antibody. FIG. 19C shows results from NSG mice with WT or CDH17-SKOV3 xenograft treated with UTD, VHH1-BBz or VHH1-28BBz CAR-T cells two times at day 0 and 5, 10-12 million CAR T cells each time, indicating that the third generation CDH17 CAR is potent to regress the tumor xenogrant, but the $2^{nd}$ generation of CDH17 CAR T cells only suppressed the growth of the tumor in vivo. FIG. 19D shows T cell numbers (per ul) in peripheral blood of NSG mice with WT or CDH17-SKOV3 xenograft treated with UTD, VHH1-BBz or VHH1-28BBz CAR-T cells, as determined by flow cytometry at Day 21 after CAR T cell injection. The results indicate that the 3$^{rd}$ generation of CDH17 CAR Ts produced a higher number of CAR T cells in peripheral blood.

FIGS. 20A-20F are series of graphs depicting that CDH17CAR T cells eliminate NET NT-3 tumors in vivo. FIG. 20A shows flow analysis of VHH1 binding to NT-3 cells, a bona fide human NET cell line showing characteristic expression of somatostatin receptor 2 (SSTR2), chromagranin A, and insulin. FIG. 20B illustrates that CDH17CAR T cells potently kill NT-3 cells in vitro, as determined by an LDH release assay. FIG. 20C shows results from NSG mice with NT-3 xenograft treated with either UTD or VHH1-28BBz CAR-T cells two times at day, 0 and 5, 10-12 million CAR T cells each time. FIG. 20D shows body weights of treated NSG mice, and no reduction of body weight following the CAR T injection, indicating no obvious toxicities to the mice. FIG. 20E shows T cell numbers in peripheral blood of NSG mice with NT-3 xenograft treated with either UTD or VHH1-28BBz CAR-T cells, and the T cell numbers were determined by flow cytometry at Day 14 and 21 after CAR T cell injection. FIG. 20F shows tumor growth of each NSG mouse with NT-3 xenograft treated with either UTD or VHH1-28BBz CAR-T cells. This series of studies indicate that the CDH17 CARs are capable of and potent in killing and eradicating NETs in vivo and CDH17 serves as valuable target for NETs and other CDH17-expressing tumors. Further, as the CDH17 CAR Ts did not cause toxicities in mice, these findings indicate that CDH17 serves as an effective and safer target for immunotherapy against NETs and other tumors expressing CDH17.

FIGS. 21A-21H are series of graphs and images depicting that a VHH1-ADC drug specifically kills BON cells in vitro using MTT assay. FIG. 21A shows the design of VHH1-linker-VHH1 (VLV) DM1 ADC drug. FIG. 21B shows analysis of DM1 conjugated VLV by SDS-PAGE and Coomassie blue staining. FIG. 21C shows internalization of VLV-FITC into BON or QGP1 cells, under a fluorescent microscope. Scale bar: 10 μM. FIGS. 21D and 21E show flow cytometry analysis of unconjugated VLV or VLV-DM1 binding to BON (FIG. 21D) or QGP1 (FIG. 21E) cells, indicating the VLV-DM1 ADC can specifically kill CDH17-expressing BON cells, but not CDH17-negative QGP-1 cells. FIGS. 21F and 21G show in vitro killing by free DM1, unconjugated VLV or VLV-DM1 of BON (FIG. 21F) or QGP1 (FIG. 21G) cells, demonstrating the potent killing of BON cells, but not QGP1 cells (CDH17-negative), by VLV-DM1 ADC (but not the control VLV (IC50+1.2 nM)). FIG. 21H shows microscopic observation of lysed BON cells by VLV-DM1 treatment at 4 nM. Scale bar: 10 μM. Collectively, this series of experiments indicate that CDH17 targeting VHH1-DM1 ADC can potently and specifically kill NET cells.

FIG. 22A is a schema showing human CDH17 truncations. FIG. 22B shows WT CDH17 or CDH17 truncations were transfected into 293 cells, followed by flow analysis with VHH1. FIG. 22C is a schematic diagram of CDH17 structure showing VHH1 binds to the N-terminal EC1 domain of CDH17. These studies demonstrate that VHH1 directly binds CDH17 via an extracellular domain.

DETAILED DESCRIPTION

Definitions

Figure 1A:
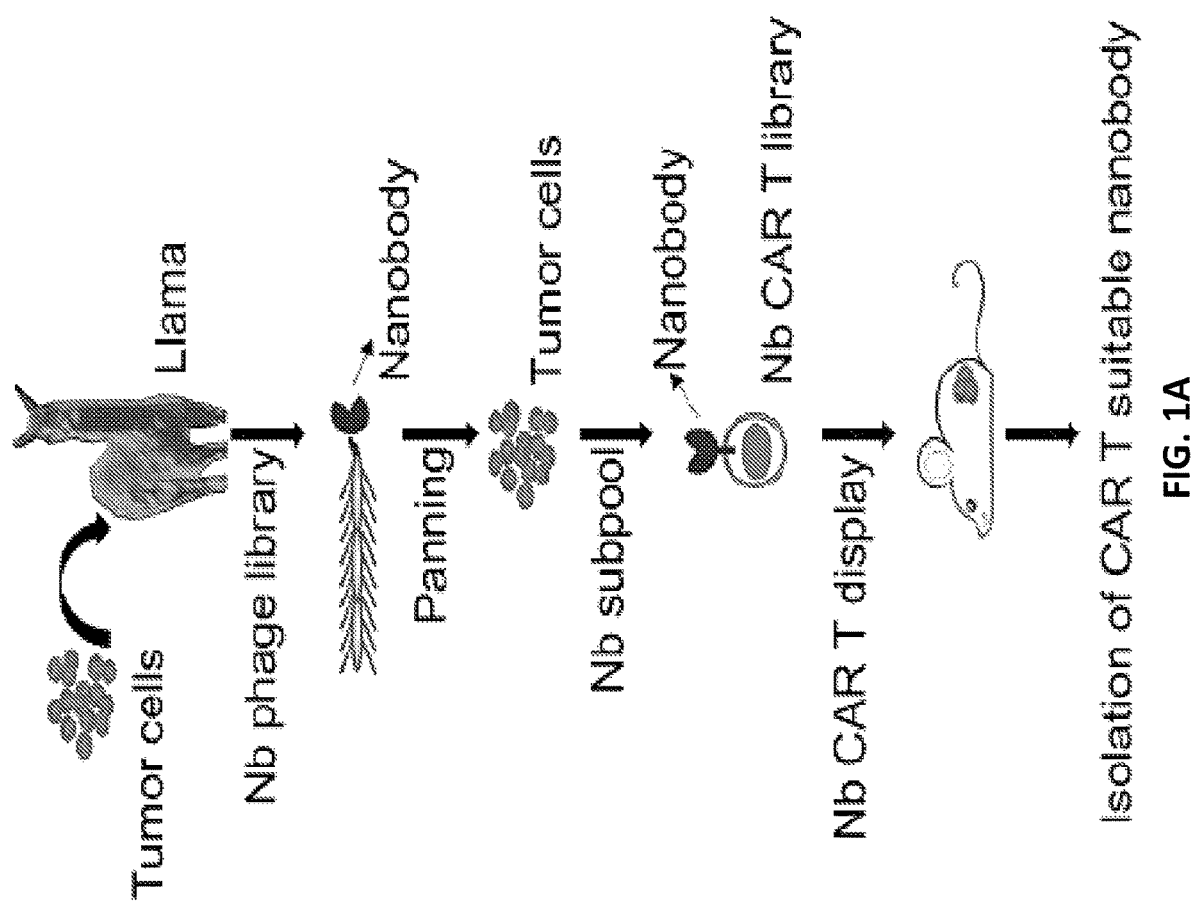
FIGS. 1A-1C are series of images and graphs depicting the steps for generating nanobodies that both differentially bind tumor cells and empower CAR T cells to kill the tumor cells.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

"Allogeneic" refers to a graft derived from a different animal of the same species.

"Alloantigen" refers to an antigen present only in some individuals of a species and capable of inducing the production of an alloantibody by individuals which lack it.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CAR has specificity to a selected target, for example a tumor antigen. CARs may also comprise an intracellular activation domain, a transmembrane domain and an extracellular domain comprising an antigen binding region.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

The term "immunostimulatory" is used herein to refer to increasing overall immune response.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Octretotide" is an octapeptide that mimics natural somatostatin. It is a long-acting analog of somatostatin. It is sold under the brand name Sandostatin (Novartis Pharmaceuticals). d-Phe-Cys-Phe-d-Trp-Lys-Thr-Cys-Thr-ol "Parenteral" administration of an immunogenic composition includes, e.g., subcutaneous (s.c., intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

As used herein, a switchable CAR (sCAR) refers to a CAR comprising a Peptide-Neo-Epitope (PNE) binding domain, a transmembrane domain, and an intracellular signaling domain.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (a) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

"Xenogeneic" refers to any material derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes compositions and methods for retrieveing tumor-related antibodies and antigens.

In one aspect, the invention includes a method for Sequential Tumor-related Antibody and antigen Retrieving (STAR) which directly and efficiently identifies potent antibodies that can specifically bind to tumor-related antigens on the tumor cell surface. In another aspect, the invention includes a method for generating STAR-selected antibodies chimeric antigen receptor (CAR) T cells that specifically target tumor cell antigens. In another aspect, the invention includes a CAR comprising a nanobody, a transmembrane domain, an intracellular signaling domain. In certain embodiments, the nanobody is retrieved by a STAR method. In yet another aspect, the invention includes compositions and methods for treating acute myeloid leukemia (AML) or neuroendocrine tumors (NETs).

Chimeric Antigen Receptor

Certain embodiments of the invention include chimeric antigen receptors (CARs) comprising the following components: An antigen binding domain, a transmembrane domain, a hinge domain, and an intracellular signaling domain.

a) Antigen Binding Domain

In one embodiment, the CAR of the invention comprises an antigen binding domain that is a variable domain heavy-chain camelid antibody (VHH), also referred to as a nanobody. In another embodiment, the CAR comprises an antigen binding domain that binds to Peptide-Neo-Epitope (PNE). The choice of antigen binding domain depends upon the type and number of antigens that are present on the surface of a target cell. For example, the antigen binding domain may be chosen to recognize an antigen that acts as a cell surface marker on a target cell associated with a particular disease state.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof.

In some instances, the antigen binding domain may be derived from the same species in which the CAR will ultimately be used. For example, for use in humans, the antigen binding domain of the CAR may comprise a human antibody as described elsewhere herein, or a fragment thereof.

The antigen binding domain may be operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

The antigen binding domains described herein can be combined with any of the transmembrane domains described herein, any of the intracellular domains or cytoplasmic domains described herein, or any of the other domains described herein that may be included in the CAR.

In certain embodiments, the antigen binding domain (e.g. nanobody) is encoded by the nucleotide sequence of SEQ ID NO: 1. In certain embodiments, the antigen binding domain comprises the amino acid sequence of SEQ ID NO: 2. In certain embodiments, the antigen binding domain comprises a CDR1 sequence comprising the amino acid sequence YYDMG (SEQ ID NO: 3). In certain embodiments, the antigen binding domain comprises a CDR2 sequence comprising the amino acid sequence LLSWNGENAEY-SDSVMGR (SEQ ID NO: 4). In certain embodiments, the antigen binding domain comprises a CDR3 sequence comprising the amino acid sequence AVTHGGARSVRS (SEQ ID NO: 5).

In certain embodiments, the antigen binding domain comprises the amino acid sequence of SEQ ID NO: 19. In certain embodiments, the antigen binding domain comprises a CDR1 sequence comprising the amino acid sequence of SEQ ID NO: 25. In certain embodiments, the antigen binding domain comprises a CDR2 sequence comprising the amino acid sequence of SEQ ID NO: 26. In certain embodiments, the antigen binding domain comprises a CDR3 sequence comprising the amino acid sequence of SEQ ID NO: 27.

In certain embodiments, the antigen binding domain comprises the amino acid sequence of SEQ ID NO: 23. In certain embodiments, the antigen binding domain comprises a CDR1 sequence comprising the amino acid sequence of SEQ ID NO: 28. In certain embodiments, the antigen binding domain comprises a CDR2 sequence comprising the amino acid sequence of SEQ ID NO: 29. In certain embodiments, the antigen binding domain comprises a CDR3 sequence comprising the amino acid sequence of SEQ ID NO: 30.

Tolerable variations of the antigen binding domain (e.g. nanobody) will be known to those of skill in the art, while maintaining specific binding to the antigen. For example, in some embodiments the antigen binding domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 2-4, 19, 23, and 25-30. In some embodiments the antigen binding domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 1.

b) Transmembrane Domain

With respect to the transmembrane domain, the CAR is designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, ICOS, CD3 epsilon, CD45, CD4, CD5, CD8, CD9, CD16, CD22, CD33, CD37, CD64, CD80, CD86, CD134, CD137, CD154, Toll-like receptor 1 (TLR1), TLR2, TLR3, TLR4, TLR5, TLR6, TLR7, TLR8, and TLR9.

The transmembrane domains described herein be combined with any of the antigen binding domains described herein, any of the intracellular domains or cytoplasmic domains described herein, or any of the other domains described herein that may be included in the CAR.

In some instances, a variety of hinges can be employed as well including but not limited to the Ig (immunoglobulin) hinge, and the CD8 hinge. The transmembrane domain may be combined with any hinge domain and/or may comprise one or more transmembrane domains described herein. In one embodiment, the transmembrane domain comprises a CD8 transmembrane domain. In another embodiment, the transmembrane domain comprises a CD8 hinge domain and a CD8 transmembrane domain. In certain embodiments, the hinge domain is selected from the group consisiting of a CD8 hinge, an IgG3s hinge, and an IgG4m hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

c) Intracellular Signaling Domain

The intracellular signaling domain or otherwise the cytoplasmic domain of the CAR is responsible for activation of the cell in which the CAR is expressed. Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

The intracellular signaling domain of the chimeric membrane protein is responsible for activation of at least one of effector functions of the T cell. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

In one embodiment, the intracellular signaling domain of the CAR includes any portion of one or more co-stimulatory molecules, such as at least one signaling domain from CD3, CD8, CD27, CD28, ICOS, 4-IBB, PD-1, any derivative or variant thereof, any synthetic sequence thereof that has the same functional capability, and any combination thereof.

Examples of the intracellular signaling domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fcgamma R11a, DAP10, DAP 12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD 160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD 103, ITGAL, CD 11 a, LFA-1, ITGAM, CD lib, ITGAX, CD 11c, ITGB1, CD29, ITGB2, CD 18, LFA-1, ITGB7, TNFR2, TRANCE/RANKL, DNAM1 (CD226), SLAMF4 (CD244, 2B4), CD84, CD 96 (Tactile), CEACAM1, CRT AM, Ly9

(CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

In certain embodiments, the intracellular signaling domain of the CAR comprises 4-1BB and CD3 zeta.

The intracellular signaling domains described herein can be combined with any of the antigen binding domains described herein, any of the transmembrane domains described herein, or any of the other domains described herein that may be included in the CAR.

In certain embodiments, the CAR comprises a signal peptide, an IgG4 mutant (IgG4m) hinge region, a CD8 transmembrane domain (TM), a 4-1BB intracellular domain and CD3zeta intracellular domain.

In certain embodiments, the CAR comprises the amino acid sequence of any one of SEQ ID NOs: 17, 23, 34 or 36. In certain embodiments, the CAR is encoded by the nucleotide sequence of any one of SEQ ID NOs: 33 or 35. Tolerable variations of the CAR sequences will be known to those of skill in the art. For example, in some embodiments the CAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 17, 23, 34 or 36. In some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 33 or 35.

As used herein, a switchable CAR (sCAR) refers to a CAR comprising a Peptide-Neo-Epitope (PNE) binding domain, a transmembrane domain, and an intracellular signaling domain. The switchable CAR can be used in conjunction with a molecule comprising a nanobody fused to a PNE molecule (e.g. a switchable CAR system). When the nanobody-PNE molecule comes into contact with the sCAR, the "switch" is turned on and the CAR T cell is activated.

The nanoboby can be fused to the C-terminal region of the PNE or the N-terminal region of the PNE. In certain embodiments, nanobody Nb157 (VHH157) is fused to the C-terminal region of PNE. In certain embodiments, nanobody Nb157 is fused to the N-terminal region of PNE. In certain embodiments, nanobody Nb163 (VHH163) is fused to the C-terminal region of PNE. In certain embodiments, nanobody Nb163 is fused to the N-terminal region of PNE.

Included in the invention are isolated polypeptides comprising CARs, isolated nucleic acids comprising CARs, vectors comprising nucleic acids comprising CARs, and modified cells (e.g.T cells) comprising CARs, nucleic acids encoding CARs, or vectors comprising CARs.

Methods of Treatment

The modified cells (e.g., CAR T cells, or cells comprising a switchable CAR system) described herein, may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells. In certain embodiments, the disease to be treated is cancer.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, acute myeloid leukemia, chronic myeloid leukemia, pancreatic neuroendocrine tumor (PNETs), gastrointestinal NETs, and lung and prostate cancer NETs, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor. In one embodiment, the cancer is ovarian cancer. In one embodiment, the cancer is endometrial cancer.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, ovarian cancer, endometrial cancer, uterine sarcoma, cervical carcinoma, breast cancer, lung cancer, prostate cancer, ocular melanoma, and any MISIIR-expressing tumor.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undertermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1 \times 10^5$ cells/kg to about $1 \times 10^{11}$ cells/kg $10^4$ and at or about $10^{11}$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1 \times 10^5$ T cells/kg, $1.5 \times 10^5$ T cells/kg, $2 \times 10^5$ T cells/kg, or $1 \times 10^6$ T cells/kg body weight. In other exemplary embodiments, a suitable dosage range of modified cells for use in a method of the present disclosure includes, without limitation, from about $1 \times 10^5$ cells/kg to about $1 \times 10^6$ cells/kg, from about $1 \times 10^6$ cells/kg to about $1 \times 10^7$ cells/kg, from about $1 \times 10^7$ cells/kg about $1 \times 10^8$ cells/kg, from about $1 \times 10^8$ cells/kg about $1 \times 10^9$ cells/kg, from about $1 \times 10^9$ cells/kg about $1 \times 10^{10}$ cells/kg, from about $1 \times 10^{10}$ cells/kg about $1 \times 10^{11}$ cells/kg. In an exemplary embodiment, a suitable dosage for use in a method of the present disclosure is about $1 \times 10^8$ cells/kg. In an exemplary embodiment, a suitable dosage for use in a method of the present disclosure is about $1 \times 10^7$ cells/kg. In other embodiments, a suitable dosage is from about $1 \times 10^7$ total cells to about $5 \times 10^7$ total cells. In some embodiments, a suitable dosage is from about $1 \times 10^8$ total cells to about $5 \times 10^8$ total cells. In some embodiments, a suitable dosage is from about $1.4 \times 10^7$ total cells to about $1.1 \times 10^9$ total cells. In an exemplary embodiment, a suitable dosage for use in a method of the present disclosure is about $7 \times 10^9$ total cells.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1 \times 10^5$ $CD4^+$ and/or $CD8^+$ cells/kg, $1.5 \times 10^5$ $CD4^+$ and/or $CD8^+$ cells/kg, $2 \times 10^5$ $CD4^+$ and/or $CD8^+$ cells/kg, or $1 \times 10^6$ $CD4^+$ and/or $CD8^+$ cells/kg body weight. In some embodiments, the cells are administered at or within a certain range of error of, greater than, and/or at least about $1 \times 10^6$, about $2.5 \times 10^6$, about $5 \times 10^6$, about $7.5 \times 10^6$, or about $9 \times 10^6$ $CD4^+$ cells, and/or at least about $1 \times 10^6$, about $2.5 \times 10^6$, about $5 \times 10^6$, about $7.5 \times 10^6$, or about $9 \times 10^6$ CD8+ cells, and/or at least about $1 \times 10^6$, about $2.5 \times 10^6$, about $5 \times 10^6$, about $7.5 \times 10^6$, or about $9 \times 10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to $CD8^+$ cells) is between at or about 5:1 and at or about 5:1

(or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In certain embodiments, the modified cells of the invention (e.g., a modified cell comprising a CAR) may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology*, 15:47; Teachey et al. (2016) *Cancer Discov*, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

In one aspect, the invention includes a method for treating cancer in a subject in need thereof, the method comprising administering to the subject a modified cell comprising a CAR, wherein the CAR comprises a nanobody retrieved by the sequential tumor-related antibody and antigen retrieving (STAR) method, a transmembrane domain, and an intracellular signaling domain.

In another aspect, the invention provides a method for treating cancer in a subject in need thereof, the method comprising administering to the subject a modified cell comprising a CAR, wherein the CAR comprises a CD13-specific nanobody, a transmembrane domain, and an intracellular signaling domain.

A method for treating cancer in a subject in need thereof, the method comprising administering to the subject a modified cell comprising a CAR, wherein the CAR comprises a CDH17-specific nanobody, a transmembrane domain, and an intracellular signaling domain.

In certain embodiments, the T cell is a human cell. In certain embodiments, the T cell is autologous.

Nanobodies and Antibody Drug Conjugates (ADCs)

Also provided in the invention are nanobodies. In certain embodiments, the nanobody specifically binds to CD13. In certain embodiments, the nanobody specifically binds to CDH17. In certain embodiments, the nanobody specifically binds to the first domain of CDH17. In certain embodiments, the nanobody is encoded by the nucleotide sequence of SEQ ID NO: 1. In certain embodiments, the nanobody comprises the amino acid sequence of SEQ ID NO: 2. In certain embodiments, the nanobody comprises a CDR1 sequence comprising the amino acid sequence of SEQ ID NO: 3. In certain embodiments, the nanobody comprises a CDR2 sequence comprising the amino acid sequence of SEQ ID NO: 4. In certain embodiments, the nanobody comprises a CDR3 sequence comprising the amino acid sequence of ID NO: 5.

In certain embodiments, the nanobody comprises the amino acid sequence of SEQ ID NO: 19. In certain embodiments, the nanobody comprises a CDR1 sequence comprising the amino acid sequence of SEQ ID NO: 25. In certain embodiments, the nanobody comprises a CDR2 sequence comprising the amino acid sequence of SEQ ID NO: 26. In certain embodiments, the nanobody comprises a CDR3 sequence comprising the amino acid sequence of SEQ ID NO: 27.

In certain embodiments, the nanobody comprises the amino acid sequence of SEQ ID NO: 23. In certain embodiments, the nanobody comprises a CDR1 sequence comprising the amino acid sequence of SEQ ID NO: 28. In certain embodiments, the nanobody comprises a CDR2 sequence comprising the amino acid sequence of SEQ ID NO: 29. In certain embodiments, the nanobody comprises a CDR3 sequence comprising the amino acid sequence of SEQ ID NO: 30.

Also provided in the invention are antibody drug conjugates (ADCs), comprising any of the nanobodies disclosed herein linked/conjugated to a drug (e.g. a cancer cell-killing drug), or a toxin, or a radioisotope. In certain embodiments, NETs can be specifically targeted via CAR T cells or a NET-specific ADC to effectively eradicate NET cells. In certain embodiments, specific cell surface tumor-associated antigens and corresponding antibodies (nanobodies) are identified used the STAR system described elsewhere herein and conjugated to a drug/toxin/radioisotope. In certain embodiments, the invention includes an ADC comprising nanobody VH157 linked to a drug/toxin/radioisotope. In certain embodiments, the ADC comprises nanobody VH163 linked to a drug/toxin/radioisotope. In certain embodiments, the ADC comprises nanobody VHH1 linked to a drug/toxin/radioisotope. In certain embodiments, the ADC comprises a CD13-specific nanobody linked to a drug/toxin/radioisotope. In certain embodiments, the ADC comprises a CDH17-specific nanobody linked to a drug/toxin/radioisotope.

In certain embodiments, the ADC comprises a nanobody comprising the amino acid sequence of any one of SEQ ID NOs: 2, 19, or 24, linked to a drug/toxin/radioisotope.

The antibodies (nanobodies) can be linked/conjugated to any drug or cancer targeting agent known to one of skill in the art, including but not limited to maytansinoid (DM1), or SSTR2-binding octreotide, or toxin, including but not limited to paclitaxel, auristatin (MMAE and MMAF), dauxrubicin, duocarmycin A, 5-fluoruracil, methotrexate, tutbulin polymerization inhibitors, ravtansine (DM4), Ricin A. The nanobodies may also be linked to radioactive isotopes, including but not limited to 90Y and 177Lu, 111In, and such ADC can also be used for imaging applications (e.g. imaging cancer cells).

In certain embodiments, the ADC comprises nanobody VHH1 conjugated to DM1. In certain embodiments, the ADC comprises a first VHH1 nanobody linked to a second VHH1 nanobody (VLV) conjugated to DM1. In certain embodiments, the VHH1 or VLV is linked to DM1 and another agent including, but not limited to, any of the above described drugs, toxins, and radioactive isotopes.

Vectors

A vector may be used to introduce the CAR into a T cell as described elsewhere herein. In certain aspects, the invention includes vectors comprising nucleic acid sequences encoding a CAR. The vector can comprise a plasmid vector, viral vector, retrotransposon (e.g. piggyback, sleeping beauty), site directed insertion vector (e.g. CRISPR, Zn finger nucleases, TALEN), suicide expression vector, lentiviral vector, RNA vector, or other known vector in the art.

The production of any of the molecules described herein can be verified by sequencing. Expression of the full length proteins may be verified using immunoblot, immunohistochemistry, flow cytometry or other technology well known and available in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the EF-1 alpha promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

Expansion of T Cells

As demonstrated by the data disclosed herein, expanding the T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Nanobody Phage Library Panning

The titer of concentrated phage was generally $1 \times 10^{13}$ to $1 \times 10^{14}$ cfu/mL. In the first round of panning, the phage was applied to bind THP-1 directly, followed by wash, acidic glycine elution and neutralization, to enrich the tumor specific Nb-expressing phage. In the second round of panning, the elution of phage was amplified and concentrated to bind Jurkat cells as the negative selection. The unbound phage from Jurkat cells were incubated with THP-1 cells to enrich and then to be eluted with glycine solution.

Construction of Nanobody CAR Vector

Figure 2A:
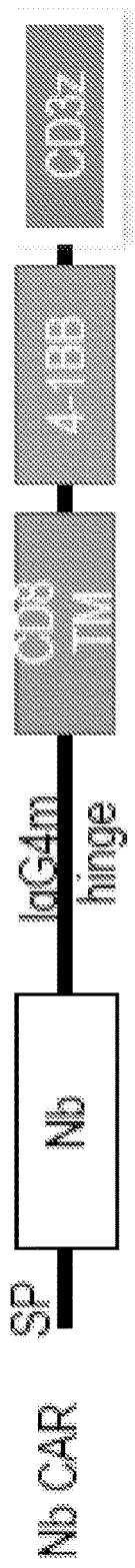

Generation of the Nanobody CAR (Nb CAR) constructs in lentiviral vector was shown in FIG. 2A. In brief, the plasmid backbone is pHIV-eGFP, a third-generation self-inactivating lentiviral vector plasmid. Nb CAR constructs, including CD8 signal peptide (SP), SfiI cut sites, IgG4m hinge, 4-1BB domain and CD3z domain, were custom synthesized by IDT-DNA. IRES-GFP was used as a marker to track Nb CAR positive cells. Nb CAR expression was confirmed by Western blots using anti-CD3z (FIG. 8A) (Abcam). Nanobody fragments were cloned into in-frame from pComb3XSS into pHIV-eGFP-CAR at the two sequential SfiI sites.

In Vivo Tumor-Mediated Selection of Nanobodies from CAR T Cells

Nanobody cDNAs isolated from cell based display were amplified with PCR using primers "2nd round Forward" and "2nd round Backward", followed by SfiI digestion and ligation into pHIV-eGFP-CAR vector. The ligation product was transformed to $E.\ coli$ competent cells, followed by lentivirus packaging and infecting activated human primary T cells to generate Nb-lib-CAR-expressing T cells. The resulting T cells or untransduced (UTD) T cells were administrated intravenously into NSG mice bearing either THP-1 tumor or K562 tumor, as shown in FIG. 1B. Fourteen days later, cDNAs for nanobodies were amplified by PCR from the genomic DNA isolated from the tumor infiltrated Nb-lib-CAR T cells, with the primer Nb-Amp-Forward, 5'-AT-TCAGGTGTCGTGAGCGG (SEQ ID NO: 6); and Nb-Amp-Backward, 5'-AGGAGAAGGACCCCACAAGT (SEQ ID NO: 7). The PCR product was digested with SfiI and inserted into pComb-3XSS, followed by randomly picking of individual clones and sequencing with primer Nb-Seq-Forward, 5-CAGCTATCGCGATTGCAGT (SEQ ID NO: 8).

Animals and In Vivo Models

All laboratory mice were maintained on a 12 hr light-dark cycle. NOD/Shi-scid/IL-2Rγnull (NSG) mice, 8-12 weeks old, were obtained from Jackson Laboratories. NSG mice were inoculated with $1 \times 10^7$ cells of THP-1 or HL60 subcutaneously, or with $0.5 \times 10^7$ cells of K562 subcutaneously. When tumor volume reached 100 mm$^3$ about 12 days after xenograft, Nb CAR T cells or untransduced (UTD) human T cells ($1 \times 10^7$ cells) were administrated via tail vein. Mice and tumors were monitored every other day. Tumor dimensions were measured with Vernier calipers and tumor volume was calculated as ½ larger diameter×(smaller diameter).

NSG mice were conditioned by Busulfex (30 mg/kg) 24 hrs prior to tail injection with $2 \times 10^7$ of patient-derived AML cells. Two weeks later CAR or UTD T cells were transduced into the mice. The recipient mice were sacrificed at the experimental end point based on the protocol, and the long bones (femurs), spleens and livers were collected for histological analysis by H & E staining. Mice were sacrificed according to protocol when moribund or upon the development of hind-limb paralysis.

Statistical Analysis

Microsoft Excel and GraphPad Prism software was used for statistical analysis.

Student's t test was used to determine the significance of the results unless otherwise indicated. Kaplan-Meier statistical analysis was performed using the log rank test. In the figures, asterisks denote statistically significant p values (*, $p<0.05$, , $p<0.01$, *, $p<0.001$), and "ns" indicates lack of statistical significance ($p>0.05$).

Cell Lines, Cell Culture, Plasmids and Antibodies

The THP-1, Jurkat, K562, HL60, U937, MV4-11, NB4 and SKOV3 cell lines were obtained from the ATCC and maintained in RPMI1640 with 10% FBS and 1% penicillin/streptomycin (R10 medium) and maintained at 37 C and 5% $CO_2$. HEK293T cells were obtained from ATCC and cultured in DMEM supplemented with 10% fetal bovine serum (FBS). NET NT-3 cell line was cultured in RPMI medium supplemented with 10% FBS, penicillin/streptomycin, HEPES, EGF (20 ng/mL), and FGF2 (10 ng/mL). Deidentified Patient derived AML cells were obtained from the University of Pennsylvania Stem Cell and Xenograft Core facility, and maintained in the R10 medium. Normal donor total T cells were obtained from the Human Immunology Core at University of Pennsylvania, and maintained in the R10 medium.

pComb3XSS was a gift from Carlos Barbas (Addgene plasmid #63890). pHIV-EGFP was a gift from Bryan Welm & Zena Werb (Addgene plasmid #21373). lentiCRISPR v2 was a gift from Feng Zhang (Addgene plasmid #52961). Human membrane protein cDNA library were provided by High-throughput Screen Core at University of Pennsylvania.

Nanobody Phage Library Construction from the THP-1 Cell-Immunized Llama

Llama was immunized with $2 \times 10^7$ of THP-1 cells monthly for 3 times (Caprologics, MA). Peripheral blood mononuclear cells (PBMCs) isolation, RNA extraction and cDNA synthesis were performed as previously described (Zhang, X. et al. (2016). J Immunol 196, 1591-1603). In brief, PBMCs were isolated from whole blood of immunized llama through Ficoll gradient centrifugation (GE). Total RNA was extracted by the RNeasy Mini Kit (QIAGEN) as the manufacturer's instructions, followed by cDNA synthesis from SuperScript™ III First-Strand Synthesis System (Invitrogen).

Nanobody encoding fragments were amplified from llama PBMCs cDNA by two rounds of PCR as instructed in "Phage Display, a laboratory Manual", with two pairs of nesting primers containing two flanking SfiI (GGCCNNNNNGGCC; SEQ ID NO: 9) sites as listed. 1st round Forward, 5'-GTCCTGGCTGCTCTTCTACAAGG (SEQ ID NO: 10); Backward, 5'-GGTACGTGCTGTT-GAACTGTTCC (SEQ ID NO: 11). 2nd round Forward, 5'-GAGGAGGAGGAGGAG-GAGGCGGGGCCCAGGCGGCCCAGGTG CAGCTGCAGGAGTCTGGRGGAGG (SEQ ID NO: 12); Backward, 5'-GAGGAG GAGGAGGAG-GAGCCTGGCCGGCCTGGC-CACTAGTGGCGGCCGCTGAGGAGA CGGTGACCTGGGT (SEQ ID NO: 13). The PCR product was digested with SfiI enzymes, followed by cloning into the phagemid system pComb3XSS. The ligation product was transformed into $E.\ coli$ competent cells, yielding ~$10^9$ single clones/ug ligated DNA in transformation. The resulting phage library was generated by infection with wild type M13 helper phage, and concentrated from supernatant for binding cancer cell surface.

In Vitro Analysis of T Cell Function:

For T-cell transduction, HEK293T cells were co-transfected with lenti-vector plasmid, psPAX2 and VSV-G plasmids DNA to produce the lentivirus 48h after transfection. Normal donor T cells were positively selected from leukapheresis packs using anti-CD4 and CD8 microbeads (Miltenyi), expanded in vitro with anti-CD3/CD28 beads (Invitrogen) for up to 12 days. Total T cells were transduced with lentiviral 24 hours after activation. The resulting virus from the supernatant were concentrated via untracentrifuation at 25,000 g for 2.5 h at 4 C.

Killing assays were performed as previously described (Cao, L. F. et al. (2010) *Cytometry A* 77, 534-545). In brief, target cells were labeled by anti-CD33 (BD) for detecting cell number with flow cytometry analysis or labeled by CellTrace Far Red for tracing cell division. Target cells were incubated with effector T cells for 16 hrs at a series of ratios. Cells were then harvested, washed, and stained by Propidium Iodide prior to flow cytometry analysis. Quantification were calculated by either Countbright beads or volume.

To detect cytokine secretion, effector and target cells were incubated at a 1:1 ratio in R10 medium for 16 hrs as indicated. Supernatant was analyzed using Human TNF-alpha or IFN-gamma DuoSet ELISA kits according to the manufacturer's instructions (R&D System).

To detect cell degranulation, activated and Nb CAR transduced or untransduced T cells ($1 \times 10^5$ cells) were co-cultured with THP-1 or K526 cells at a 1:1 ratio in 96-well plates for 4 hrs, in the presence of APC-conjugated anti-CD107a antibody, followed by wash and flow cytometry analysis.

To monitor cell proliferation assay, T cells were labeled by CellTrace™ Far Red Cell Proliferation Kit (Invitrogen) as the manufacturer's instructions. The reaction was quenched with R10 medium, and the cells were washed twice. T cells were incubated at a 1:1 ratio with heat-inactivated target cells for 96 hrs.

THP-1 CD13 Knockout Cell Line:

To knockout CD13 in THP-1 cell line, LentiCRISPRv2.0 vector was applied according to the protocol (Sanjana, N. E. et al, (2014) Nature methods 11, 783-784). sgRNA targeting human CD13 were listed as below, sgCD13-1 ATGGCCGGCTCATCGAAGCA (SEQ ID NO: 14), sgCD13-2 CTTCCCATGCTTCGATGAGC (SEQ ID NO: 15), sgCD13-2 CTTCATGGGGCCATAGACCT (SEQ ID NO: 16). Plasmids were confirmed by sequencing and packaged into lentivirus, followed by infecting THP-1 cells. Single clones were randomly picked up from each group after puromycin selection (2.5 ug/mL) for 4 days.

Switchable CAR (sCAR) T System:

Anti-PNE single chain variable fragment (scFv) was custom synthesized by GeneArt (Rodgers, D. T. et al. (2016) *Proceedings of the National Academy of Sciences of the United States of America* 113, E459-468), followed by insertion into pHIV-41BB-CD3z vector. sCAR lentivirus was packaged and used to transduce human T cells. sCAR expression was detected by flow cytometry and western blot. Nb157 with C-terminal PNE (Nb157-C-PNE) or with N-terminal PNE (Nb157-N-PNE) were constructed by molecular cloning, followed by prokaryotic expression and purification via Ni-NTA affinity (QIAGEN) in TOP10 (Invitrogen) induced by isopropyl-β-d-thiogalactoside (IPTG).

Development of Nanobody (NB)-Driven CAR T Cells for AML Therapy.

After preparing the variable domains heavy-chain camelid antibodies (VHH) CAR expressing library, the lentivirus vectors were packaged and the primary human T cells were transformed to prepare the VHH CAR expressing T cell library, followed by treatment the NSG mice with THP-1 tumor or K562 tumor. After two weeks, the tumor was removed and a PCR was done on the VHH and sequence.

Through this method, VHH157 and VHH163 were identified as THP-1 specific nanobodies. VHH157 CAR and VHH163 CAR were constructed with the structure as shown below.

VHH157 CAR (SEQ ID NO: 17):

MALPVTALLLPLALLLHAARPGSAAQAAQVQLQESGGGLVQPGGSLSLS

CTASGFTFSSYSMAWVRQAPGKGPEWVSGIYPSDGKTRYADFVKGRFSI

SRDNAKNMLYLQMNNLEPEDTALYYCARGITGLGPRGQGTQVTVSSAAA

*TSGQAGQSGESKYGPPCPPCPAS*YIWAPLAGTCGVLLLSLVITLYCKRG

RKKLLYIFKQPFMRPVQTTQEEDGCSCRFPEEEEGGCELRVKFSRSADA

PAYKQGQNQLYNELNLGRREEYDVLDKRRGRDPEMGGKPRRKNPQEGLY

NELQKDKMAEAYSEIGMKGERRRGKGHDGLYQGLSTATKDTYDALHMQA

LPPR

Bold is signal peptide (SEQ ID NO: 18)
Underlined is VHH157 (SEQ ID NO: 19)
Italicized is IgG4mh (SEQ ID NO: 20)
Dotted underlined is CD8 transmembrane (SEQ ID NO: 21)
Double underlined is 4-1BB and CD3z (SEQ ID NO: 22)
SYSMA is the CDR1 (SEQ ID NO: 25)
GIYPSDGKTRYADFVKGR is the CDR2 (SEQ ID NO: 26)
ARGITGLGP is the CDR3 (SEQ ID NO: 27)

VHH163 CAR (SEQ ID NO: 23):

MALPVTALLLPLALLLHAARPGSAAQAAQVQLQESGGGLVQPGGSLRLS

CVPSGFTFDGYLIGWFRQAPGSERKAVSCISVNGDRTNYADSVKGRFTI

SRDNAKNTVYLQMNSLRPNDTAIYYCATRRGNRLYNNNCPYFEYGTWGQ

GTQVTVSSAA*ATSGQAGQSGESKYGPPCPPCPAS*

YIWAPLAGTCGVLLLSLVITLYCKRGRKKLLYIFKQPFMRPVQTTQEED

GCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERR

RGKGHDGLYOGLSTATKDTYDALHMOALPPR

Bold is signal peptide (SEQ ID NO: 18)
Underlined is VHH163 (SEQ ID NO: 24)
Italicized is IgG4mh (SEQ ID NO: 20)
Dotted underlined is CD8 transmembrane (SEQ ID NO: 21)
Double underlined is 4-1BB and CD3z (SEQ ID NO: 22)
GYLIG is the CDR1 (SEQ ID NO: 28)
CISVNGDRTNYADSVKGR is the CDR2 (SEQ ID NO: 29)
ATRRGNRLYNNNCPYFEYGT is the CDR3 (SEQ ID NO: 30)

VHH157-BBz pLenti-CAR Vector
source 1 . . . 8721
/organism="VHH157BBz pHIV-eGFP"
/mol_type="other DNA"
misc_feature 2622 . . . 3805
/note="EF1a Promoter"
misc_feature 3832 . . . 3894
/note="CD8 Leader"
misc_feature 3901 . . . 4293
/note="VHH157"
misc_feature 4300 . . . 4335
/note="IgG4 Hinge"
misc_feature 4342 . . . 4410
/note="CD8TM"
misc_feature 4368 . . . 4872

/note="Syn muCD19-BBz"
misc_feature 4411 . . . 4536
/note="4-1BB"
misc_feature 4537 . . . 4872
/note="CD3zeta"

misc_feature 4882 . . . 5466
/note="IRES"
misc_feature 5473 . . . 6186
/note="EGFP"

(SEQ ID NO: 31)

```
   1 gtcgacggat cgggagatct cccgatcccc tatggtgcac tctcagtaca atctgctctg
  61 atgccgcata gttaagccag tatctgctcc ctgcttgtgt gttggaggtc gctgagtagt
 121 gcgcgagcaa aatttaagct acaacaaggc aaggcttgac cgacaattgc atgaagaatc
 181 tgcttagggt taggcgtttt gcgctgcttc gcgatgtacg ggccagatat acgcgttgac
 241 attgattatt gactagttat taatagtaat caattacggg gtcattagtt catagcccat
 301 atatggagtt ccgcgttaca taacttacgg taaatggccc gcctggctga ccgcccaacg
 361 acccccgccc attgacgtca ataatgacgt atgttcccat agtaacgcca atagggactt
 421 tccattgacg tcaatgggtg gagtatttac ggtaaactgc ccacttggca gtacatcaag
 481 tgtatcatat gccaagtacg ccccctattg acgtcaatga cggtaaatgg cccgcctggc
 541 attatgccca gtacatgacc ttatgggact ttcctacttg gcagtacatc tacgtattag
 601 tcatcgctat taccatggtg atgcggtttt ggcagtacat caatgggcgt ggatagcggt
 661 ttgactcacg gggatttcca agtctccacc ccattgacgt caatgggagt ttgttttggc
 721 accaaaatca acgggacttt ccaaaatgtc gtaacaactc cgccccattg acgcaaatgg
 781 gcggtaggcg tgtacggtgg gaggtctata taagcagcgc gttttgcctg tactgggtct
 841 ctctggttag accagatctg agcctgggag ctctctggct aactagggaa cccactgctt
 901 aagcctcaat aaagcttgcc ttgagtgctt caagtagtgt gtgcccgtct gttgtgtgac
 961 tctggtaact agagatccct cagaccctt tagtcagtgt ggaaaatctc tagcagtggc
1021 gcccgaacag ggacttgaaa gcgaaaggga accagagga gctctctcga cgcaggactc
1081 ggcttgctga agcgcgcacg gcaagaggcg aggggcggcg actggtgagt acgccaaaaa
1141 ttttgactag cggaggctag aaggagagag atgggtgcga gagcgtcagt attaagcggg
1201 ggagaattag atcgcgatgg gaaaaaattc ggttaaggcc agggggaaag aaaaaatata
1261 aattaaaaca tatagtatgg gcaagcaggg agctagaacg attcgcagtt aatcctggcc
1321 tgttagaaac atcagaaggc tgtagacaaa tactgggaca gctacaacca tcccttcaga
1381 caggatcaga agaacttaga tcattatata atacagtagc aaccctctat tgtgtgcatc
1441 aaaggataga gataaaagac accaaggaag ctttagacaa gatagaggaa gagcaaaaca
1501 aaagtaagac caccgcacag caagcggccg ccgcgctga tcttcagacc tggaggagga
1561 gatatgaggg acaattggag aagtgaatta tataaatata agtagtaaa aattgaacca
1621 ttaggagtag caccaccaa ggcaaagaga agagtggtgc agagagaaaa aagagcagtg
1681 ggaataggag ctttgttcct tgggttcttg ggagcagcag gaagcactat gggcgcagcg
1741 tcaatgacgc tgacggtaca ggccagacaa ttattgtctg gtatagtgca gcagcagaac
1801 aatttgctga gggctattga ggcgcaacag catctgttgc aactcacagt ctggggcatc
1861 aagcagctcc aggcaagaat cctggctgtg aaagatacc taaggatca acagctcctg
1921 gggatttggg gttgctctgg aaaactcatt tgcaccactg ctgtgccttg aatgctagt
1981 tggagtaata aatctctgga acagatttgg aatcacacga cctggatgga gtgggacaga
2041 gaaattaaca attacacaag cttaatacac tccttaattg aagaatcgca aaaccagcaa
2101 gaaaagaatg aacaagaatt attggaatta gataaatggg caagtttgtg gaattggttt
2161 aacataacaa attggctgtg gtatataaaa ttattcataa tgatagtagg aggcttggta
```

-continued

```
2221 ggtttaagaa tagtttttgc tgtactttct atagtgaata gagttaggca gggatattca
2281 ccattatcgt ttcagaccca cctcccaacc ccgaggggac ccgacaggcc cgaaggaata
2341 gaagaagaag gtggagagag agacagagac agatccattc gattagtgaa cggatcggca
2401 ctgcgtgcgc caattctgca gacaaatggc agtattcatc cacaatttta aagaaaagg
2461 ggggattggg gggtacagtg caggggaaag aatagtagac ataatagcaa cagacataca
2521 aactaaagaa ttacaaaaac aaattacaaa aattcaaaat tttcgggttt attacaggga
2581 cagcagagat ccagtttggt tagtaccggg cccgctctag ccgtgaggct ccggtgcccg
2641 tcagtgggca gagcgcacat cgcccacagt ccccgagaag ttggggggag gggtcggcaa
2701 ttgaaccggt gcctagagaa ggtggcgcgg ggtaaactgg gaaagtgatg tcgtgtactg
2761 gctccgcctt tttcccgagg gtgggggaga accgtatata agtgcagtag tcgccgtgaa
2821 cgttcttttt cgcaacgggt ttgccgccag aacacaggta agtgccgtgt gtggttcccg
2881 cgggcctggc ctctttacgg gttatggccc ttgcgtgcct tgaattactt ccacctggct
2941 gcagtacgtg attcttgatc ccgagcttcg ggttggaagt gggtgggaga gttcgaggcc
3001 ttgcgcttaa ggagcccctt cgcctcgtgc ttgagttgag gcctggctg ggcgctgggg
3061 ccgccgcgtg cgaatctggt ggcaccttcg cgcctgtctc gctgctttcg ataagtctct
3121 agccatttaa aattttgat gacctgctgc gacgcttttt ttctggcaag atagtcttgt
3181 aaatgcgggc caagatctgc acactggtat ttcggttttt ggggccgcgg gcggcgacgg
3241 ggcccgtgcg tcccagcgca catgttcggc gaggcgggc ctgcgagcgc ggccaccgag
3301 aatcggacgg gggtagtctc aagctggccg gcctgctctg gtgcctggcc tcgcgccgcc
3361 gtgtatcgcc ccgccctggg cggcaaggct ggcccggtcg gcaccagttg cgtgagcgga
3421 aagatggccg cttcccggcc ctgctgcagg gagctcaaaa tggaggacgc ggcgctcggg
3481 agagcgggcg ggtgagtcac ccacacaaag gaaaagggcc tttccgtcct cagccgtcgc
3541 ttcatgtgac tccacggagt accgggcgcc gtccaggcac ctcgattagt tctcgagctt
3601 ttggagtacg tcgtctttag gttgggggga ggggttttat gcgatggagt ttccccacac
3661 tgagtgggtg gagactgaag ttaggccagc ttggcacttg atgtaattct ccttggaatt
3721 tgccctttt gagtttggat cttggttcat tctcaagcct cagacagtgg ttcaaagttt
3781 ttttcttcca tttcaggtgt cgtgagcggc cgctgagtta actattctag aatggcctta
3841 ccagtgaccg ccttgctcct gccgctggcc ttgctgctcc acgccgccag gccgggatcc
3901 gcggcccagg cggcccaggt gcagctgcag gagtctgggg gaggcttggt gcagcctggg
3961 gggtctctga gcctctcctg tacagcctct ggattcacgt tcagtagtta ctccatggcc
4021 tgggtccgcc aggctccagg aagggaccc gaatgggtct cagggattta cccttctgat
4081 ggtaagacaa ggtatgcaga cttcgtgaag gccgattca gcatctccag agacaacgcc
4141 aagaatatgt tgtatctgca aatgaacaac ctggaacctg aggacacggc cctatattac
4201 tgtgcgagag gtatcaccgg attgggaccc cggggccagg ggacccaggt caccgtctcc
4261 tcagcggccg ccactagtgg ccaggccggc cagtccggag agagcaagta cggccctccc
4321 tgccccccct tgcctgctag ctacatctgg gcgcccttgg ccgggacttg tggggtcctt
4381 ctcctgtcac tggttatcac cctttactgc aaacggggca gaaagaaact cctgtatata
4441 ttcaaacaac catttatgag accagtacaa actactcaag aggaagatgg ctgtagctgc
4501 cgatttccag aagaagaaga aggaggatgt gaactgagag tgaagttcag caggagcgca
4561 gacgcccccg cgtacaagca gggccagaac cagctctata acgagctcaa tctaggacga
```

```
4621 agagaggagt acgatgtttt ggacaagaga cgtggccggg accctgagat ggggggaaag
4681 ccgagaagga agaaccctca ggaaggcctg tacaatgaac tgcagaaaga taagatggcg
4741 gaggcctaca gtgagattgg gatgaaaggc gagcgccgga ggggcaaggg gcacgatggc
4801 ctttaccagg gtctcagtac agccaccaag gacacctacg acgcccttca catgcaggcc
4861 ctgcccccct gctaaagatc cgcccctctc cctcccccc ccctaacgtt actggccgaa
4921 gccgcttgga ataaggccgg tgtgcgtttg tctatatgtt attttccacc atattgccgt
4981 cttttggcaa tgtgagggcc cggaaacctg gccctgtctt cttgacgagc attcctaggg
5041 gtctttcccc tctcgccaaa ggaatgcaag gtctgttgaa tgtcgtgaag gaagcagttc
5101 ctctggaagc ttcttgaaga caaacaacgt ctgtagcgac cctttgcagg cagcggaacc
5161 ccccacctgg cgacaggtgc ctctgcggcc aaaagccacg tgtataagat acacctgcaa
5221 aggcggcaca accccagtgc cacgttgtga gttggatagt tgtggaaaga gtcaaatggc
5281 tctcctcaag cgtattcaac aaggggctga aggatgccca aaggtaccc cattgtatgg
5341 gatctgatct ggggcctcgg tgcacatgct ttacatgtgt ttagtcgagg ttaaaaaaac
5401 gtctaggccc cccgaaccac ggggacgtgg ttttcctttg aaaaacacga tgataatatg
5461 gccacaacca tggtgagcaa gggcgaggag ctgttcaccg gggtggtgcc catcctggtc
5521 gagctggacg gcgacgtaaa cggccacaag ttcagcgtgt ccggcgaggg cgagggcgat
5581 gccacctacg gcaagctgac cctgaagttc atctgcacca ccggcaagct gcccgtgccc
5641 tggcccaccc tcgtgaccac cctgacctac ggcgtgcagt gcttcagccg ctaccccgac
5701 cacatgaagc agcacgactt cttcaagtcc gccatgcccg aaggctacgt ccaggagcgc
5761 accatcttct tcaaggacga cggcaactac aagacccgcg ccgaggtgaa gttcgagggc
5821 gacaccctgg tgaaccgcat cgagctgaag ggcatcgact tcaaggagga cggcaacatc
5881 ctggggcaca agctggagta caactacaac agccacaacg tctatatcat ggccgacaag
5941 cagaagaacg gcatcaaggt gaacttcaag atccgccaca acatcgagga cggcagcgtg
6001 cagctcgccg accactacca gcagaacacc cccatcggcg acggccccgt gctgctgccc
6061 gacaaccact acctgagcac ccagtccgcc ctgagcaaag accccaacga gaagcgcgat
6121 cacatggtcc tgctggagtt cgtgaccgcc gccgggatca ctctcggcat ggacgagctg
6181 tacaagtaaa gcggccgcat cgataccgtc gacctcgatc gagacctaga aaaacatgga
6241 gcaatcacaa gtagcaatac agcagctacc aatgctgatt gtgcctggct agaagcacaa
6301 gaggaggagg aggtgggttt tccagtcaca cctcaggtac cttaagacc aatgacttac
6361 aaggcagctg tagatcttag ccactttta aaagaaaagg ggggactgga agggctaatt
6421 cactcccaac gaagacaaga tatccttgat ctgtggatct accacacaca aggctacttc
6481 cctgattggc agaactacac accagggcca gggatcagat atccactgac ctttggatgg
6541 tgctacaagc tagtaccagt tgagcaagag aaggtagaag aagccaatga aggagagaac
6601 acccgcttgt tacaccctgt gagcctgcat gggatggatg acccggagag agaagtatta
6661 gagtggaggt ttgacagccg cctagcattt catcacatgg cccgagagct gcatccggac
6721 tgtactgggt ctctctggtt agaccagatc tgagcctggg agctctctgg ctaactaggg
6781 aacccactgc ttaagcctca ataaagcttg ccttgagtgc ttcaagtagt gtgtgcccgt
6841 ctgttgtgtg actctggtaa ctagagatcc ctcagaccct tttagtcagt gtggaaaatc
6901 tctagcagca tgtgagcaaa aggccagcaa aaggccagga accgtaaaaa ggccgcgttg
6961 ctggcgtttt tccataggct ccgcccccct gacgagcatc acaaaaatcg acgctcaagt
7021 cagaggtggc gaaacccgac aggactataa agataccagg cgtttccccc tggaagctcc
```

-continued

```
7081 ctcgtgcgct ctcctgttcc gaccctgccg cttaccggat acctgtccgc ctttctccct 7141 tcgggaagcg tggcgctttc tcatagctca cgctgtaggt atctcagttc ggtgtaggtc 7201 gttcgctcca agctgggctg tgtgcacgaa ccccccgttc agcccgaccg ctgcgcctta 7261 tccggtaact atcgtcttga gtccaacccg gtaagacacg acttatcgcc actggcagca 7321 gccactggta acaggattag cagagcgagg tatgtaggcg gtgctacaga gttcttgaag 7381 tggtggccta actacggcta cactagaaga acagtatttg gtatctgcgc tctgctgaag 7441 ccagttacct tcggaaaaag agttggtagc tcttgatccg gcaaacaaac caccgctggt 7501 agcggtggtt ttttgtttg caagcagcag attacgcgca gaaaaaaagg atctcaagaa 7561 gatcctttga tcttttctac ggggtctgac gctcagtgga acgaaaactc acgttaaggg 7621 attttggtca tgagattatc aaaaaggatc ttcacctaga tccttttaaa ttaaaaatga 7681 agttttaaat caatctaaag tatatatgag taaacttggt ctgacagtta ccaatgctta 7741 atcagtgagg cacctatctc agcgatctgt ctatttcgtt catccatagt tgcctgactc 7801 cccgtcgtgt agataactac gatacgggag ggcttaccat ctggccccag tgctgcaatg 7861 ataccgcgag acccacgctc accggctcca gatttatcag caataaacca gccagccgga 7921 agggccgagc gcagaagtgg tcctgcaact ttatccgcct ccatccagtc tattaattgt 7981 tgccgggaag ctagagtaag tagttcgcca gttaatagtt tgcgcaacgt tgttgccatt 8041 gctacaggca tcgtggtgtc acgctcgtcg tttggtatgg cttcattcag ctccggttcc 8101 caacgatcaa ggcgagttac atgatccccc atgttgtgca aaaaagcggt tagctccttc 8161 ggtcctccga tcgttgtcag aagtaagttg gccgcagtgt tatcactcat ggttatggca 8221 gcactgcata attctcttac tgtcatgcca tccgtaagat gcttttctgt gactggtgag 8281 tactcaacca agtcattctg agaatagtgt atgcggcgac cgagttgctc ttgcccggcg 8341 tcaatacggg ataataccgc gccacatagc agaactttaa aagtgctcat cattggaaaa 8401 cgttcttcgg ggcgaaaact ctcaaggatc ttaccgctgt tgagatccag ttcgatgtaa 8461 cccactcgtg cacccaactg atcttcagca tcttttactt tcaccagcgt ttctgggtga 8521 gcaaaaacag gaaggcaaaa tgccgcaaaa aagggaataa gggcgacacg gaaatgttga 8581 atactcatac tcttcctttt tcaatattat tgaagcattt atcagggtta ttgtctcatg 8641 agcggataca tatttgaatg tatttagaaa aataaacaaa tagggggttcc gcgcacattt 8701 ccccgaaaag tcccacctga c
```

VHH163-BBz pLenti-CAR Vector
  source 1 ... 8754
  /organism="VHH163-BBz pHIV-eGFP"
  /mol_type="other DNA"
  misc_feature 2622 ... 3805
  /note="EF 1a Promoter"
  misc_feature 3832 ... 3894
  /note="CD8 Leader"
  misc_feature 3901 ... 4326
  /note="VHH163"
  misc_feature 4333 ... 4368
  /note="IgG4 Hinge"
  misc_feature 4375 ... 4443
  /note="CD8TM"
  misc_feature 4401 ... 4905
  /note="Syn muCD19-BBz"
  misc_feature 4444 ... 4569
  /note="4-1BB"
  misc_feature 4570 ... 4905
  /note="CD3zeta"
  misc_feature 4915 ... 5499
  /note="IRES"
  misc_feature 5506 ... 6219
  /note="EGFP"

(SEQ ID NO: 32)
```
  1 gtcgacggat cgggagatct cccgatcccc tatggtgcac tctcagtaca atctgctctg 61 atgccgcata gttaagccag tatctgctcc ctgcttgtgt gttggaggtc gctgagtagt 121 gcgcgagcaa aatttaagct acaacaaggc aaggcttgac cgacaattgc atgaagaatc
```

-continued

```
 181 tgcttagggt taggcgtttt gcgctgcttc gcgatgtacg ggccagatat acgcgttgac
 241 attgattatt gactagttat taatagtaat caattacggg gtcattagtt catagcccat
 301 atatggagtt ccgcgttaca taacttacgg taaatggccc gcctggctga ccgcccaacg
 361 accccccgccc attgacgtca ataatgacgt atgttcccat agtaacgcca atagggactt
 421 tccattgacg tcaatgggtg gagtatttac ggtaaactgc ccacttggca gtacatcaag
 481 tgtatcatat gccaagtacg ccccctattg acgtcaatga cggtaaatgg cccgcctggc
 541 attatgccca gtacatgacc ttatgggact ttcctacttg gcagtacatc tacgtattag
 601 tcatcgctat taccatggtg atgcggtttt ggcagtacat caatgggcgt ggatagcggt
 661 ttgactcacg gggatttcca agtctccacc ccattgacgt caatgggagt ttgttttggc
 721 accaaaatca acgggacttt ccaaaatgtc gtaacaactc cgccccattg acgcaaatgg
 781 gcggtaggcg tgtacggtgg gaggtctata taagcagcgc gttttgcctg tactgggtct
 841 ctctggttag accagatctg agcctgggag ctctctggct aactagggaa cccactgctt
 901 aagcctcaat aaagcttgcc ttgagtgctt caagtagtgt gtgcccgtct gttgtgtgac
 961 tctggtaact agagatccct cagaccctt tagtcagtgt ggaaaatctc tagcagtggc
1021 gcccgaacag ggacttgaaa gcgaaaggga accagagga gctctctcga cgcaggactc
1081 ggcttgctga agcgcgcacg gcaagaggcg aggggcggcg actggtgagt acgccaaaaa
1141 ttttgactag cggaggctag aaggagagag atgggtgcga gagcgtcagt attaagcggg
1201 ggagaattag atcgcgatgg gaaaaaattc ggttaaggcc agggggaaag aaaaaatata
1261 aattaaaaca tatagtatgg gcaagcaggg agctagaacg attcgcagtt aatcctggcc
1321 tgttagaaac atcagaaggc tgtagacaaa tactgggaca gctacaacca tcccttcaga
1381 caggatcaga agaacttaga tcattatata atacagtagc aaccctctat tgtgtgcatc
1441 aaaggataga gataaaagac accaaggaag ctttagacaa gatagaggaa gagcaaaaca
1501 aaagtaagac caccgcacag caagcggccg ccgcgctga tcttcagacc tggaggagga
1561 gatatgaggg acaattggag aagtgaatta tataaatata agtagtaaa aattgaacca
1621 ttaggagtag cacccaccaa ggcaaagaga agagtggtgc agagagaaaa aagagcagtg
1681 ggaataggag cttgttcct tgggttcttg ggagcagcag aagcactat gggcgcagcg
1741 tcaatgacgc tgacggtaca ggccagacaa ttattgtctg gtatagtgca gcagcagaac
1801 aatttgctga gggctattga ggcgcaacag catctgttgc aactcacagt ctggggcatc
1861 aagcagctcc aggcaagaat cctggctgtg gaaagatacc taaaggatca acagctcctg
1921 gggatttggg gttgctctgg aaaactcatt tgcaccactg ctgtgccttg aatgctagt
1981 tggagtaata aatctctgga acagatttgg aatcacacga cctggatgga gtgggacaga
2041 gaaattaaca attacacaag cttaatacac tccttaattg aagaatcgca aaaccagcaa
2101 gaaaagaatg aacaagaatt attggaatta gataaatggg caagtttgtg gaattggttt
2161 aacataacaa attggctgtg gtatataaaa ttattcataa tgatagtagg aggcttggta
2221 ggtttaagaa tagttttgc tgtactttct atagtgaata gagttaggca gggatattca
2281 ccattatcgt ttcagaccca cctcccaacc ccgagggac ccgacaggcc cgaaggaata
2341 gaagaagaag gtggagagag agacagagac agatccattc gattagtgaa cggatcggca
2401 ctgcgtgcgc caattctgca gacaaatggc agtattcatc cacaatttta aaagaaaagg
2461 ggggattggg gggtacagtg caggggaaag aatagtagac ataatagcaa cagacataca
2521 aactaaagaa ttacaaaaac aaattacaaa aattcaaaat tttcgggttt attacaggga
```

-continued

```
2581 cagcagagat ccagtttggt tagtaccggg cccgctctag ccgtgaggct ccggtgcccg 2641 tcagtgggca gagcgcacat cgcccacagt ccccgagaag ttgggggggag gggtcggcaa 2701 ttgaaccggt gcctagagaa ggtggcgcgg ggtaaactgg gaaagtgatg tcgtgtactg 2761 gctccgcctt tttcccgagg gtgggggaga accgtatata agtgcagtag tcgccgtgaa 2821 cgttcttttt cgcaacgggt ttgccgccag aacacaggta agtgccgtgt gtggttcccg 2881 cgggcctggc ctctttacgg gttatggccc ttgcgtgcct tgaattactt ccacctggct 2941 gcagtacgtg attcttgatc ccgagcttcg ggttggaagt gggtgggaga gttcgaggcc 3001 ttgcgcttaa ggagcccctt cgcctcgtgc ttgagttgag gcctggcctg ggcgctgggg 3061 ccgccgcgtg cgaatctggt ggcaccttcg cgcctgtctc gctgctttcg ataagtctct 3121 agccatttaa aattttgat gacctgctgc gacgctttt ttctggcaag atagtcttgt 3181 aaatgcgggc caagatctgc acactggtat ttcggttttt ggggccgcgg gcggcgacgg 3241 ggcccgtgcg tcccagcgca catgttcggc gaggcggggc ctgcgagcgc ggccaccgag 3301 aatcggacgg gggtagtctc aagctggccg gcctgctctg gtgcctggcc tcgcgccgcc 3361 gtgtatcgcc ccgccctggg cggcaaggct ggcccggtcg gcaccagttg cgtgagcgga 3421 aagatggccg cttcccggcc ctgctgcagg gagctcaaaa tggaggacgc ggcgctcggg 3481 agagcgggcg ggtgagtcac ccacacaaag gaaaagggcc tttccgtcct cagccgtcgc 3541 ttcatgtgac tccacggagt accgggcgcc gtccaggcac ctcgattagt tctcgagctt 3601 ttggagtacg tcgtctttag gttgggggga ggggttttat gcgatggagt ttccccacac 3661 tgagtgggtg gagactgaag ttaggccagc ttggcacttg atgtaattct ccttggaatt 3721 tgccctttt gagtttggat cttggttcat tctcaagcct cagacagtgg ttcaaagttt 3781 ttttcttcca tttcaggtgt cgtgagcggc cgctgagtta actattctag aatggcctta 3841 ccagtgaccg ccttgctcct gccgctggcc ttgctgctcc acgccgccag gccgggatcc 3901 gcggcccagg cggcccaggt gcagctgcag gagtctggag gaggcttggt gcagcctggt 3961 gggtctctga gactctcctg tgtaccctct ggattcactt tcgatggtta tctcataggc 4021 tggttccgcc aggccccagg gagcgagcgg aaggcggtct catgtattag tgtgaatggt 4081 gatagaacaa actatgcaga ttccgtgaag ggccgattca ccatctccag agacaacgcc 4141 aagaacacgg tgtatctgca aatgaacagc ctgagaccta acgacacagc catttattac 4201 tgtgcgaccc gcaggggaaa tcgtctttat aataataact gcccatactt tgagtatggc 4261 acctggggcc aggggaccca ggtcaccgtc tcctcagcgg ccgccactag tggccaggcc 4321 ggccagtccg gagagagcaa gtacggccct ccctgccccc cttgccctgc tagctacatc 4381 tgggcgccct tggccgggac ttgtggggtc cttctcctgt cactggttat caccctttac 4441 tgcaaacggg gcagaaagaa actcctgtat atattcaaac aaccatttat gagaccagta 4501 caaactactc aagaggaaga tggctgtagc tgccgatttc cagaagaaga agaaggagga 4561 tgtgaactga gagtgaagtt cagcaggagc gcagacgccc ccgcgtacaa gcagggccag 4621 aaccagctct ataacgagct caatctagga cgaagagagg agtacgatgt tttggacaag 4681 agacgtggcc gggaccctga gatgggggga aagccgagaa ggaagaaccc tcaggaaggc 4741 ctgtacaatg aactgcagaa agataagatg gcggaggcct acagtgagat tgggatgaaa 4801 ggcgagcgcc ggaggggcaa ggggcacgat ggcctttacc agggtctcag tacagccacc 4861 aaggacacct acgacgccct tcacatgcag gccctgcccc ctcgctaaag atccgcccct 4921 ctccctcccc ccccctaac gttactgcc gaagccgctt ggaataaggc cggtgtgcgt 4981 ttgtctatat gttattttcc accatattgc cgtcttttgg caatgtgagg gcccggaaac
```

-continued

```
5041 ctggccctgt cttcttgacg agcattccta ggggtctttc ccctctcgcc aaaggaatgc 5101 aaggtctgtt gaatgtcgtg aaggaagcag ttcctctgga agcttcttga agacaaacaa 5161 cgtctgtagc gacccttgc aggcagcgga accccccacc tggcgacagg tgcctctgcg 5221 gccaaaagcc acgtgtataa gatacacctg caaaggcggc acaacccag tgccacgttg 5281 tgagttggat agttgtggaa agagtcaaat ggctctcctc aagcgtattc aacaaggggc 5341 tgaaggatgc ccagaaggta ccccattgta tgggatctga tctggggcct cggtgcacat 5401 gctttacatg tgtttagtcg aggttaaaaa aacgtctagg cccccgaac cacggggacg 5461 tggttttcct ttgaaaaaca cgatgataat atggccacaa ccatggtgag caagggcgag 5521 gagctgttca ccggggtggt gcccatcctg gtcgagctgg acggcgacgt aaacggccac 5581 aagttcagcg tgtccggcga gggcgagggc gatgccacct acggcaagct gaccctgaag 5641 ttcatctgca ccaccggcaa gctgcccgtg ccctggccca ccctcgtgac caccctgacc 5701 tacggcgtgc agtgcttcag ccgctacccc gaccacatga agcagcacga cttcttcaag 5761 tccgccatgc ccgaaggcta cgtccaggag cgcaccatct tcttcaagga cgacggcaac 5821 tacaagaccc gcgccgaggt gaagttcgag ggcgacaccc tggtgaaccg catcgagctg 5881 aagggcatcg acttcaagga ggacggcaac atcctggggc acaagctgga gtacaactac 5941 aacagccaca acgtctatat catggccgac aagcagaaga acggcatcaa ggtgaacttc 6001 aagatccgcc acaacatcga ggacggcagc gtgcagctcg ccgaccacta ccagcagaac 6061 acccccatcg gcgacggccc cgtgctgctg cccgacaacc actacctgag cacccagtcc 6121 gccctgagca aagaccccaa cgagaagcgc gatcacatgg tcctgctgga gttcgtgacc 6181 gccgccggga tcactctcgg catggacgag ctgtacaagt aaagcggccg catcgatacc 6241 gtcgacctcg atcgagacct agaaaaacat ggagcaatca caagtagcaa tacagcagct 6301 accaatgctg attgtgcctg gctagaagca caagaggagg aggaggtggg ttttccagtc 6361 acacctcagg tacctttaag accaatgact tacaaggcag ctgtagatct tagccacttt 6421 ttaaaagaaa aggggggact ggaagggcta attcactccc aacgaagaca agatatcctt 6481 gatctgtgga tctaccacac acaaggctac ttccctgatt ggcagaacta cacaccaggg 6541 ccagggatca gatatccact gacctttgga tggtgctaca agctagtacc agttgagcaa 6601 gagaaggtag aagaagccaa tgaaggagag aacacccgct tgttacaccc tgtgagcctg 6661 catgggatgg atgacccgga gagagaagta ttagagtgga ggtttgacag ccgcctagca 6721 tttcatcaca tggcccgaga gctgcatccg gactgtactg ggtctctctg gttagaccag 6781 atctgagcct gggagctctc tggctaacta gggaacccac tgcttaagcc tcaataaagc 6841 ttgccttgag tgcttcaagt agtgtgtgcc cgtctgttgt gtgactctgg taactagaga 6901 tccctcagac ccttttagtc agtgtggaaa atctctagca gcatgtgagc aaaaggccag 6961 caaaaggcca ggaaccgtaa aaaggccgcg ttgctggcgt ttttccatag gctccgcccc 7021 cctgacgagc atcacaaaaa tcgacgctca gtcagaggt ggcgaaaccc gacaggacta 7081 taaagatacc aggcgtttcc ccctggaagc tccctcgtgc gctctcctgt tccgaccctg 7141 ccgcttaccg gatacctgtc cgcctttctc ccttcgggaa gcgtggcgct ttctcatagc 7201 tcacgctgta ggtatctcag ttcggtgtag tcgttcgct ccaagctggg ctgtgtgcac 7261 gaaccccccg ttcagcccga ccgctgcgcc ttatccggta actatcgtct tgagtccaac 7321 ccggtaagac acgacttatc gccactggca gcagccactg gtaacaggat tagcagagcg 7381 aggtatgtag gcggtgctac agagttcttg aagtggtggc ctaactacgg ctacactaga
```

```
7441 agaacagtat tggtatctg cgctctgctg aagccagtta ccttcggaaa aagagttggt 7501 agctcttgat ccggcaaaca aaccaccgct ggtagcggtg gttttttttgt ttgcaagcag 7561 cagattacgc gcagaaaaaa aggatctcaa gaagatcctt tgatcttttc tacggggtct 7621 gacgctcagt ggaacgaaaa ctcacgttaa gggattttgg tcatgagatt atcaaaaagg 7681 atcttcacct agatcctttt aaattaaaaa tgaagtttta aatcaatcta agtatatat 7741 gagtaaactt ggtctgacag ttaccaatgc ttaatcagtg aggcacctat ctcagcgatc 7801 tgtctatttc gttcatccat agttgcctga ctccccgtcg tgtagataac tacgatacgg 7861 gagggcttac catctggccc cagtgctgca atgataccgc gagacccacg ctcaccggct 7921 ccagatttat cagcaataaa ccagccagcc ggaagggccg agcgcagaag tggtcctgca 7981 actttatccg cctccatcca gtctattaat tgttgccggg aagctagagt aagtagttcg 8041 ccagttaata gtttgcgcaa cgttgttgcc attgctacag gcatcgtggt gtcacgctcg 8101 tcgtttggta tggcttcatt cagctccggt tcccaacgat caaggcgagt tacatgatcc 8161 cccatgttgt gcaaaaaagc ggttagctcc ttcggtcctc cgatcgttgt cagaagtaag 8221 ttggccgcag tgttatcact catggttatg gcagcactgc ataattctct tactgtcatg 8281 ccatccgtaa gatgcttttc tgtgactggt gagtactcaa ccaagtcatt ctgagaatag 8341 tgtatgcggc gaccgagttg ctcttgcccg gcgtcaatac gggataatac cgcgccacat 8401 agcagaactt taaaagtgct catcattgga aaacgttctt cggggcgaaa actctcaagg 8461 atcttaccgc tgttgagatc cagttcgatg taacccactc gtgcacccaa ctgatcttca 8521 gcatctttta ctttcaccag cgtttctggg tgagcaaaaa caggaaggca aaatgccgca 8581 aaaaagggaa taagggcgac acggaaatgt tgaatactca tactcttcct ttttcaatat 8641 tattgaagca tttatcaggg ttattgtctc atgagcggat acatatttga atgtatttag 8701 aaaaataaac aaatagggggt tccgcgcaca tttccccgaa aagtgccacc tgac
```

VHH1-BBz CAR DNA (SEQ ID NO: 33) (as shown in FIG. 19):

ATGGCCTTACCAGTGACCGCCTTGCTCCTGCCGCTGGCCTTGCTGCTCC

ACGCCGCCAGGCCGGGATCCGCGGCCCAGGCGGCCCAGGTGCAGCTGCA

GGAGTCTGGGGGAGGATTGGTGCAGCCTGGGGGCTCGACAAGACTCTCC

TGTGTATCGTCCCGCACCTTTAGTTATTATGACATGGGCTGGTTCCGCC

AGGCTCCAGGGAAGGAGCGTGAGTTCGTAGCACTGCTTAGTTGGAATGG

GGAAAATGCAGAGTATTCAGACTCCGTGATGGGCCGTTTCACCGTCTCC

CGAGGGAATACCCAGAATTCGGTGAATCTGCAAATGAACAACCTGAAAC

CTGAGGACACGGGCATCTATTACTGCGCAGTGACGCACGGTGGAGCGCG

GTCGGTTCGTTCCTGGGGCCAGGGGACCCAGGTCACCGTCTCCTCAGCG

GCCGCCACTAGTGGCCAGGCCGGCCAGTCCGGAGAGTCTAAGTACGCC

CTCCCTGCCCTCCTTGCCCAGCTAGCTACATCTGGGCGCCCTTGGCCGG

GACTTGTGGGGTCCTTCTCCTGTCACTGGTTATCACCCTTTACTGCAAA

CGGGGCAGAAAGAAACTCCTGTATATATTCAAACAACCATTTATGAGAC

CAGTACAAACTACTCAAGAGGAAGATGGCTGTAGCTGCCGATTTCCAGA

AGAAGAAGAAGGAGGATGTGAACTGAGAGTGAAGTTCAGCAGGAGCGCA

GACGCCCCCGCGTACAAGCAGGGCCAGAACCAGCTCTATAACGAGCTCA

ATCTAGGACGAAGAGAGGAGTACGATGTTTTGGACAAGAGACGTGGCCG

GGACCCTGAGATGGGGGGAAAGCCGAGAAGGAAGAACCCTCAGGAAGGC

CTGTACAATGAACTGCAGAAAGATAAGATGGCGGAGGCCTACAGTGAGA

TTGGGATGAAAGGCGAGCGCCGGAGGGGCAAGGGGCACGATGGCCTTTA

CCAGGGTCTCAGTACAGCCACCAAGGACACCTACGACGCCCTTCACATG

CAGGCCCTGCCCCCTCGC

VHH1-BBz CAR protein (SEQ ID NO: 34) (as shown in FIG. 19):

MALPVTALLLPLALLLHAARPGSAAQAA<u>QVQLQESGGGLVQPGGSTRLS</u>

<u>CVSSRTFSYYDMGWFRQAPGKEREFVALLSWNGENAEYSDSVMGRFTVS</u>

<u>RGNTQNSVNLQMNNLKPEDTGIYYCAVTHGGARSVRSWGQGTQVTVSSA</u>

AA*TSGQAGQSGESKYGPPCPPCPAS*<u>YIWAPLAGTCGVLLLSLVITLYCK</u>

<u>RGRKKLLYIFKQPFMRPVQTTQEEDGCSCRFPEEEEGGCELRVKESRSA</u>

-continued

<u>DAPAYKQGQNQLYNELNLGRREEYDVLDKRRGRDPEMGGKPRRKNPQEG</u>

<u>LYNELQKDKMAEAYSEIGMKGERRRGKGHDGLYQGLSTATKDTYDALHM</u>

<u>QALPPR</u>

Bold is signal peptide (SEQ ID NO: 18)
Underlined is VHH1 (SEQ ID NO: 2)
Italicized is IgG4mh (SEQ ID NO: 20)
Dotted underlined is CD8 transmembrane (SEQ ID NO: 21)
Double underlined is 4-1BB and CD3z (SEQ ID NO: 22)

VHH1-28BBz CAR DNA (SEQ ID NO: 35) (as shown in FIG. 19):

ATGGCCTTACCAGTGACCGCCTTGCTCCTGCCGCTGGCCTTGCTGCTCC

ACGCCGCCAGGCCGGGATCCGCGGCCCAGGCGGCCCAGGTGCAGCTGCA

GGAGTCTGGGGGAGGATTGGTGCAGCCTGGGGGCTCGACAAGACTCTCC

TGTGTATCGTCCCGCACCTTTAGTTATTATGACATGGGCTGGTTCCGCC

AGGCTCCAGGGAAGGAGCGTGAGTTCGTAGCACTGCTTAGTTGGAATGG

GGAAAATGCAGAGTATTCAGACTCCGTGATGGGCCGTTTCACCGTCTCC

CGAGGGAATACCCAGAATTCGGTGAATCTGCAAATGAACAACCTGAAAC

CTGAGGACACGGGCATCTATTACTGCGCAGTGACGCACGGTGGAGCGCG

GTCGGTTCGTTCCTGGGGCCAGGGGACCCAGGTCACCGTCTCCTCAGCG

GCCGCCACTAGTTCCGGAGAGAGCAAGTACGGCCCTCCCTGCCCCCCTT

GCCCTGATATCTTTTGGGTGCTGGTGGTGGTTGGTGGAGTCCTGGCTTG

CTATAGCTTGCTAGTAACAGTGGCCTTTATTATTTTCTGGGTGAGGAGT

AAGAGGAGCAGGCTCCTGCACAGTGACTACATGAACATGACTCCCCGCC

GCCCCGGGCCCACCCGCAAGCATTACCAGCCCTATGCCCCACCACGCGA

CTTCGCAGCCTATCGCTCCGCTAGCAAACGGGGCAGAAAGAAACTCCTG

TATATATTCAAACAACCATTTATGAGACCAGTACAAACTACTCAAGAGG

AAGATGGCTGTAGCTGCCGATTTCAGAAGAAGAAGAAGGAGGATGTGA

ACTGAGAGTGAAGTTCAGCAGGAGCGCAGACGCCCCCGCGTACAAGCAG

GGCCAGAACCAGCTCTATAACGAGCTCAATCTAGGACGAAGAGAGGAGT

ACGATGTTTTGGACAAGAGACGTGGCCGGGACCCTGAGATGGGGGGAAA

GCCGAGAAGGAAGAACCCTCAGGAAGGCCTGTACAATGAACTGCAGAAA

GATAAGATGGCGGAGGCCTACAGTGAGATTGGGATGAAAGGCGAGCGCC

GGAGGGGCAAGGGGCACGATGGCCTTTACCAGGGTCTCAGTACAGCCAC

CAAGGACACCTACGACGCCCTTCACATGCAGGCCCTGCCCCCTCGC

VHH1-28BBz CAR protein (SEQ ID NO: 36):

MALPVTALLLLPLALLLHAARPGSAAQAAQVQLQESGGGLVQPGGSTRLS

CVSSRTFSYYDMGWFRQAPGKEREFVALLSWNGENAEYSDSVMGRFTVS

RGNTQNSVNLQMNNLKPEDTGIYYCAVTHGGARSVRSWGQGTQVTVSSA

AA*TSSGESKYGPPCPPCPDI*

FWVLVVVGGVLACYSLLVTVAFIIFWVRSKRSRLLHSDYMNMTPRRP

GPTRKHYQPYAPPRDFAAYRSA<u>SKRGRKKLLYIFKQPFMRPVQTTQEED</u>

-continued

<u>GCSCRFPEEEEGGCELRVKFSRSADAPAYKQGQNQLYNELNLGRREEYD</u>

<u>VLDKRRGRDPEMGGKPRRKNPQEGLYNELQKDKMAEAYSEIGMKGERRR</u>

<u>GKGHDGLYQGLSTATKDTYDALHMQALPPR</u>

Bold is signal peptide (SEQ ID NO: 18)
Underlined is VHH1 (SEQ ID NO: 2)
Italicized is modified IgG4h (SEQ ID NO: 38)
Dashed underlined is CD28 transmembrane and CD28 intracellular domain (SEQ ID NO: 37)
Double underlined is 4-1BB and CD3z (SEQ ID NO: 22)

Example 1: Generating Nanobodies that Preferentially Bind Tumor Cells and Empower CAR T Cells to Kill the Tumor Cells While remarkable success has been achieved via using CAR T cells targeting CD19 to cure lymphocytic leukemia, this process remains a challenge for treating other types of cancers. Several factors hinder the expansion of CAR T approach. First, it is often difficult to determine which surface proteins of tumor cells serve as the effective targets to elicit CAR T cell antitumor activity without long-term and laborious studies. Second, lack of detailed information of mAbs against tumor cell surface proteins seriously hampers development of CAR T therapy. Third, many mAbs are not compatible with the CAR T system to kill cancer cells, which requires proper epitope binding, decent avidity and optimized immunological synapse formation. Fourth, certain epitopes such as clefts on the surface proteins cannot be reached by conventional antibodies with heavy and light chains, but could be recognized by single domain nanobodies from camelid animals.

To circumvent the above limitations, a method was developed herein that quickly isolates nanobodies that preferentially bind tumor cells in vitro as well as enables the cognate CAR T cells to induce tumor regression in vivo. With the isolation of such antibodies, the matching antigens are identified via cell-based screening of human cell surface proteins-encoding cDNAs. This technology is termed Sequentially Tumor-selected Antibody and antigen Retrieval (STAR) system. The advantage of such a system is that the isolated antibodies are already shown to bind the antigens preferentially expressed in a tumor or cell type-specific manner, and at the same time, the monoclonal nanobodies are already capable of redirecting the CAR T cells to the tumor site in vivo. Therefore, this system significantly expedites the pace to identify the antibodies and their targets to extend CAR T application in various types of cancers.

Figure 1B:
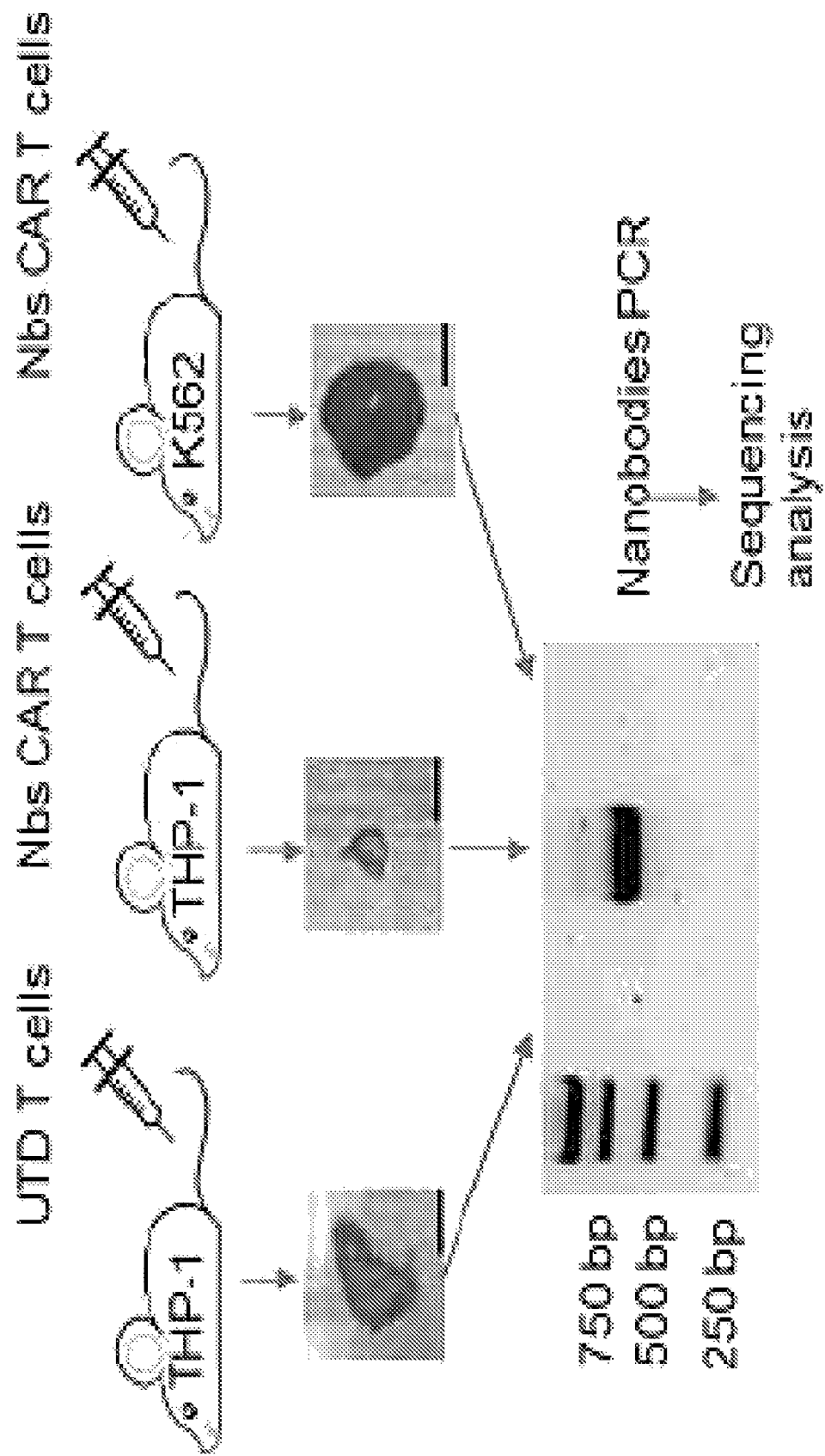

To identify such a nanobody that specifically targets acute myeloid leukemia (AML) cells, but not T cells, a nanobody phage-display library was constructed with ~$10^9$ clones from llamas immunized with THP-1 cells, a human AML cell line (FIG. 1A). The library was then used for panning with THP-1 cells in vitro, with negative absorption of Jurkat cells (a human acute T cell leukemia) to exclude the nanobodies that recognized T cells, and with negative absorption of K562 cells (a human chronic myelogenous leukemia (CML) cell line) to stringently select the AML specific nanobodies. The resultant phage sub-library (sub-lib) contained the nanobodies that preferentially bind the cell surface antigens of THP-1 with high affinity.

Example 2: Identifying Nanobodies that are Capable of Redirecting CAR T Cells to the THP-1 Tumor In Vivo The above isolated nanobodies preferentially bound the THP-1 cell surface proteins, however, not all of these nanobodies were capable of empowering CAR T lymphocytes with antitumor activities, which requires effective antibody-antigen interaction and appropriate immunological synapse. To address these issues and screen the active Nbs, the nanobodies were fused to CAR constructs to establish Nb-lib CAR T cells via lentivirus transduction, followed by treating the NSG mice bearing THP-1 tumor or K562 tumor burdens, untranduced (UTD) T cells as a control group (FIG. 1). The CAR construct was composed of a signal peptide (SP), nanobody fragment, IgG4 mutation (IgG4m) hinge, CD8 transmembrane domain (TM), 4-1BB and CD3zeta domain, as shown in FIG. 2A.

Figure 1C:
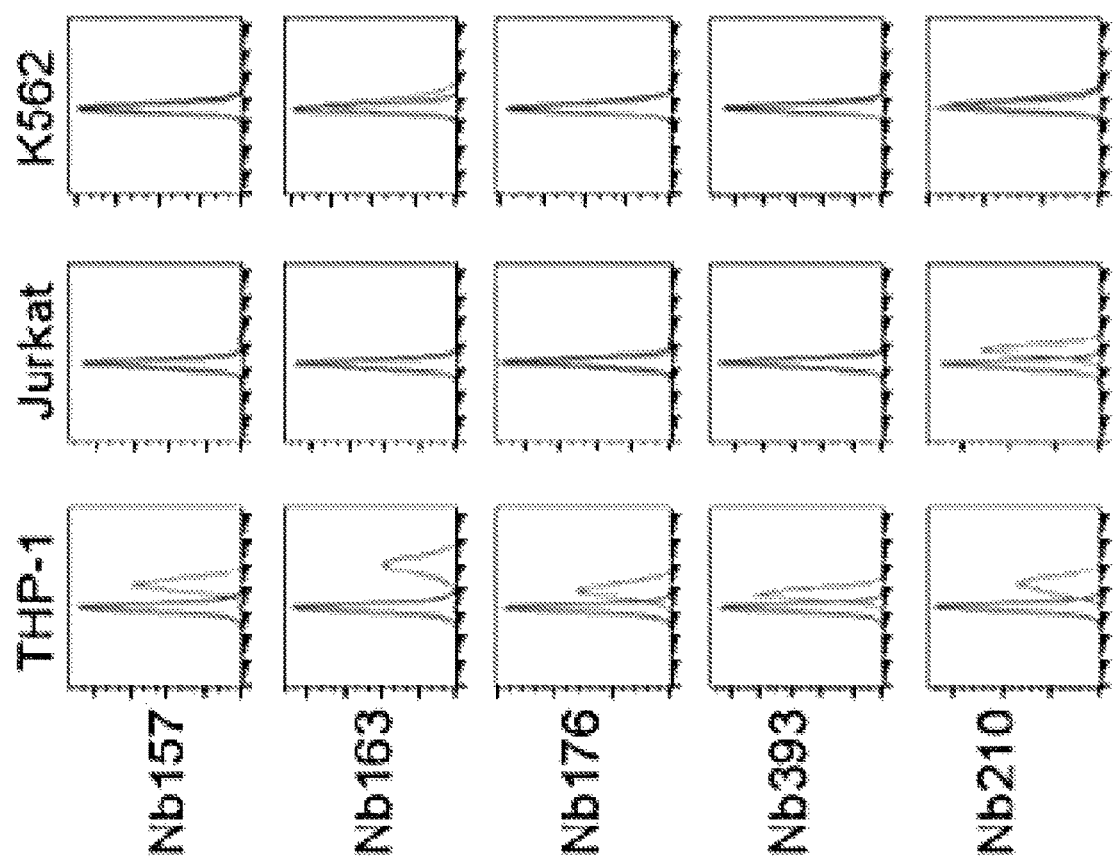
Figure 7:
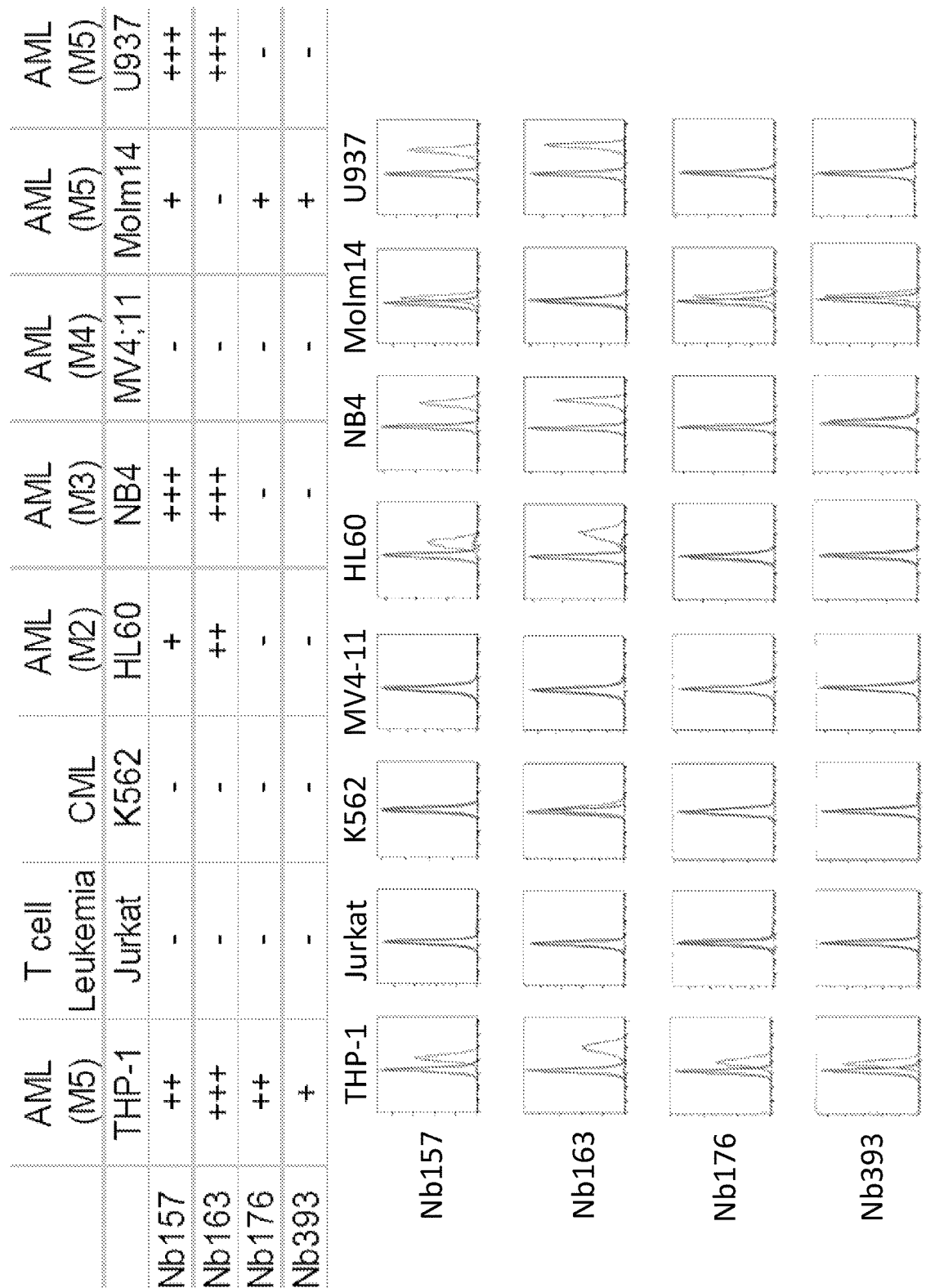
FIG. 7 is series of a table and graphs depicting the affinity test of VHHs against variant of AML cell lines and patient derived AMLs. The four THP-1 specific Nbs were tested for their recognition to other AML cell lines. + was <0.5 log shift, ++ was <1.0 log shift, +++ was <1.5 log shift, − was no binding.

It was hypothesized that the most suitable nanobodies that redirected the cognate CAR T cells to eradicate the tumor would be enriched along with the activation and proliferation of T cells upon encountering the targets. Moreover, the in vivo selection model could reduce and clean the noise signals of the nanobodies from Nb-lib CAR T as the non-tumor-specific Nb-lib CAR T cells may be distributed to and/or absorbed by various mouse tissues. Therefore, desirable nanobodies would guide the CAR T cells to the THP-1 tumor, but not K562 tumor, in vivo. To do this, 14 days post T cells infusion, the UTD T cells-treated THP-1 tumor, Nb-lib CAR T cells-treated THP-1 tumor, and the Nb-lib CAR T cells-treated K562 tumor tissues were collected to decode the Nbs sequences that were integrated into the genome of the CAR T cells infiltrated in the tumors. PCR results indicated that Nb sequences were only retrieved from Nb-lib CAR T cells-treated THP-1 tumor (FIG. 1B, lane 2), but not from either K562 tumor or UTD-treated THP-1 tumor (FIG. 1). About 400 individual clones from amplified nanobodies (FIG. 1B, lane 2) were sequenced. Among the most enriched five unique Nbs, four of them, i.e. Nb157, Nb163, Nb176 and Nb393, specifically bound THP-1 cells, but not Jurkat or K562 cells, as shown by flow cytometry analysis (FIG. 1C). Moreover, Nb157 and Nb163 also bound other AML cell lines like HL60, NB4, and U937 (FIG. 7). Together, these results indicated that the STAR system was capable of enriching and isolating multiple nanobodies that specifically bound AML cells.

Figure 2C:
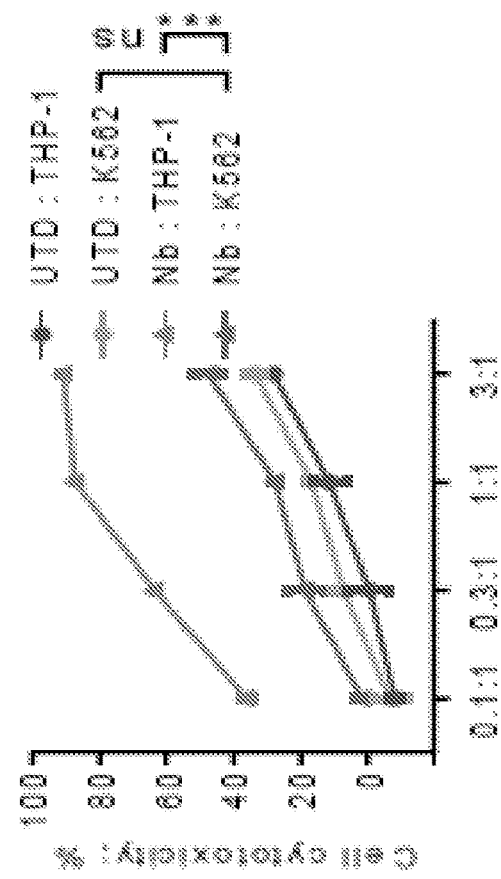
Figure 2B:
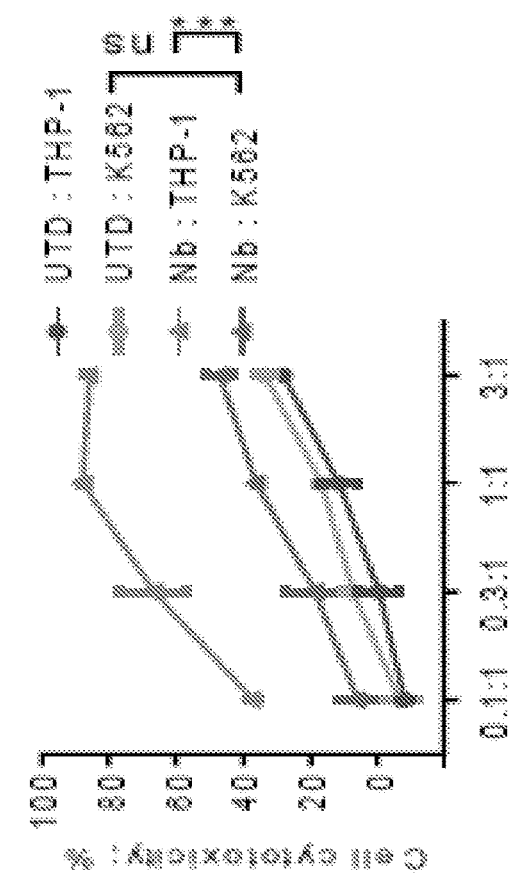
Figure 8A:
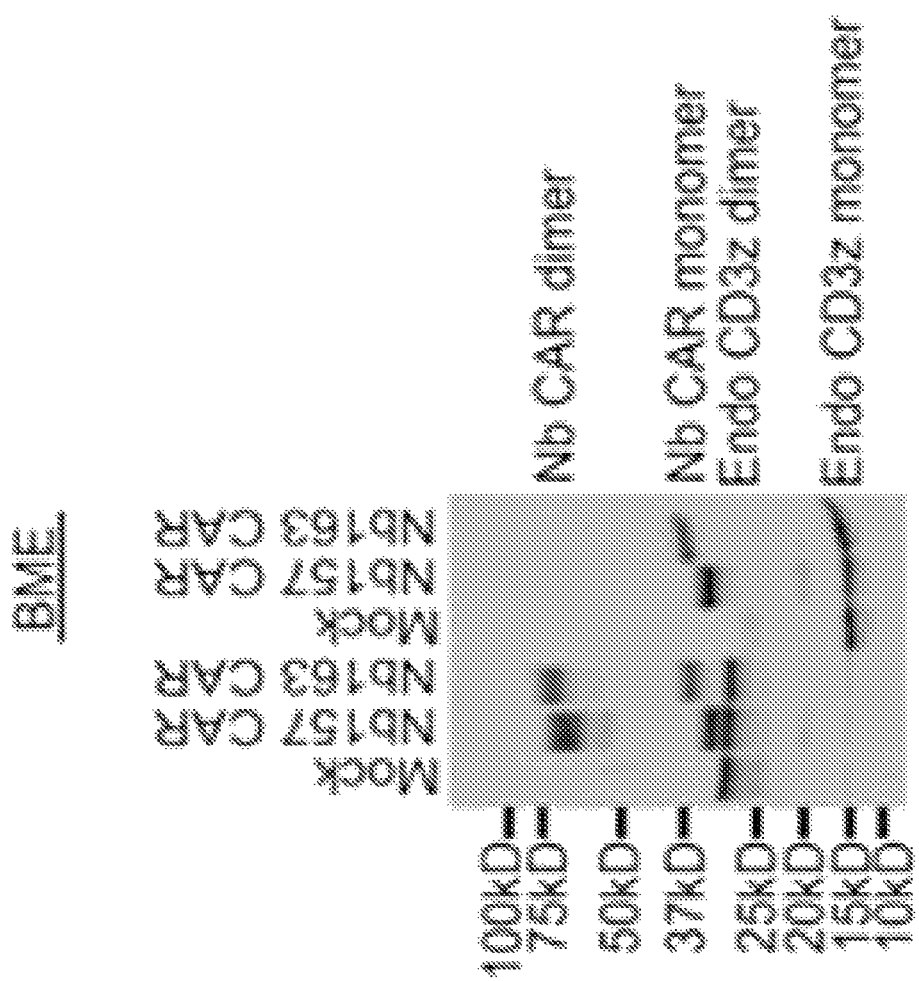
FIGS. 8A-8C are series of an image and graphs depicting the expression of the Nb CARs protein in human primary T cells.
Figure 8B:
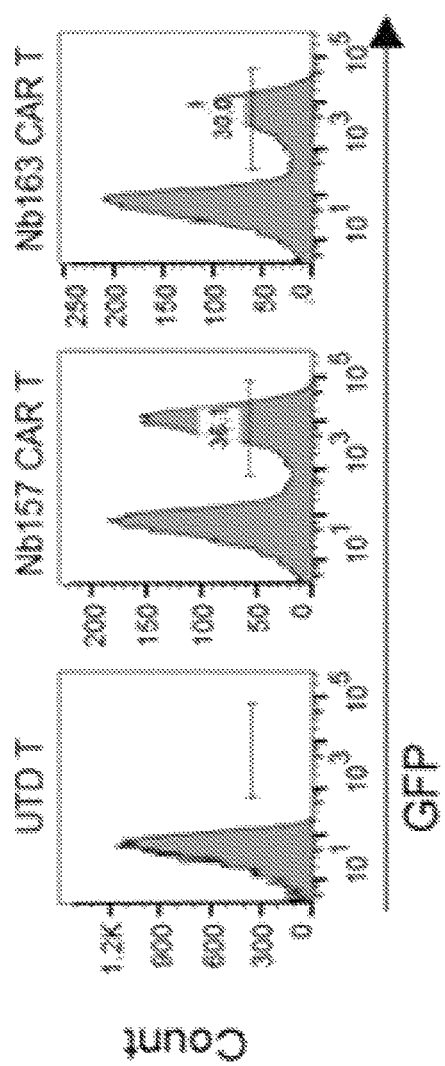

Example 3: All the Nanobodies Isolated by the STAR System Redirected CAR T Cells to Potently Kill the AML Cells In Vitro Based on the design of STAR system, most of the identified nanobodies should be able to guide CAR T cells to kill target tumor cells. To test this, individual CARs (FIG. 2A) were transduced and expressed into activated primary human T cells (FIGS. 8A-8B). In vitro cytotoxicity assays showed that Nb157 CAR T cells potently and specifically killed THP-1 AML cells, but not as much in the K562 CML cells or Jurkat T leukemia cells, in a CAR T effector to target cells ratio-dependent manner (FIGS. 2B and 2D). As a control, UTD T cells did not cause obvious cytotoxicity (FIGS. 2B-2D). Similarly, Nb163, Nb176, Nb393 CAR T cells also killed THP-1 AML specifically, but not K562 CML cells (FIG. 2C and FIGS. 9A-9B). To determine if the Nb CAR T cells can also kill other Nb-recognizing AML cells, we incubated Nb157 CAR T with HL60 cell, another human AML cell line, and found that they also caused specific cytotoxicity against the AML cells, but not the Jurkat cells (FIG. 2D).

Figure 2F:
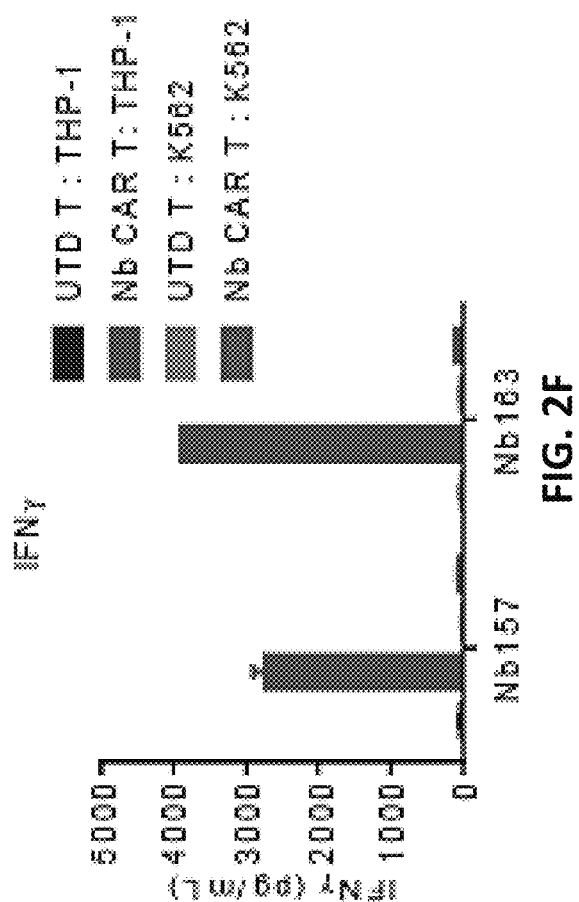
Figure 2G:
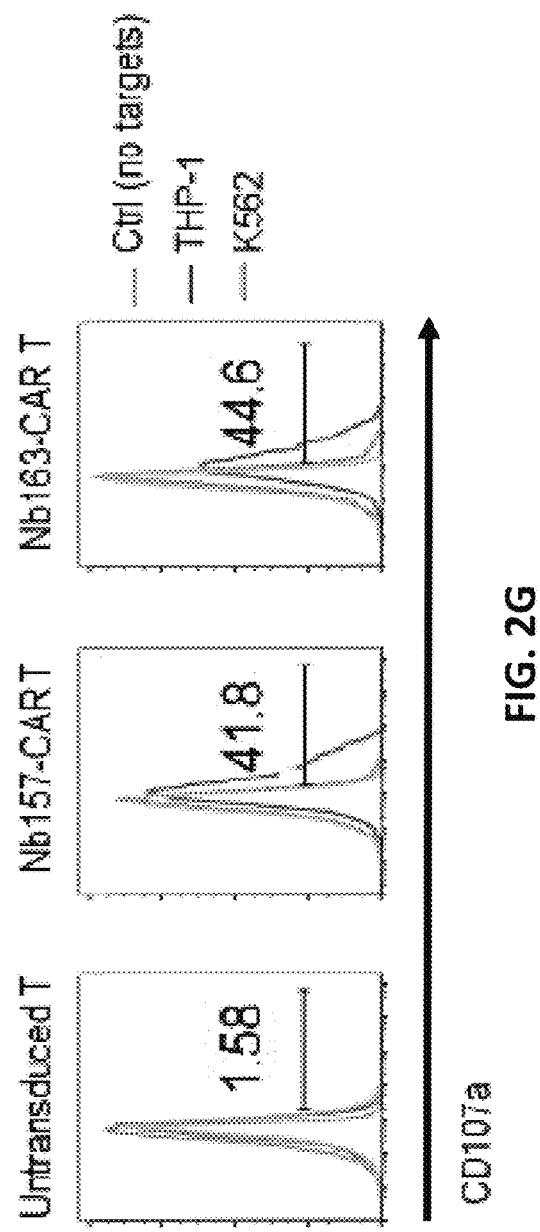
Figure 2H:
Figure 2I:
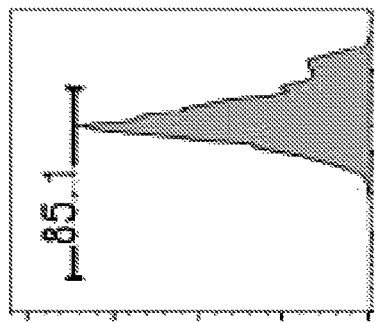
Figure 2J:
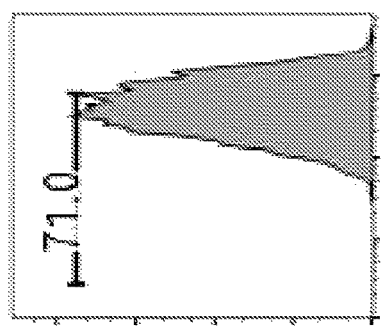
Figure 2K:
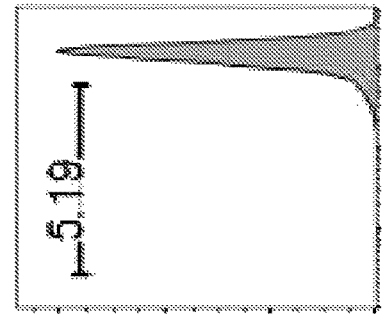
Figure 8C:
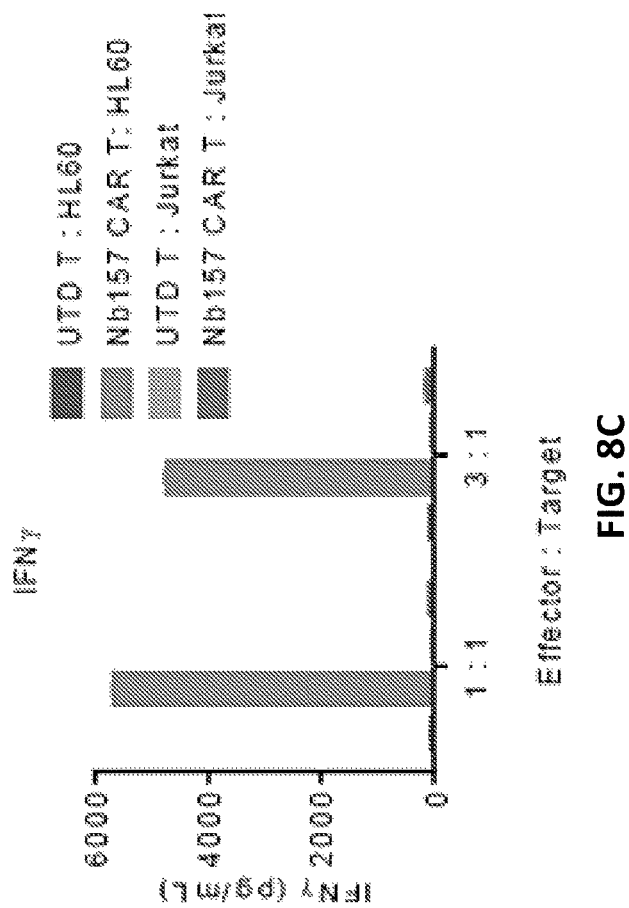

Activated T cells, upon encountering the targets, release various cytokines including TNFα and IFNγ, degranulate to deliver cytolytic proteins along with the mobilization of CD107a to the cell surface, and enhance proliferation. To determine if the target AML cells can specifically activate the Nb CAR T cells, THP-1 cells were co-incubated with either Nb157 or Nb163 CAR T. THP-1 cells, but not control K562 cells, stimulated Nb157 and Nb163 CAR T cells to release cytokines including TNFα and IFNγ (FIGS. 2E-2F). As a control, neither target THP-1 cells nor K562 cells stimulated cytokine release from UTD T cells (FIGS. 2E-2F). A similar increase in cytokine release was detected in the co-incubation of HL60 with Nb157 CAR T cells (FIG. 8C). Moreover, THP-1 cells, but not K562 cells, specifically induced the CAR T degranulation as shown by increase in cell surface CD107a (FIG. 2G). Further, THP-1 cells, but not K562 cells, specifically induced proliferation of the Nb157 and Nb163 CAR T cells (FIGS. 2H, 2I). Together, these findings demonstrated that Nb157 and Nb163 CAR T cells were specifically activated by target THP-1 AML cells, leading to enhanced proliferation, cytokine release and degranulation to kill the target AML cells.

Example 4: Nb CAR T Cells Potently Induced the AML Tumor Regression In Vivo

Figures 3A, 3B:
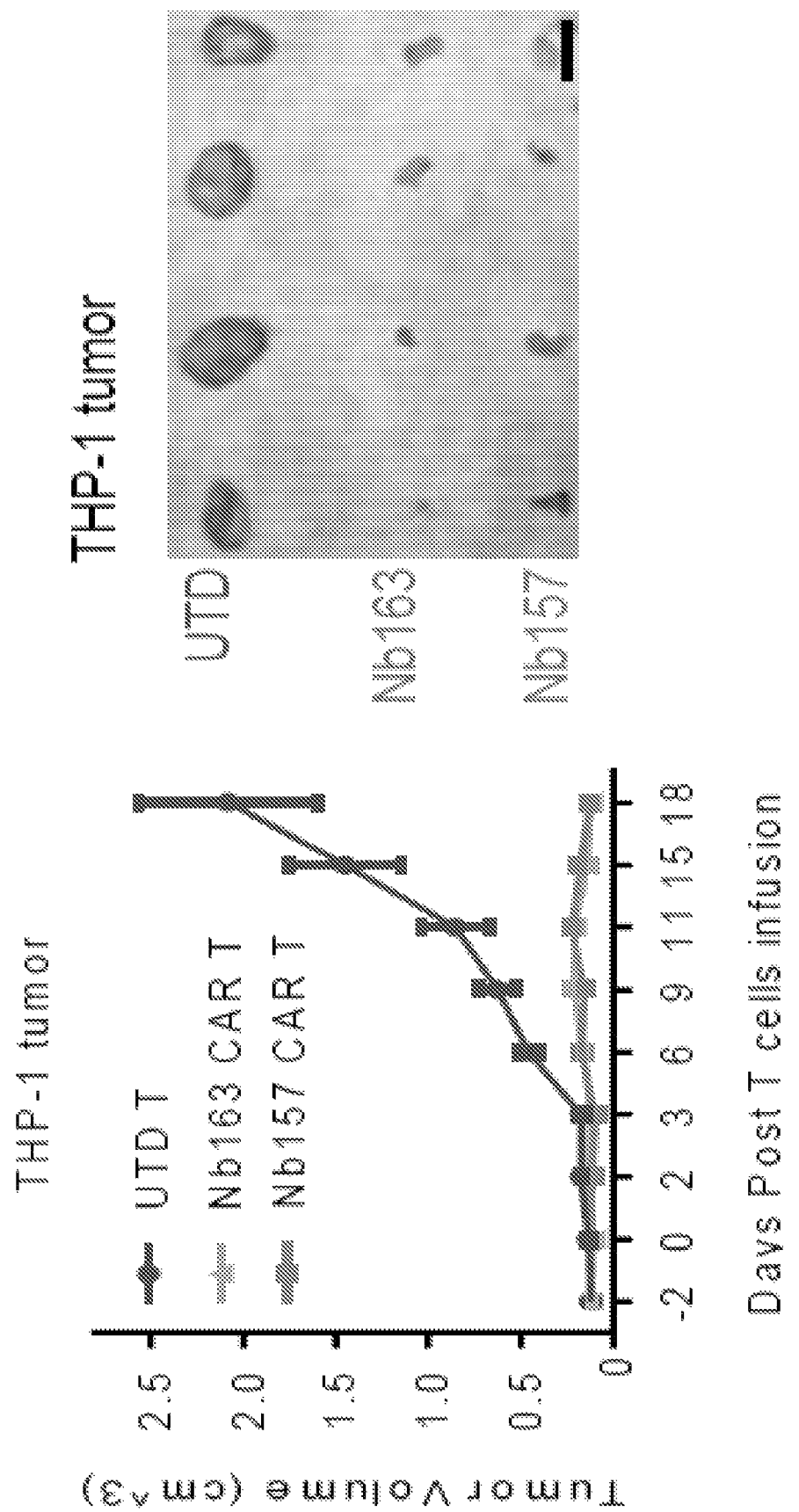
FIGS. 3A-3F are series of images and graphs demonstrating that nanobody-adapted CAR T cells potently suppress AML tumors in vivo.
Figures 3C, 3D:
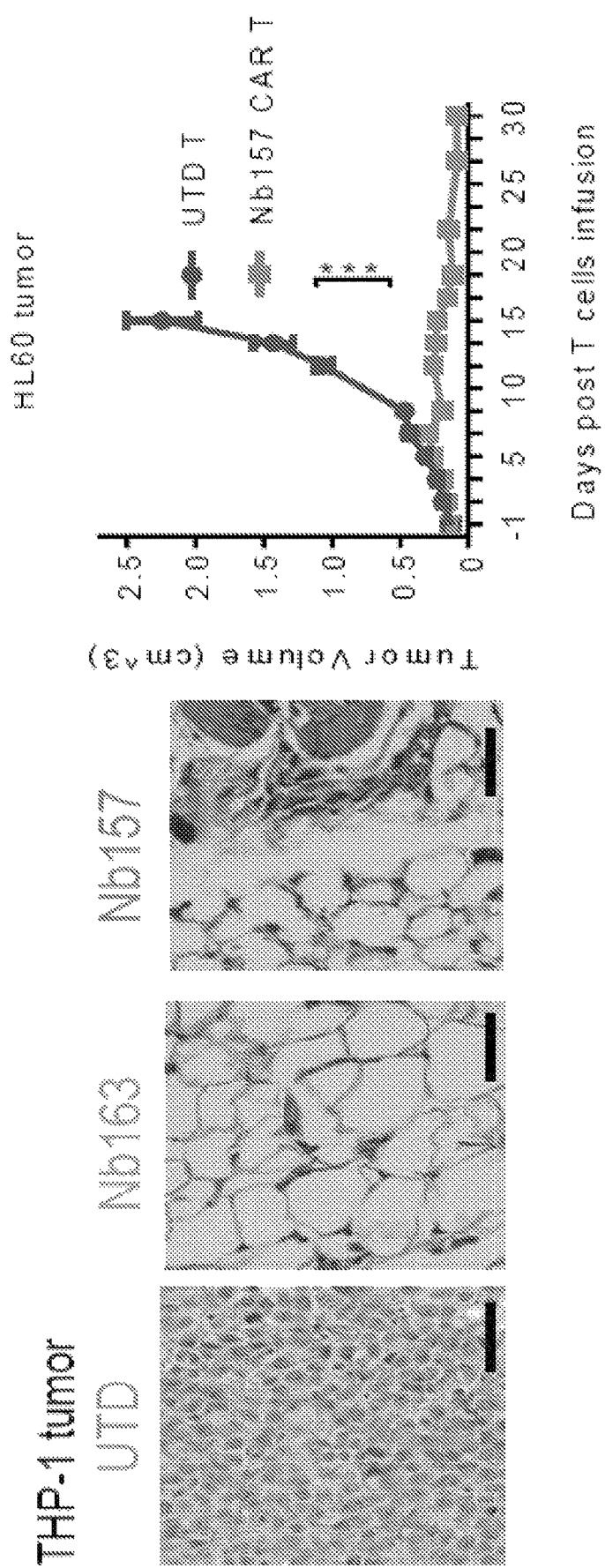

To determine whether the Nb CAR T cells suppressed the AML tumors in vivo, THP-1 cells were transplanted into NSG mice subcutaneously. When the tumor reached ~150 mm³, Nb157 CAR T, Nb163 CAR T, or control UTD T cells were injected intravenously into the mice. The tumors from the control UTD T-treated mice grew exponentially (FIGS. 3A-3B). Notably, the tumors in the Nb157 or Nb163 CAR T-treated mice failed to grow substantially, and eventually regressed (FIGS. 3A-3B). Histological studies indicated that while the control tumor contained abundant tumor cells (FIG. 3C, UTD), the Nb CAR T cells eradicated the cancer cells, leaving the fibrotic tissues in the site (FIG. 3C).

Figure 3F:
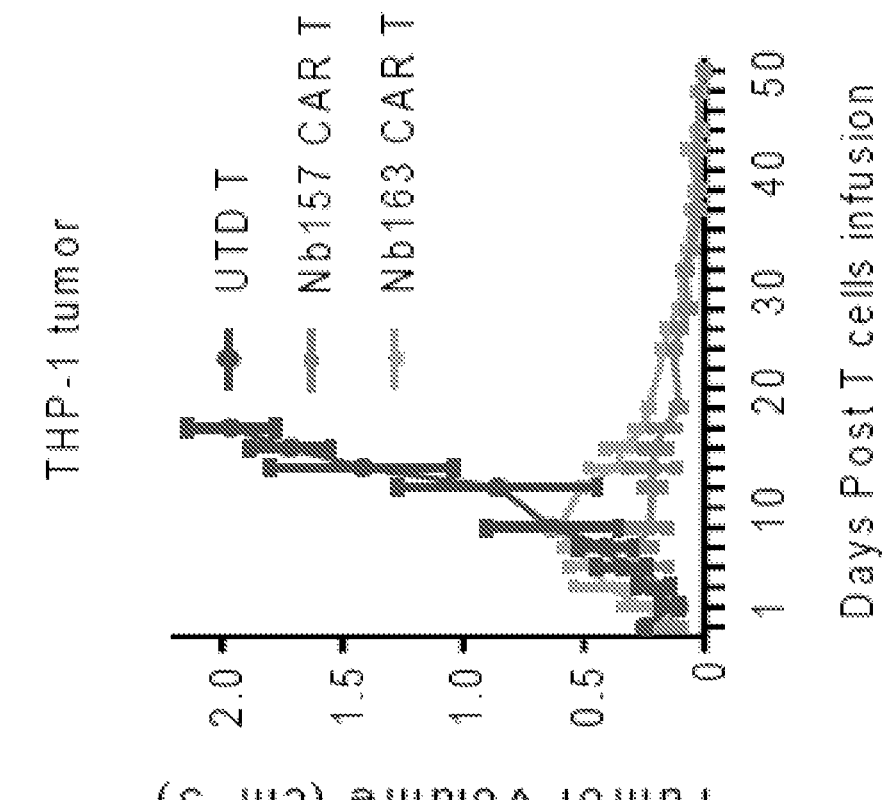
Figure 3E:
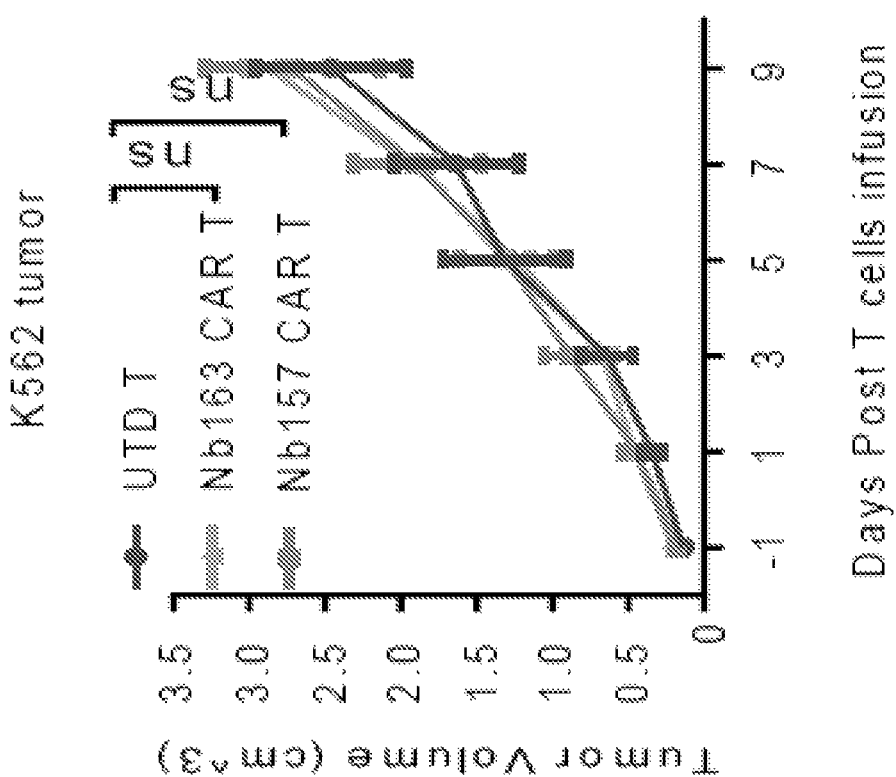

Next, the impact of Nb157 CAR on other AML cells in vivo was examined. HL60 AML cells were transplanted into NSG mice to form tumors, followed by treatment of either Nb157 CAR or UTD T cells. Compared to the UTD T cell group, Nb157 CAR T cells exhibited significant antitumor efficacy against HL60 tumor burden in vivo (FIG. 3D). As a control, both Nb157 and Nb163 CAR T cells failed to induce the regression of the non-target K562 tumors (FIG. 3E), supporting the specificity of CAR T suppressing tumors. Further, it was determined if long-term maintenance of the CAR T treated mice would show recurrence of the tumors. Low dose of Nb157 or Nb163 CAR T cells showed complete remission of THP-1 tumor without recurrence for a long time (FIG. 3F), supporting the eradication of the tumor in the mice.

Figure 9E:
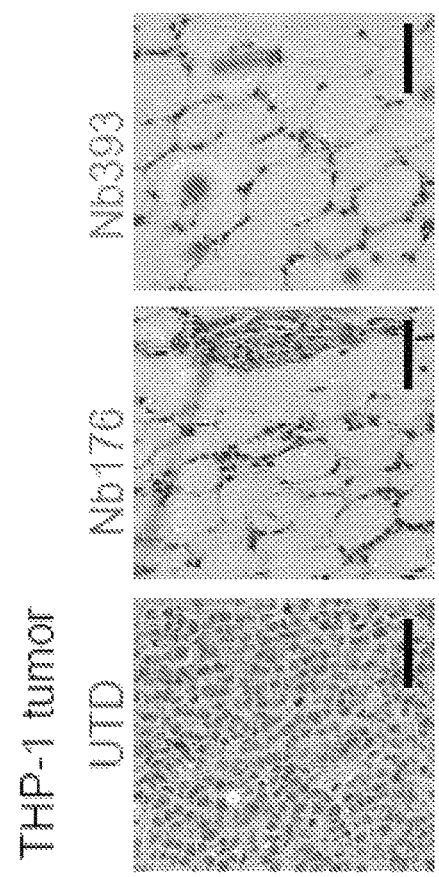
Figure 9D:
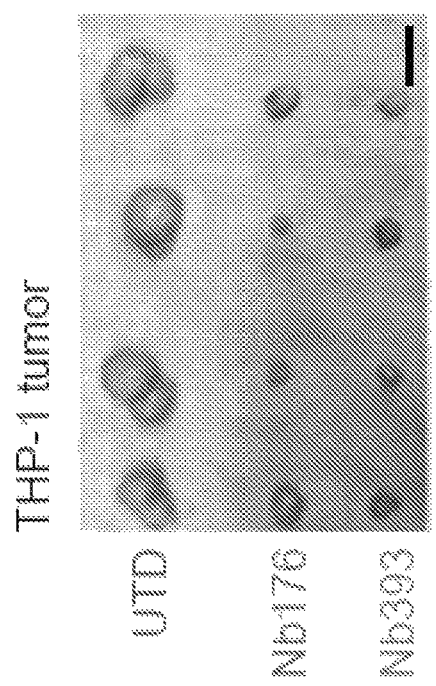
Figure 9G:
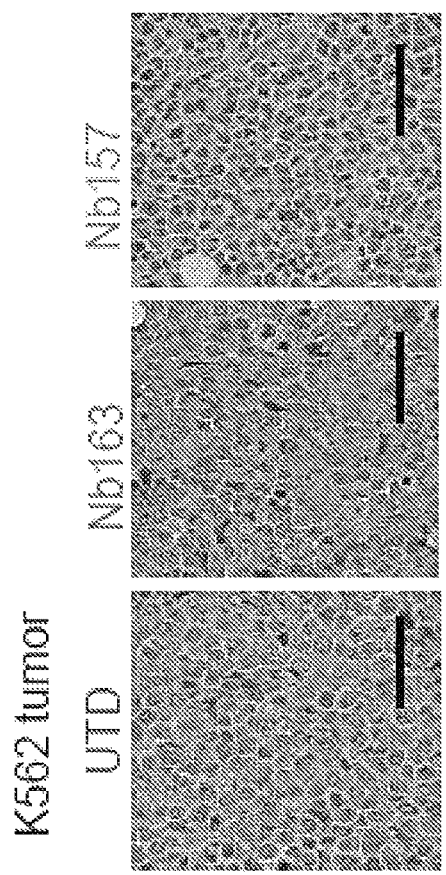
Figure 9F:
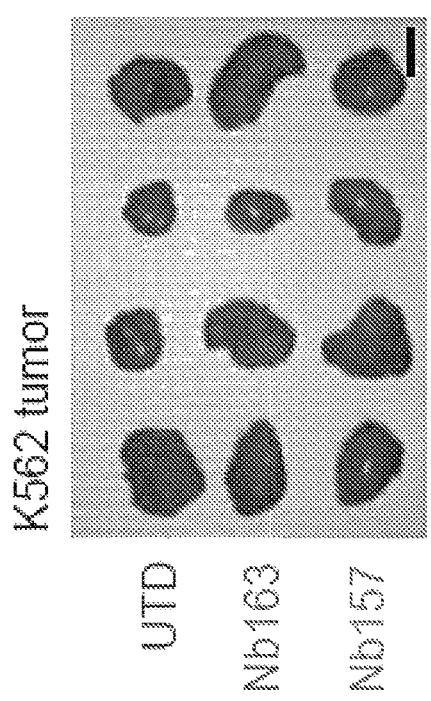

To explore whether the CAR T cells guided by other STAR-isolated nanobodies were capable of killing the AML cells in vitro and in vivo, CAR constructs were generated with either Nb173 or Nb393, two additional THP-1 AML specific nanobodies. The in vitro cytotoxicity assay showed that, similar to Nb157 and Nb163 CAR T cells, Nb173 and Nb393 CAR T cells potently killed THP-1 cells, but not much K562 cells (FIGS. 9A-9B), indicating specific killing by these two types of Nb CAR T cells. Furthermore, in the animal studies Nb176 and Nb393 also performed remarkable antitumor efficacy against THP-1 xenografts (FIGS. 9C-9D). Histological studies also showed that treatment of the Nb CAR T cells, but not UTD T cells, eradiated the tumor cells (FIG. 9E). Collectively, these results demonstrated that all the STAR-isolated nanobodies were capable of empowering the cognate CAR T cells with significant antitumor activities, highlighting an effective approach to isolate the CAR-compatible antibodies to kill cancer cells.

Example 5: Identification of CD13 as a Target to Kill AML Cells by CAR T Cells

Figures 4A, 4B:
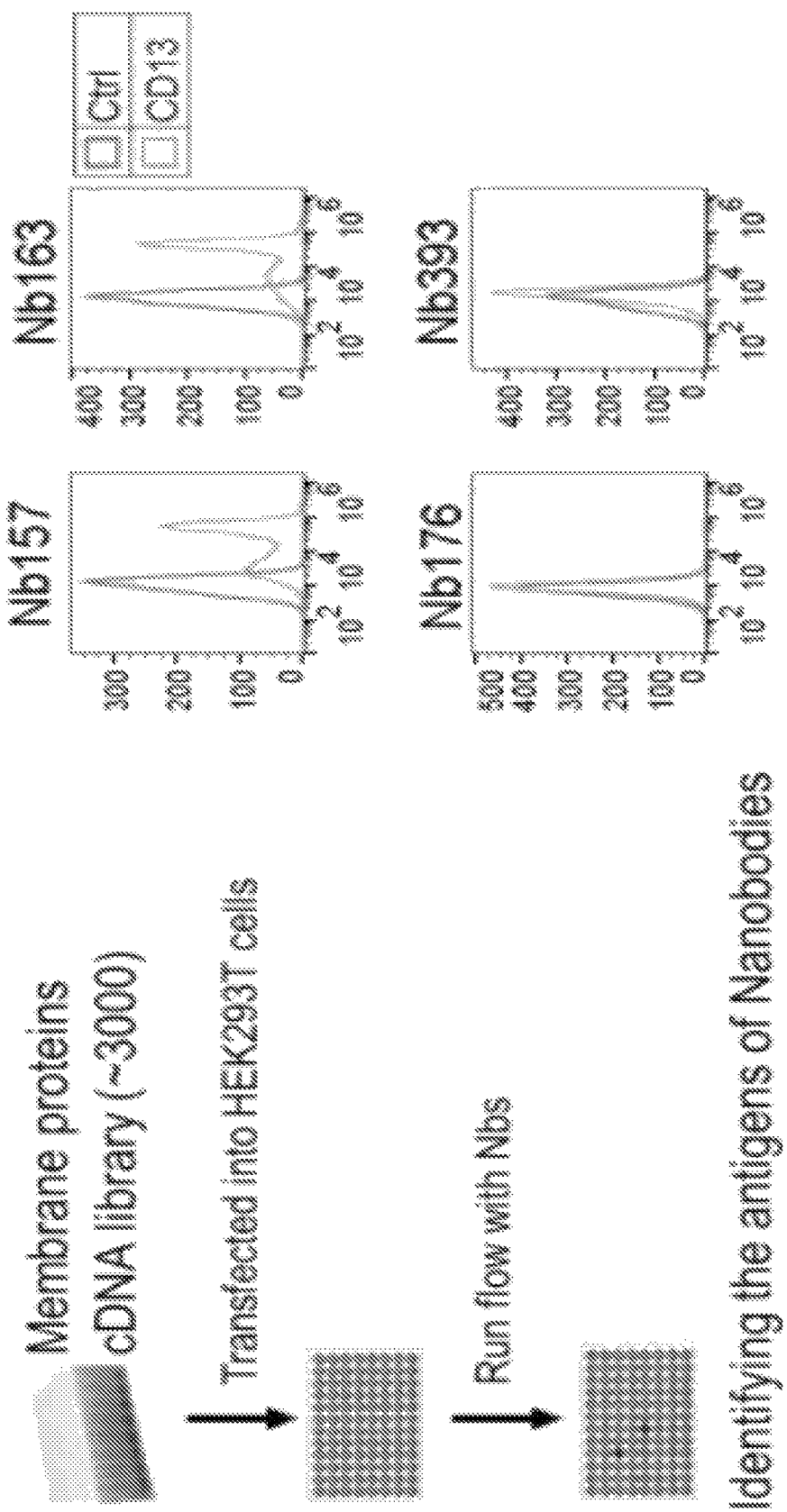

To identify the protein antigens of the isolated nanobodies, about 3000 human cell membrane protein cDNAs were prepared and transfected into HEK293T cells individually, followed by flow cytometry detection with the nanobody-expressing phage and FITC-labeled secondary antibody against phage M13 protein (FIG. 4A). Both Nb157 and Nb163 bound the cells transfected with human full length aminopeptidase N (APN, aka CD13) (FIG. 4B), but Nb176 or Nb393 did not bind CD13 (FIG. 4B). As a confirmation, human CD13 cDNA expression was also shown by western blot (FIG. 4C). CD13 is preferentially expressed in acute myeloid blast cells. It is also expressed moderately in normal myeloid cells and in digestive tract including liver and pancreas; however, knockout of this gene does not cause lethality in mice.

Figure 4F:
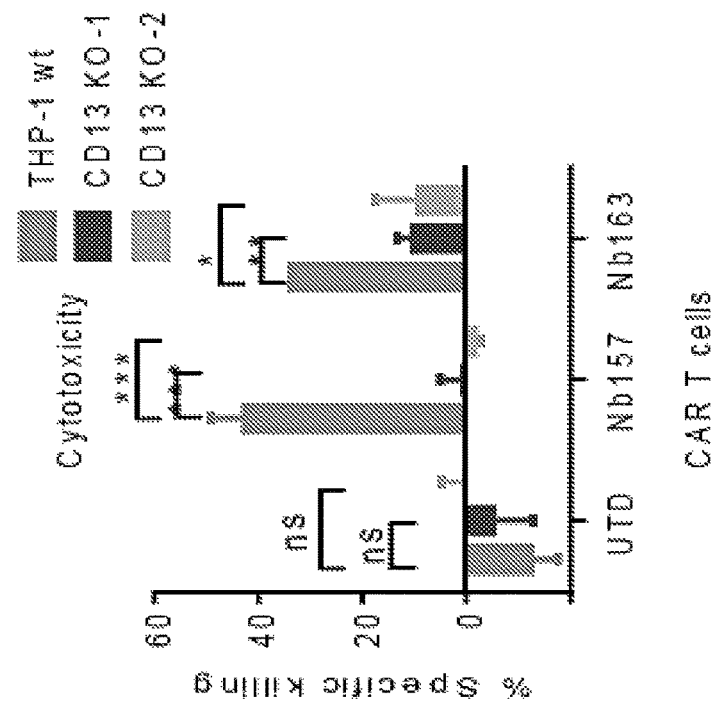
Figure 4E:
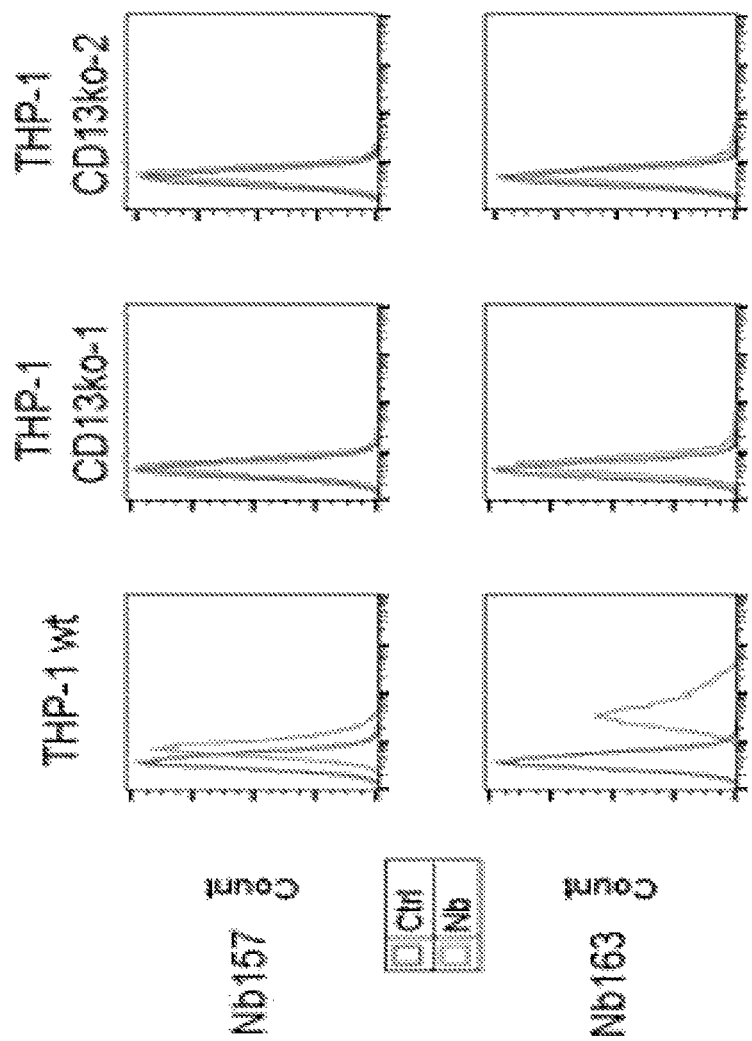

To confirm that Nb157 or Nb163 CAR T cells indeed killed the AML cells by targeting CD13, three individual gRNAs/Cas9 targeting human CD13 were transduced into THP-1 cells by lentivirus, followed by selection and single cell clone expansion. The stable CD13−/− THP-1 cell lines were verified by Western blot (FIG. 4D). Consistent with previous findings herein, flow cytometry analysis showed that CD13 knockout abrogated the binding of Nb157 and Nb163 (FIG. 4E, middle and right panels), as well as the killing of Nb157 CAR T cells to the target cells (FIG. 4F). CD13 knockout diminished the killing of Nb163 to the targets significantly, but cannot abrogated the effect completely, which indicated Nb163 might have off-CD13 antigen on the THP-1 cell surface (FIG. 4F). These results demonstrated that Nb157 CAR T cells performed potent antitumor efficacy against AML by specifically targeting CD13.

Example 6: Nb157 CAR T Cells Exhibit Antitumor Activity in Patient-Derived AML Cells in NSG Mouse Model To further determine whether the Nb157 CAR T cells can also kill the patient-derived AML cells, CD13 expression of the leukemia cells from patient AML2844 was examined. Both Nb157 and Nb163 detected the CD13 expression on the primary AML cells (FIGS. 5A-5B). In vitro cytotoxicity assay also showed that both Nb157 and Nb163 CAR T cells, but not UTD T cells, potently lyzed the patient-derived AML cells (FIGS. 5C-5D). Thereafter, the therapeutic effect of the CAR T cells on the mice with the patient-derived AML cells was examined. To this end, the NSG mice were transplanted with the primary AML cells, followed by treatment with either control UTD or Nb157 CAR T cells. The Kaplan Maier curve showed that the control mice died out 45 days following the primary AML infusion, however, Nb157 CAR T cells infusion significantly prolonged the life of the treated mice (FIG. 5E).

Figure 10B:
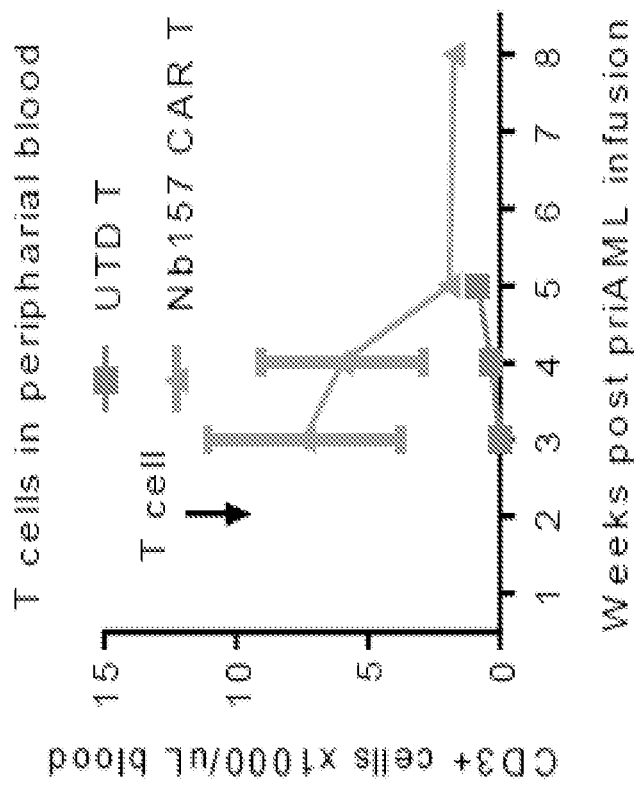
FIGS. 10A-10D are series of graphs illustrating experiments in patient derived AMLs and Nb CAR T cells cells.
Figure 10A:
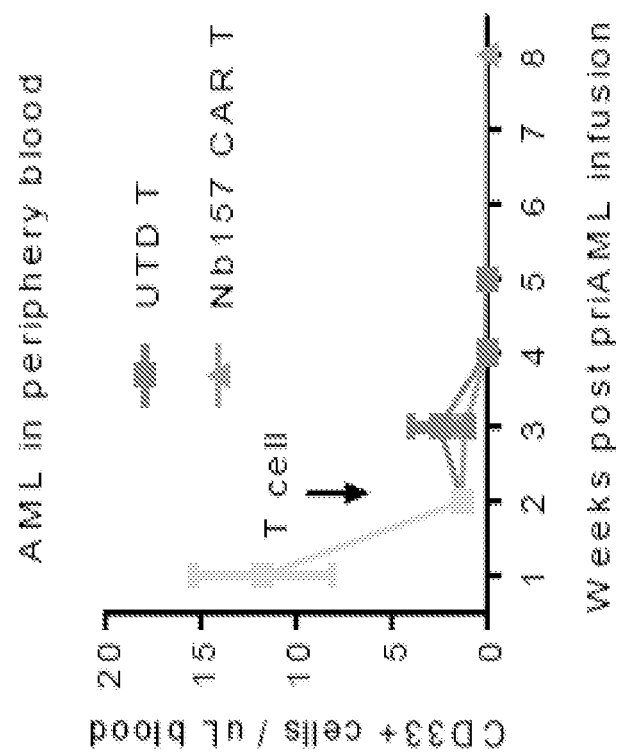

To investigate the dynamics of the leukemia and T cells in the clinical relevant mouse model, changes in AML cells and UTD/CAR T cells in bone marrow, spleen and peripheral blood were monitored. The results showed that in the first week after T cells injection, few CD33+ AML cells, but a large percentage (>90% of hCD45+) of CD3+ T cells were detectable in bone marrow in both UTD and Nb157 CAR T cells groups (FIGS. 5F-5G). Notably, in the second week after the T injection, an increasing number of CD33+ AML appeared in the bone marrow of the UTD T cell-injected recipients (FIG. 5H), but injection of the Nb157 CAR T cells markedly prevented the accumulation of the CD33+ AML cells in the bone marrow (FIG. 5I). Consistently, cell quantification in peripheral blood showed that CD33+ AML cells reduced substantially following injection of Nb157 CAR T cells (FIG. 10A). In the meantime, much more CAR T cells than the control UTD T cells were detectable in the peripheral blood after the T cell infusion (FIG. 10B). However, the CAR T cells in peripheral blood reduced in number at the third week after CAR T infusion, likely reflecting tumor regression and subsiding of the anti-tumor response.

Figure 5K:
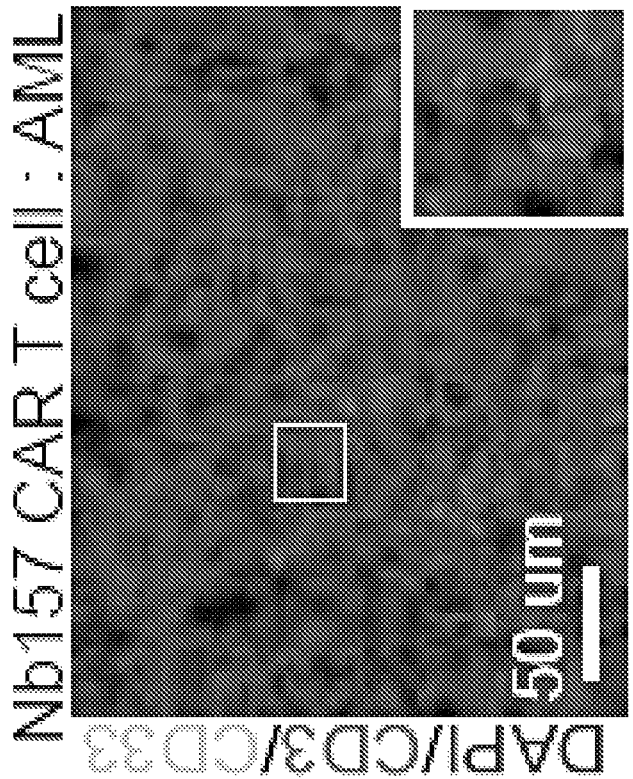
Figure 5J:
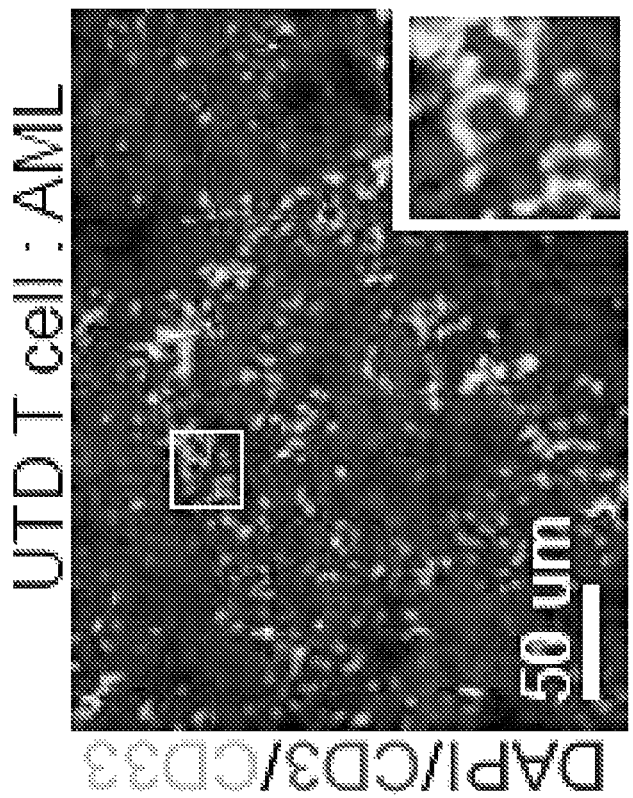
Figures 10C, 10D:
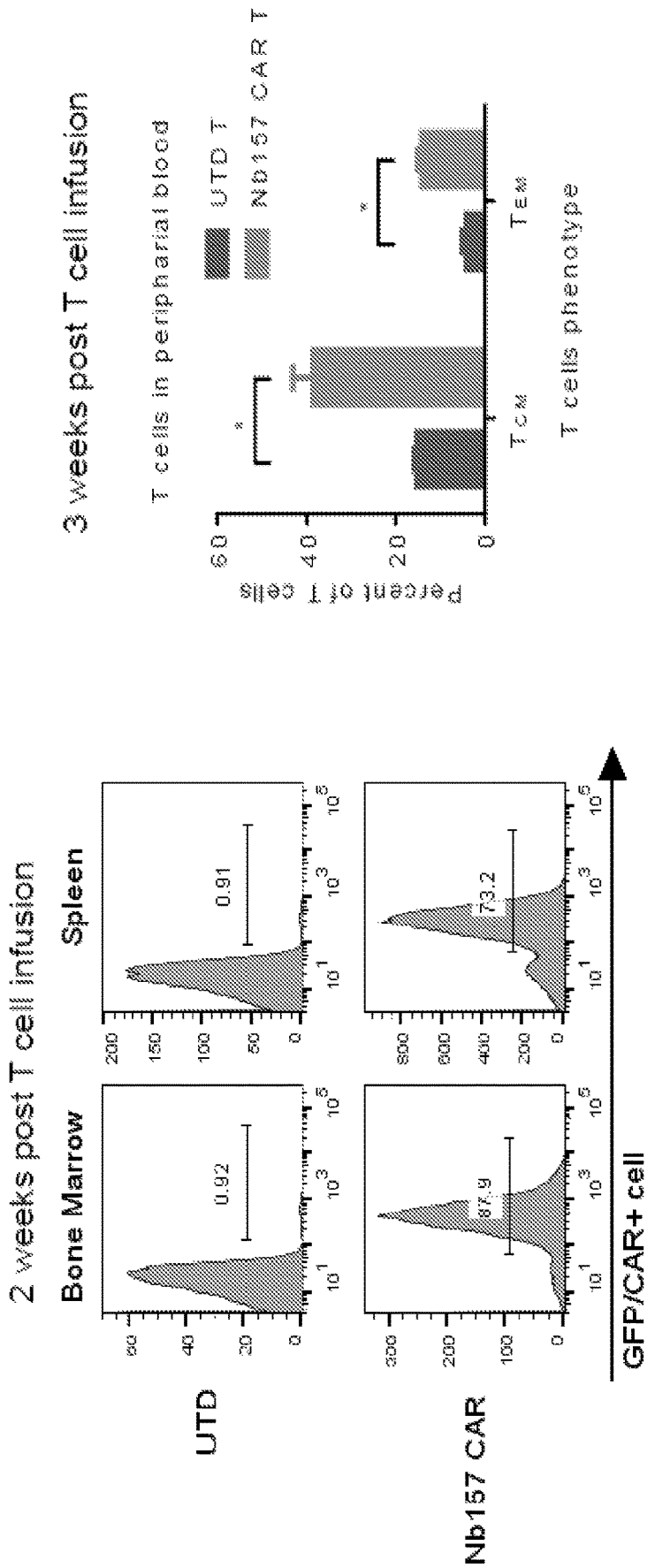

At the end points of experiment (day 45 for UTD group, FIG. 5J; and day 90 for Nb157 CAR group, FIG. 5K), the mouse spleens were harvested and processed for immunofluorescent staining for CD3+ T cells and CD33+ AML cells. The results indicated that a large number of CD33+ AML cells were detected in the spleen of control mice injected with UTD T cells but there were no obvious T cells (FIG. 5J). In contrast, in the spleens of the CAR T-injected mice, a large number of CD3+ CAR T cells were detected, but the CD33+ AML cells were eradicated (FIG. 5K). Consistently, there was apparent enrichment for CAR T cells in the bone marrow and spleen, increases in GFP percentage from initial 30% to more than 70% in the CAR T injected mice (FIG. 8B and FIG. 10C). Meanwhile, Nb157 CAR can induce T cells persistent memory phenotypes including both the central memory and the effector memory populations (FIG. 10C), which were correlated with complete remissions in CAR T clinical therapy. Together, these results indicated that Nb157 CAR T cells effectively eliminated the patient-derived AML cells in the bone marrow and spleen of the recipient mice and remarkably prolonged the survival.

Example 7: Nanobody Switch-Activated CAR T Cells Eradicated AML In Vivo in a Controllable Manner CAR T therapy may cause serious cytokine release syndrome and other on-target-off-tumor effects. To reduce this risk, as well as further attenuate the potential side effects of targeting moderately expressed CD13 in non-AML cells, an inducible and controllable system to manipulate the antitumor activity of Nb157 CAR T cells to AML was developed herein. Without wishing to be bound by specific theory, the CAR T cell system comprising a nanobody-switch could conditionally redirect CAR T cells to kill the tumors, but avoid permanent damage of other normal tissues to reduce the toxicity (e.g. mitigate cytokine release syndrome (CRS)).

Figure 6B:
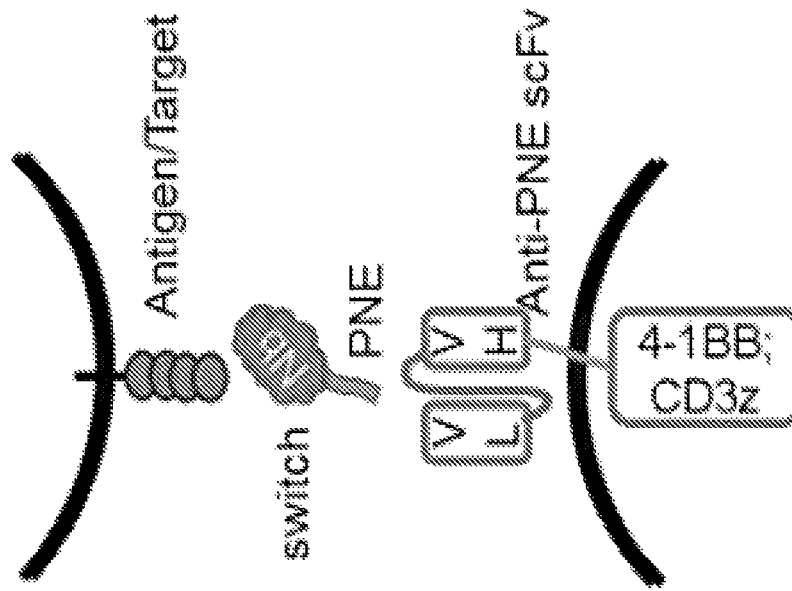
FIGS. 6A-6H are series of images and graphs depicting that Nb switch-activated CAR T cells eradicate AML in vivo in a controllable manner.
Figure 6A:
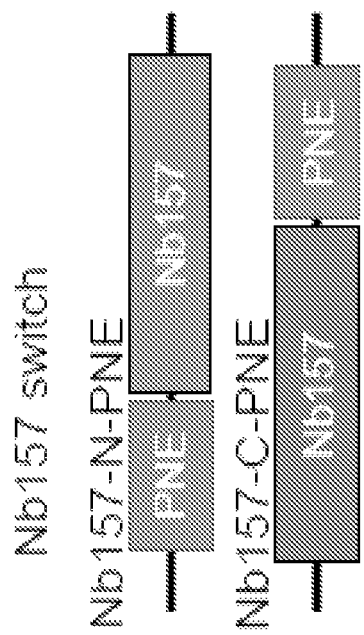
Figure 6C:
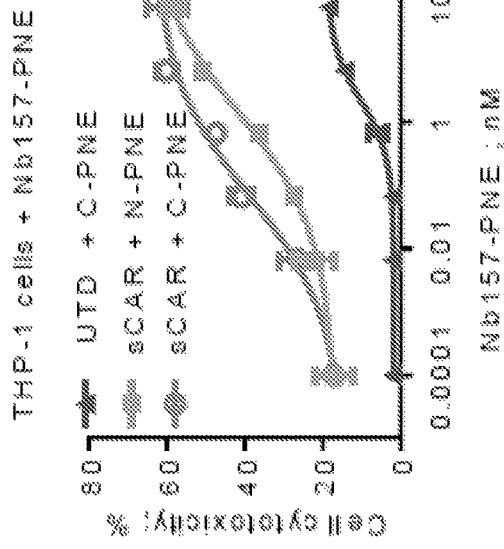
Figure 6E:
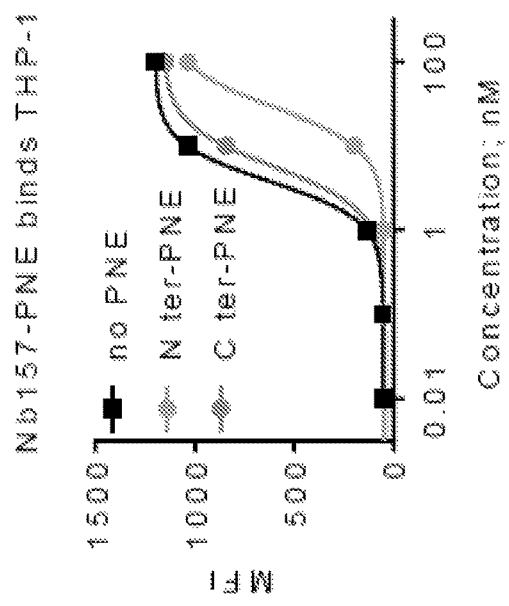
Figure 6D:
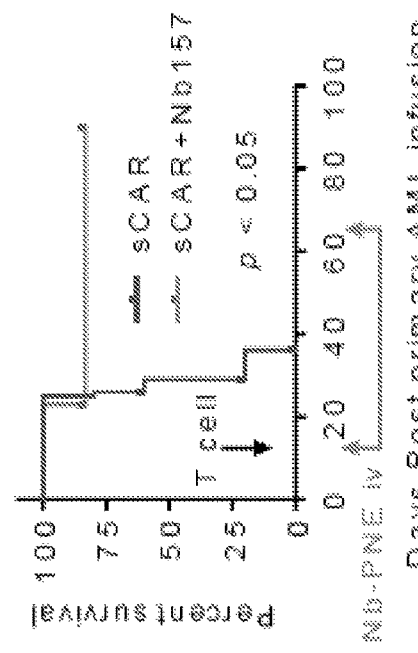
Figures 11A, 11B:
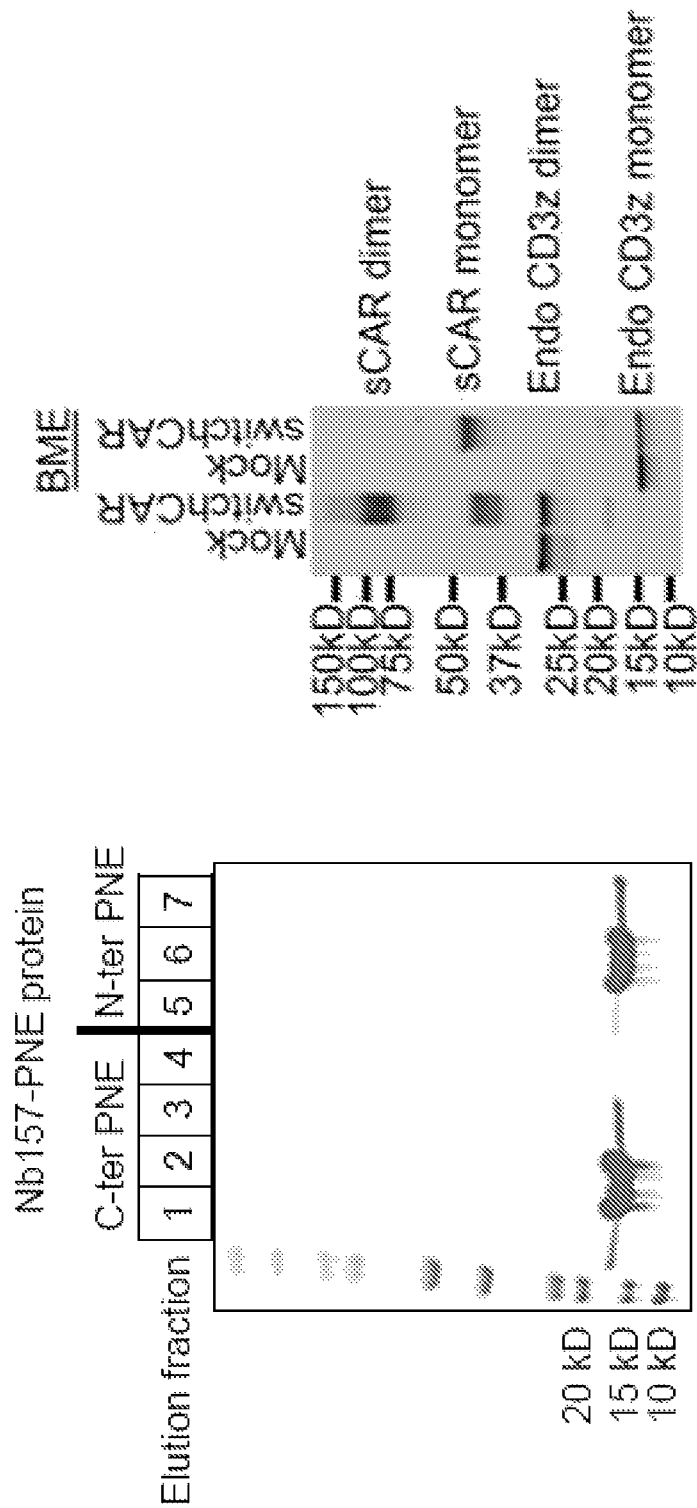
FIGS. 11A-11E are series of images and graphs depicting experiments in PNEs.
Figure 11E:
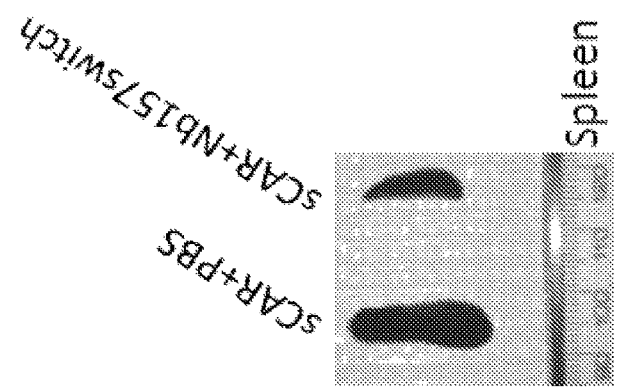
Figure 11C:
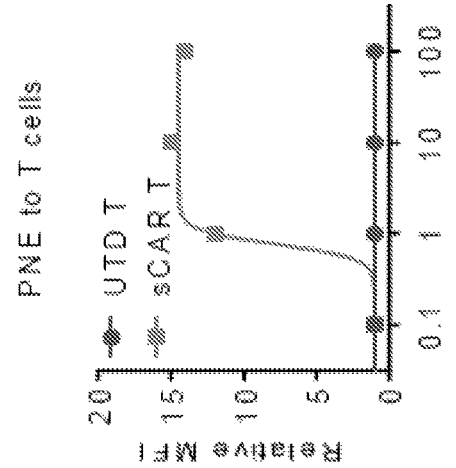
Figure 11D:
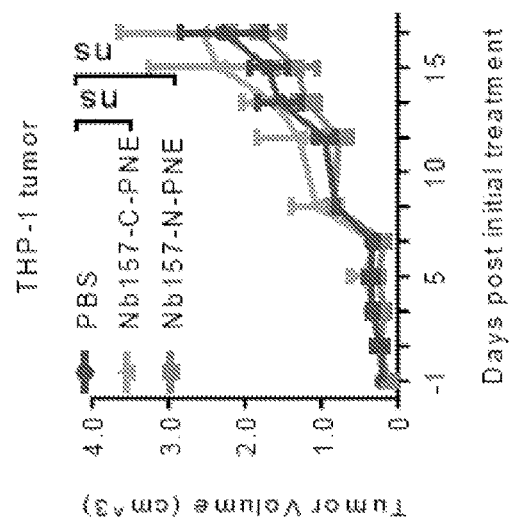

To this end, Nb157 was fused to a peptide PNE to form an inducible nanobody switch (FIG. 6A). Nb switches were expressed in bacteria and the purified proteins were ~15 kD as expected (FIG. 11A). The PNE peptide could be recognized by an established scFv which was fused to the CAR protein to construct the switchable CAR (sCAR) T cells (FIG. 6B). The sCAR construct was expressed in human primary T cells in a dimer of ~100 kD in non-reducing condition, which was broken down to ~50 kd in reducing condition. FITC-labeled PNE-peptide could bind sCAR T cells with $EC_{50}$ of 1 nM in vitro, but no binding for UTD T cells was observed (FIG. 11C). Flow cytometry analysis showed that Nb157-C-PNE and unmodified Nb157 bound THP-1 cells with a similar $k_d$ of ~35 nM (FIG. 6C). Notably, Nb157-N-PNE slightly reduced the binding affinity to ~90 nM (FIG. 6C). In vitro cytotoxicity assay showed that addition of Nb157-C-PNE switch potently triggered the killing of THP-1 cells by the sCAR T cells, but not by the UTD T cells (FIG. 6D). Consistently, a lower affinity of Nb157-N-PNE switch slightly reduced the cytolysis-inducing activity (FIG. 6D).

To determine whether the inducible switch, in concert with the sCAR T cells, can kill tumor in mice, THP-1 cells were transplanted into NSG mice subcutaneously to form tumors. Then sCAR or UTD T cells were injected intravenously into the tumor-bearing mice separately, followed by treatment of either Nb157-C-PNE protein or PBS every other day as indicated in FIG. 6e. The results indicated that the tumors in the UTD T, or UTD T plus Nb157 switch, or sCAR T cells-treated mice all grew exponentially (FIG. 6E). Moreover, injection of the switches alone did not inhibit the tumor growth (FIG. 11C). Notably, only tumors from mice treated with both sCAR T cells and Nb157-C-PNE switch significantly slowed down growth, during the first five times of switch injection (FIG. 6E). However, the tumors resumed to growth from day 10 to day 20 without the switch injection (FIG. 6E). It was determined whether resumption of the Nb157 switch injection suppress the tumor growth again. From day 21, Nb157 switch was restarted to treat the mice every other day. Interestingly, the tumor started to be shrunk and regressed from day 28. The tumor size continued to decrease until almost undetectable on day 52 along with Nb157 switch treatment for the whole process (FIG. 6E).

Figure 6F:
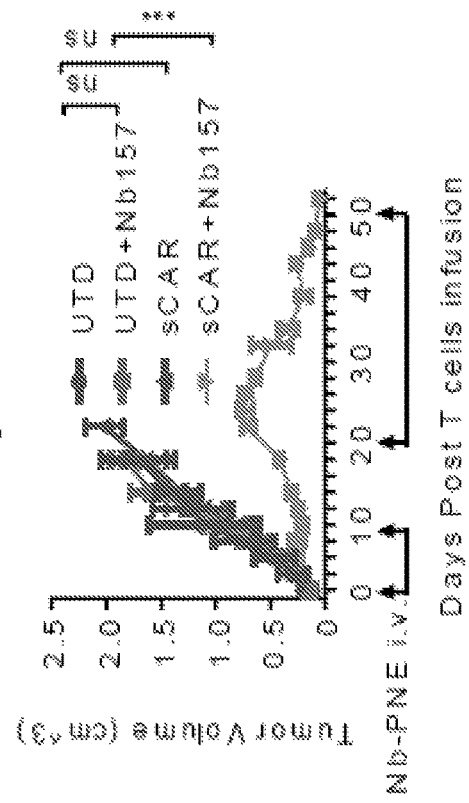
Figure 6H:
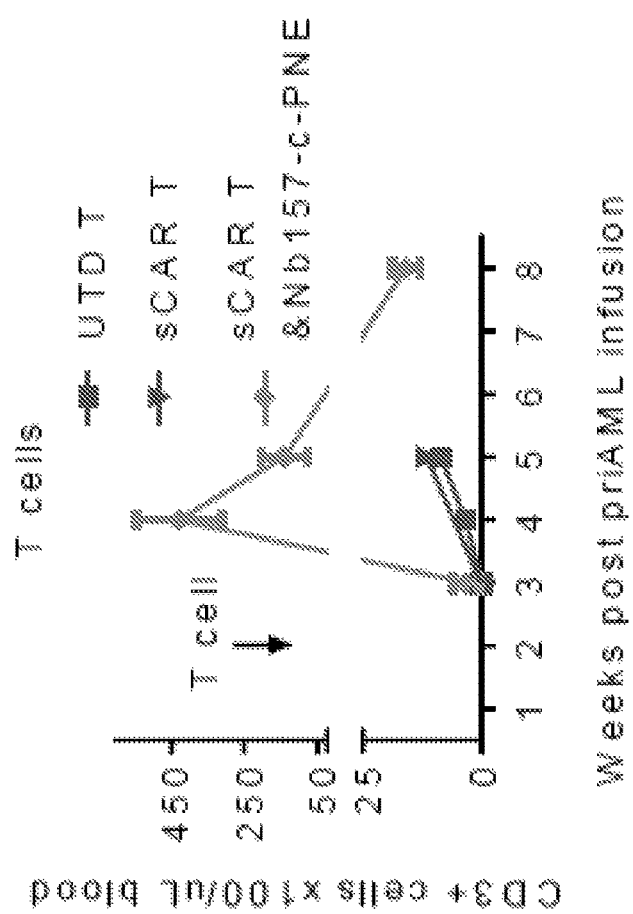
Figure 6G:
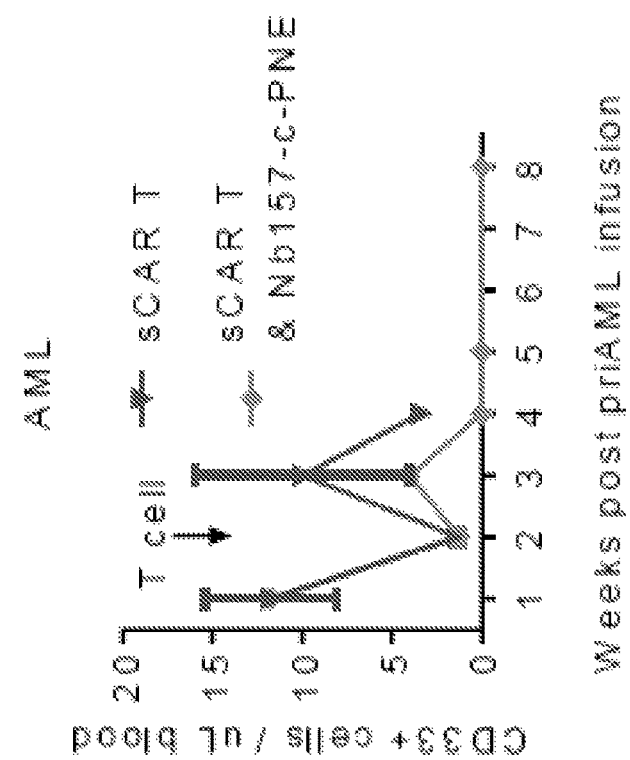

It was explored whether the switch CAR system can also suppress primary AML cells in mice. To this end, patient-derived AML cells were injected into the NSG mice to build leukemic mice model as determined by detection of the human CD33+ AML cells in the peripheral blood of the recipient mice (FIG. 6G). The leukemic mice were treated by sCAR T cells, followed by addition of either Nb157-C-PNE switch or PBS every other day as indicated in FIG. 6F. The appearance of CD33+ AML cells or CD3+ T cells in peripheral blood were monitored by flow cytometry analysis weekly. The results indicated that peripheral blood AML cells, following the first week of injection, gradually decreased in both sCAR T alone-injected mice and sCAR T plus Nb157 switch-injected mice (FIG. 6G), consistent with heavy leukemia infiltration in the spleen in later stage (FIG. 5H and FIG. 10A). Notably, treatment with sCAR T plus Nb157 switch, but not UTD T or sCAR T alone, increased peripheral T cells number two week after the sCAR T injection, reflecting the switch-triggered activation and proliferation of the sCAR T cells to kill the AML cells (FIG. 6H). Consistent with this observation, Kaplan Maier curve showed that treatment with sCAR T cells plus Nb157-C-PNE switch significantly protected the leukemic mice from dying compare to the treatment of sCAR T cell alone (FIG. 6F). Therefore, the results demonstrated that the Nb157-C-PNE switch targeting CD13 can effectively redirect sCAR T cells to eradicate the patient-derived AML cells in the clinical relevant models.

Example 8: Overview

Remarkable success for CAR T treatment in B cell malignancies highlights an important and promising direction to improve cancer immunotherapy. However, this kind of success has not yet expanded to other types of cancers such as AML. One rate-limiting factor, besides lack of cell type or tumor-specific surface targets, is insufficiency or unavailability of mAbs to evaluate the CARs' efficacy for cancer therapy. Moreover, many mAbs targeting cell surface proteins are not suitable for CAR T functions in vivo, failing to enable T cell trafficking, amplifying, destroying targets. As a result, novel strategies are necessary to develop multiple antibodies for multiple cell surface targets to evaluate the CAR T cell efficacies both in vitro and in vivo, accelerating the pace of developing effective caner CAR T therapy.

In this respect, several strengths for the STAR system are noteworthy to meet this need. First, STAR system is able to isolate numerous specific antibodies against various targets that are differentially expressed on the tumor cell surface based on the phage display. Nbs that recognized T cells were also filtered out in the process of negative cell absorption. Second, among these antibodies, only the ones that can both redirect the cognate CAR T cells to the tumor site from systemic circulation, and accumulate the CAR T cells in vivo will be isolated and chosen for further studies. Third, with the Nbs that passed the above two functional screenings, their antigens can be reliably retrieved for detailed CAR T studies. Notably, all the retrieved Nbs, when assembled into the CAR T cells, were capable of potently killing AML in vitro and empowering the cognate CAR T cells to kill the AML cells in vivo. These findings highlight the robust performance of this system to quickly uncover the new mAbs and their targets for developing novel and effective cancer CAR T therapy. Thus, the STAR system can be utilized to accelerate CAR T development by identifying effective CAR T-compatible antibodies and their antigens for various types of tumor models.

AML relapsed from chemotherapy is highly aggressive with poor prognosis. There is a strong need to develop more approaches to target AML cells via CAR T cells to improve therapy. The two of the Nbs we generated using the STAR system bound CD13 (aminopeptidase N, APN), and the Nb-driven CAR T specifically and potently killed AML cells, but not chronic leukemia cells, in vitro and in vivo. CD13 is preferentially expressed on AML cells and leukemia stem cells, and is moderately expressed in monocytic leukemia cells. Kaneko, T. et al described anti-CD13-based bi-specific T-cell engagers (BiTEs) could inhibit AML cell colony formation in culture[35] however, no any preclinical evaluation was further reported. CD13 is also expressed in human liver cancer stem cells, and inhibiting its enzyme activity results in suppression of liver cancer in mouse models. Together, the findings disclosed herein suggest that targeting CD13 by CAR T cells may preferentially kill the AML cells but have less impact on non-leukemic cells.

The persistence is the characteristic of CAR T cells in treated patients and may exacerbate the likelihood of CAR T on-target-off-tumor toxicity. The sCAR T system with the nanobody-driven switch developed herein allow for the temporary killing of CD13-expressing AML cells. There are several advantages to apply the nanobody switch to trigger CAR T cytotoxicity of cancer cells in vivo. First, as the nanobody switch is small, while it triggers potent AML killing in vivo, it has a relative short life to avoid CAR T mediated permanent damage of other normal cells. Second, the small size of nanobody switch makes it better to penetrate the tumor microenvironment and thus engage the CAR T cells in the tumor site to eliminate the target. Third, as the nanobody switch can reversibly trigger the CAR T cells to kill AML cells, this likely reduces T cell exhaustion due to the chronic and persistent stimulation of the T cells as the CAR is constitutively activated in the tumor site, likely leading to CAR T cell exhaustion. While CD13 is expressed highly in AML blast cells, it is also expressed moderately in a few non-leukemia cells like colon epithelial cells, and kidney tubular epithelial cells. In this respect, the nanobody switch will likely kill the cancer cells, yet render the damage to the relevant normal tissues as reversible and manageable "inflammation" or "autoimmune response".

It is conceivable that the STAR system is also be valuable for quickly discovering tumor-specific and CAR-compatible antibodies, as well as novel tumor targets for other types of cancers. Moreover, the current approach can generate multiple and CAR-compatible Nb switches targeting various TAAs or other targets. With these Nb switches, it is possible to treat cancer with temporally controlled use of the multiple switches of the CAR T cells to target the cell surface TAAs, based on monitoring the evolution of the personalized cancer surface TAAs, to improve cancer therapy. It is also possible to employ the dynamic and combinatory use of the multiple TAA-targeting switches to increase efficacy and reduce the toxicity. In summary, the present invention not only established a technical platform, the STAR system, to simultaneously isolate tumor-specific and CAR T-compatible Nbs, but also demonstrated that the isolated Nbs preferably bind AML and empower CAR T cells to eradicate AML, expediting the development of effective cancer CAR T therapy. This invention allows for the development of novel immunotherapies by generating STAR selected antibodies for CAR T cells or antibody conjugating drug (ADC) or tumor-diagnostic agents.

Example 9: Developing Nanobody-Directed Immunotherapy to Improve NET Treatment

Neuroendocrine tumors (NETs) pose serious threats to patients' well-being as malignant diseases, and most patients with metastatic NETs succumb to the disease. A remarkable feature common to most well differentiated NETs is the overexpression of somatostatin receptor 2 (SSTR2). Although Octreotide (a drug analog of somatostatin) and other similar derivatives have been used to target SSTR2 to suppress the secretion of hormones from the tumor cells and to inhibit tumor cell growth, the somatostatin analogs rarely kill tumor cells and reduce tumor mass. As such, it is sorely needed to develop novel therapies that selectively eradicate NET cells. Recently, adoptive T cell therapy involving engineered chimeric antigen receptors (CARs) targeting CD19-expressing leukemia or lymphoma has been shown to eradicate lymphocytic leukemia or lymphoma, and approved by FDA for therapy.

Moreover, antibody drug conjugates (ADCs), which are specific monoclonal antibodies (mAbs) linked to the cancer cell-killing drugs, have also been shown to effectively kill leukemia or solid tumor cells in patients. These advances raise an exciting possibility that NETs can be specifically targeted via CAR T cells or a NET-specific ADC to effectively eradicate NET cells. However, lack of specific cell surface tumor-associated antigens and corresponding antibodies constrain using CAR-T cell or ADC therapies to treat most of other types of cancers, such as NETs.

The camel family of animals including llama can produce heavy chain-only antibodies (which contain a single variable domain, a.k.a nanobody or VHH). These type of antibodies have a unique advantage as they can bind the small cavity of proteins, notably cell surface proteins such as G protein coupled receptors (GPCRs), ion channels and transporters, which are usually hard to be targeted by regular antibodies. Moreover, VHHs also tend to have low immunogenicity in humans. Herein, NET cell surface antigen-specific VHH antibodies were generated via phage display and NET-specific VHH-CAR T cells developed. The effect of VHH-CAR T cells to kill NET cells in vitro and in vivo was demonstrated. Additionally, a NET-specific VHH based ADC drug was developed to treat NET cells in vitro and in vivo.

To achieve these goals, peripheral blood mononuclear cells (PBMCs), including B cells from 38 unimmunized naive llamas, were collected to make RNA and synthesize cDNAs. The variable regions of the heavy chain of the immunoglobulin heavy chain genes (VHH) were amplified with PCR, ligated to the phage display vector, and transformed into competent cells, yielding the VHH phage display library with >$10^{10}$ independent phage clones.

To screen for VHHs specifically binding to NET cell surfaces from the phage library, freshly prepared VHH phage, which express antigen binding VHH as a pIII fusion protein on their surface, was incubated with BON cells, followed by centrifuging to pellet BON cells to remove unbound phage. The pelleted cells were washed in flow-cytometry buffer, and the bound VHH phage was eluted from the cells. The eluted phage was amplified, and then counter-selected with human breast cancer BT474 cells, followed by four rounds of selection with BON cells (similar to illustration in FIG. 1A).

Figure 12A:
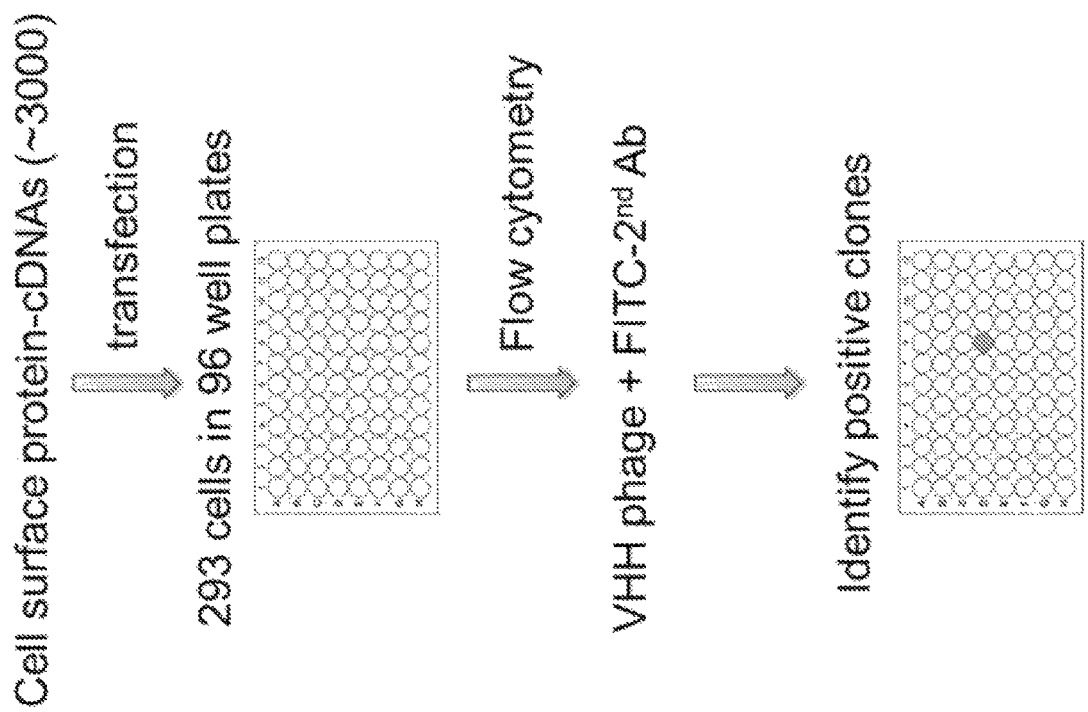

Next, to identify the protein antigen of the isolated VHH1 nanobody, ~3000 human cell membrane protein cDNAs were prepared and transfected into HEK293T cells individually, followed by flow cytometry analysis with the VHH1-expressing phage and FITC-labeled secondary antibody against phage M13 protein (FIG. 12A). After screening the ~3000 cell surface proteins, results showed that VHH1 only bound to human full length CDH17, also called cadherin 17 or liver-intestine cadherin (FIG. 12B). Further western blot results showed that BON cells have robust CDH17 protein expression compared with other tested cell lines (FIG. 12C). Human or mouse CDH17 cDNA was transiently transfected into HEK293T cells, followed by flow cytometry analysis with the VHH1-expressing phage and FITC-labeled secondary antibody against phage M13 protein. The results clearly showed that VHH1 bound both human and mouse CDH17 (FIG. 12D), which provides the opportunity to analyze the potential toxicity of VTH1-CAR T cells in mice.

Figures 22A, 22B:
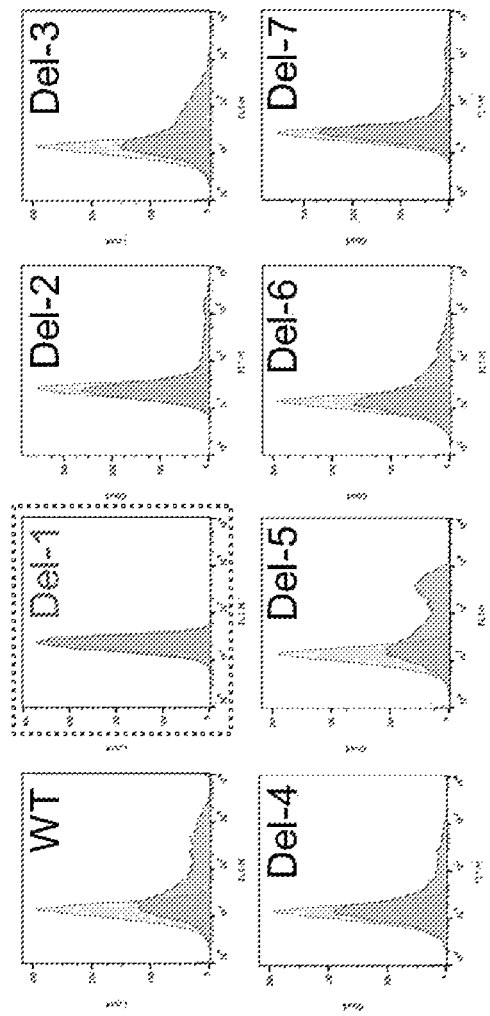
FIGS. 22A-22C are series of images and graphs depicting that the VHH1 binds to the EC1 domain of CDH17.
Figure 22C:
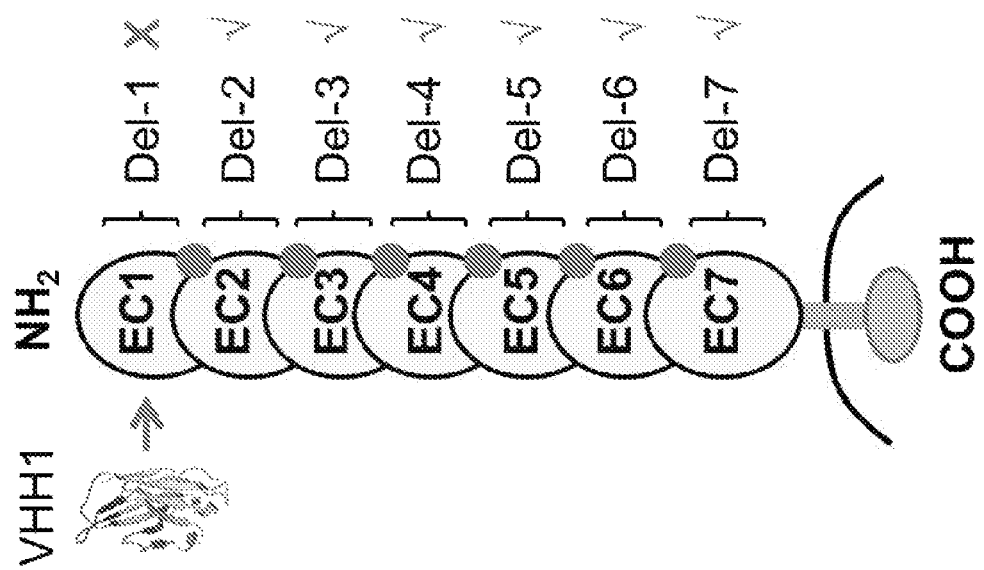

In order to further confirm the antigen of VHH1 is CDH17, several CDH17 internal truncations were constructed. The truncations were transfected into HEK293T cells. Flow cytometry analysis was performed with the purified VHH1 nanobody and APC labeled anti-HA secondary antibody against HA on VHH1 nanobody, indicating that VHH1 binds to CDH17. Additionally, several CDH17 internal truncations were constructed (FIG. 22A) and transfected into HEK293T cells. Flow cytometry analysis was performed with the purified VHH1 nanobody and APC labeled anti-HA secondary antibody against HA on VHH1 nanobody. As shown in FIG. 22B, the EC1 domain deleted truncation, Del-1, completely lost the function to interact with VHH1 nanobody and the full length CDH17 and other truncations could be bound by VHH1 (FIGS. 22B-22C), indicating that VHH1 binds to the EC1 domain at the N-terminal part of CDH17. CDH17, a cell adhesion protein highly expressed in human NETs. CDH17 is a cell adhesion protein highly expressed in human NETs. All of the four fresh human pancreatic neuroendocrine tumor (PNET)

samples taken via biopsy from liver were robustly bound by VHH1 (FIG. 13C), indicating that CDH17 is highly expressed in PNETs. One nanobody, named VHH1 was identified that specifically binds to CDH17 protein. VHH1-CAR T cells specifically and robustly killed CDH17 expressing NET BON cells. The VHH1 sequence was cloned into the CAR vector (FIG. 13C), and the resulting CAR T cells showed marked killing of BON cells using LDH release assay, while the control UTD cells failed to kill the cells (FIG. 13D). VHH1 was sequenced and confirmed to contain the conserved VHH sequence (FIG. 14).

Figure 15A:
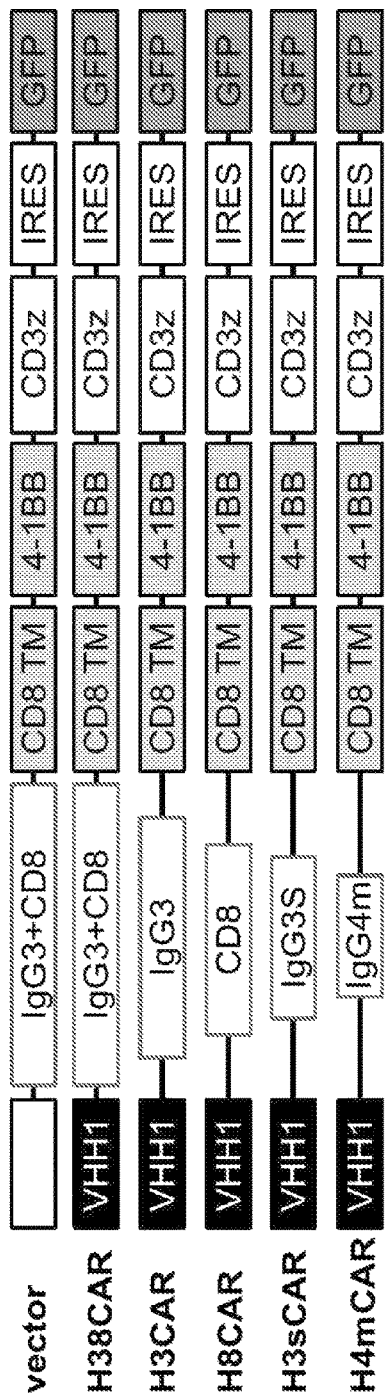
FIGS. 15A-15B depict construction of VHH1-41BB-CD3z-CARs with different hinge lengths.
Figure 15B:
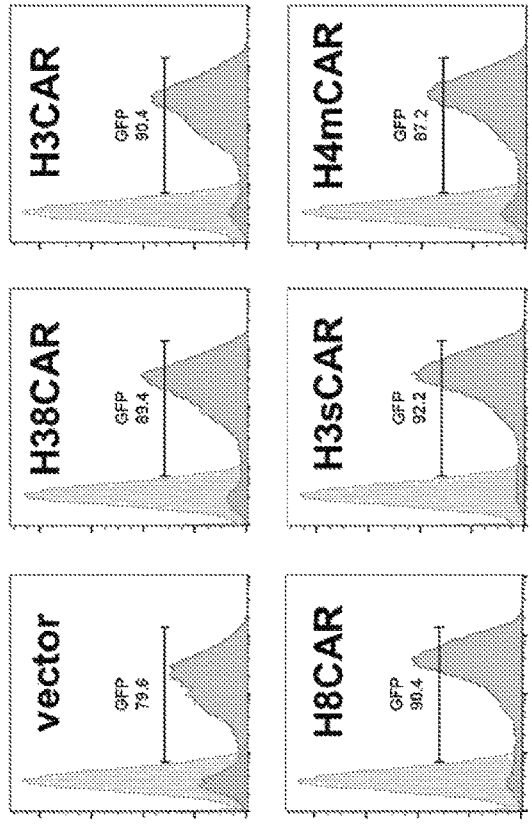
Figure 16A:
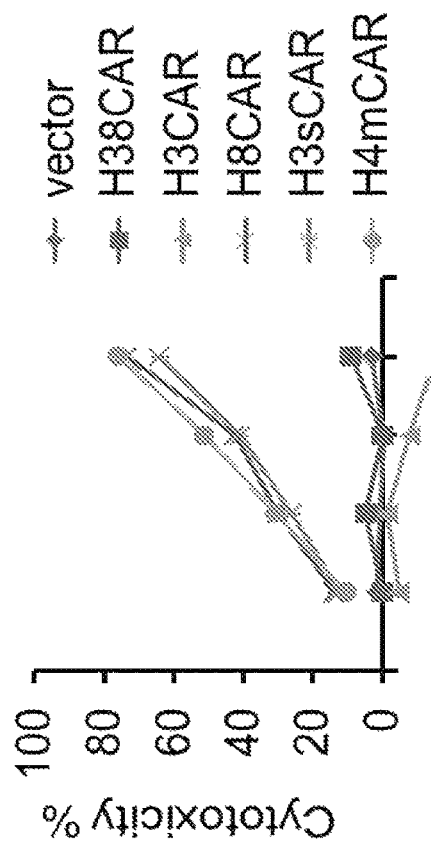
FIGS. 16A-16F are series of images and graphs depicting VHH1-CAR JRT3 cells with short hinges specifically killed BON cells.
Figure 16B:
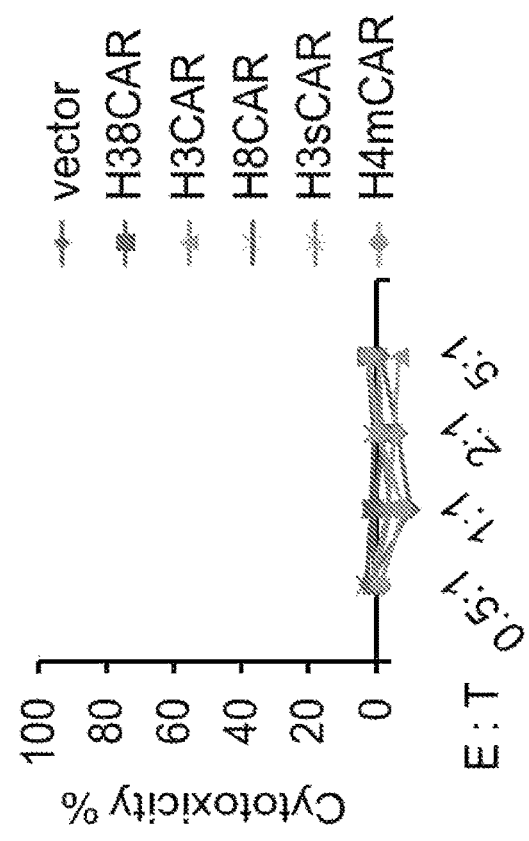
Figure 16C:
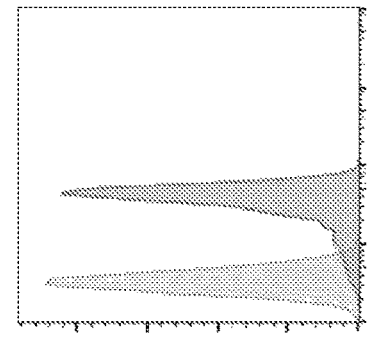
Figure 16D:
Figures 16E, 16F:
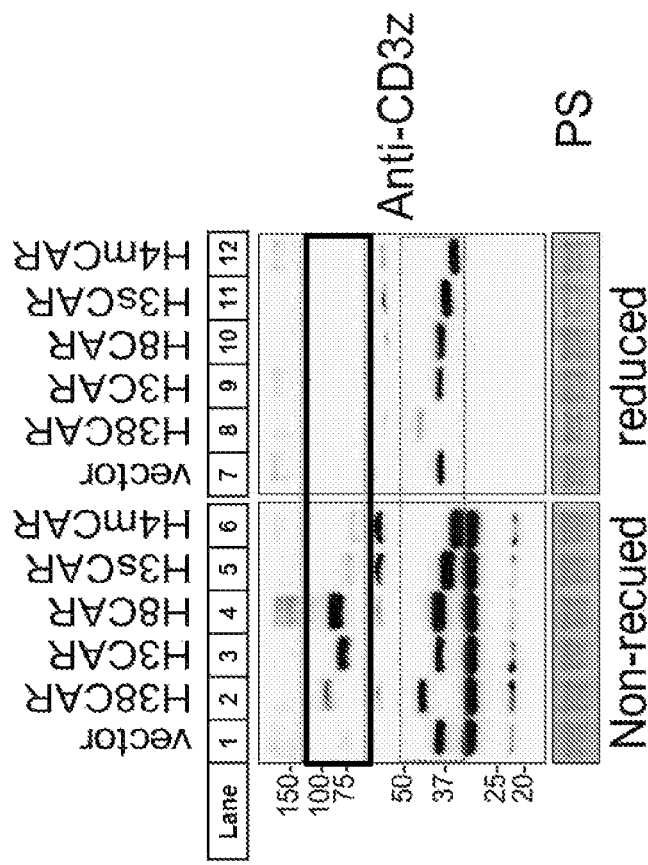

To determine if VHH1 directs CAR T cells to kill BON cells with certain length of the linker between VHH1 and the transmembrane domain (TM) of the CAR construct, an acute T cell leukemia cell line, JRT3 cells, was first used to perform a killing assay. It is well known that the distance between T cells and target cells is crucial for the formation of synapse of T cells and for T cells killing on target cells. Therefore, VHH1-CARs with several different hinge lengths were constructed in order to optimize the most effective CAR structure (FIG. 15A). The VHH1-CARs include different hinge lengths, a CD8 transmembrane domain, 4-1BB and CD3zeta domains and IRES-GFP for detection of positive CAR T cells (FIG. 15A, and the linker lengths summarized in FIG. 15B). Lentivirus was packaged and transduced into JRT3 cells, and all the resulting CARs were expressed in the T cells as illustrated by flow cytometry analysis for GFP expression (FIG. 15C). The resulting JRT3 cells expressing VHH1-CAR with CD8, IgG3s and IgG4m hinges specifically killed BON cells which can be bound by VHH1 (FIGS. 16A-16B), but not control BT474 cells which cannot be bound by VHH1 (FIG. 16C-16D). Results were from a lactate dehydrogenase (LDH) release assay. Consistently, western blot analysis confirmed different VHH1-CAR proteins expressed in JRT3 cells (FIG. 16E). In summary, JRT3 cells expressing VHH1-CAR with short hinges, CD8, IgG3s and IgG4m, killed BON cells, but the VHH1-CAR JRT3 cells with long hinges, IgG3+CD8 and IgG3, failed to kill BON cells (FIG. 16F).

Although, VHH1-CAR JRT3 cells showed potent killing capability on BON cells, JRT3 cells are cancer cells and can not be used to treat patients. Therefore, human primary T cells were chosen to be used. To confirm the above results, the same VHH1-CARs with different hinge lengths were also transduced into human primary T cells and the CAR expression on the T cell surface was detected by flow for GFP expression (FIG. 17A). The resulting human primary T cells expressing VHH1-CAR with CD8 and IgG4m hinge specifically killed BON cells (FIG. 17B), but not BT474 cells (FIG. 17C), measured using an LDH release assay. The VHH1-CAR T cells with an IgG4m hinge killed BON cells most effectively (FIG. 17B), but not BT474 breast cancer cells (FIG. 17C). Consistently, the VHH1-CAR T cells with an IgG4m hinge bound the BON cells under microscopic observation (FIG. 17B), but not BT474 cells (FIG. 17C). Western blot analysis confirmed different VHH1-CAR proteins were expressed in human primary T cells (FIG. 17D). In summary, the results showed that human primary T cells expressing VHH1-CAR with CD8 and IgG4m hinges specifically killed BON cells, but the VHH1-CAR T cells with IgG3+CD8 and IgG3 or IgG3s hinges failed to kill BON cells (FIG. 17E). The VHH1-CAR T cells with an IgG4m hinge killed BON cells most effectively (FIG. 17B), so the VHH1-CAR with IgG4m hinge was chosen for further studies (FIG. 18A).

Next, the killing of VHH1-CAR (aka CDH17CAR) T cells on BON cells in vivo was analyzed. To evaluate the efficacy of VHH1-CAR T cells on NET xenograft, BON cells were transplanted into the NSG mice. Fourteen days later, VHH1 CAR T cells or untransduced (UTD) T cells as control were transfused into the NSG mice bearing the NETs via tail vein. The results showed that VHH1 CAR T cells inhibited NET tumor growth significantly, but did not eradicate the tumor.

Figure 19A:
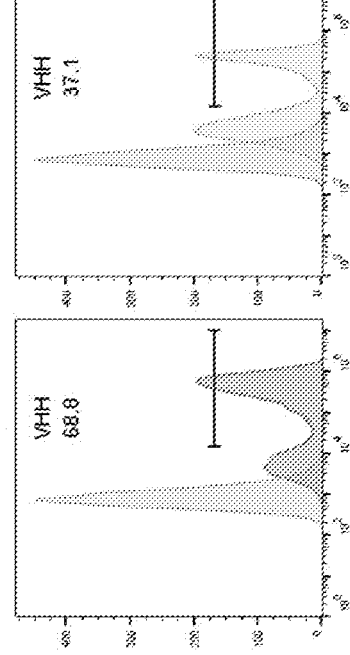
FIGS. 19A-19D show a series of graphs depicting that CDH17CAR T cells eliminated CDH17-expressing SKVO3 tumors in vivo.
Figure 19B:
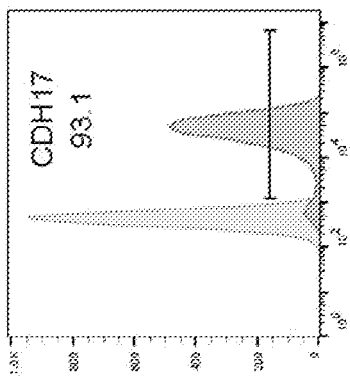
Figure 19D:
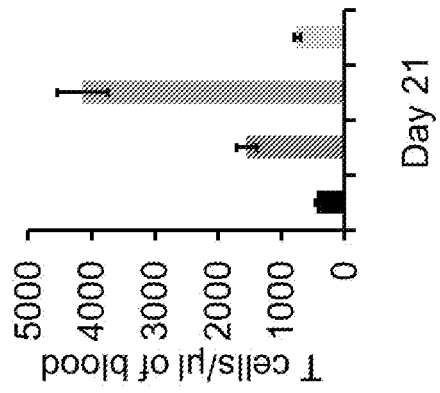
Figure 19C:
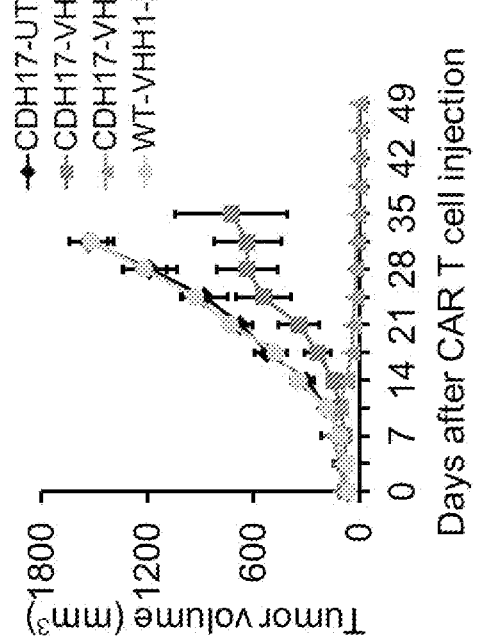

To confirm whether the CDH17CAR T cells are capable of killing cancer cells in CDH17-specific manner in vivo, CDH17 was ectopically expressed into a CDH17 negative human acute leukemia cell line, NB4 cells and sorted the CDH17 positive cells. Flow cytometry data showed that most of the cells have CDH17 expression (FIG. 18A). CDH17-NB4 cells were transplanted into the flank of NSG mice, followed by injection of VHH1 second generation CAR T cells with 4-1BB and CD3z via tail vein (FIG. 18B). The results showed that VHH1-BBz CAR T cells completely eradicated the CDH17-NB4 tumors in vivo (FIG. 18C). Consistently, CAR T cells amplified in peripheral blood as compared to UTD T cells (FIG. 18D). Next, CDH17 was ectopically expressed into a CDH17 negative solid human ovary cancer cell line, SKOV3 cells, and the CDH17 positive cells were sorted and passaged (FIG. 19A). To evaluate the efficacy of VHH1-CAR T cells on SKOV3 xenograft, WT or CDH17-SKOV3 cells were transplanted into the NSG mice. 24 days later, second generation VHH1-BBz CAR, third generation VHH1-28BBz CAR with CD28 and 4-1BB co-stimulatory domains or UTD T cells were transfused into the NSG mice bearing the WT or CDH17-SKOV3 xenografts intravenously. The results showed that VHH1-28BBz CAR T cells completely eradicated the CDH17-SKOV3 tumors, but not the CDH17 negative WT SKOV3 tumors (FIG. 19C). However, VHH1-BBz CAR T cells only repressed tumor growth, but did not eradicate the tumors (FIG. 19C). Consistently, NSG mice with CDH17-SKOV3 tumors treated with VHH1-28BBz CAR T cells had the highest T cell number in peripheral blood as compared to other groups (FIG. 19D). Together, the results indicate that VHH1-CAR T cells indeed can eradicate the tumors in vivo.

Recently, a new well-differentiated human pancreatic neuroendocrine tumor cell line, NT-3, which has expression of typical pancreatic NETs like SSTR2, chromogranin A and insulin, was established. Flow cytometry data showed that NT-3 cells were robustly bound by VHH1 (FIG. 20A), indicating that NT-3 cells have high CDH17 expression. Co-culturing VHH1-CAR T cells with NT-3 cells showed that both VHH1-BBz and VHH1-28BBz CAR T cells significantly killed NT-3 cells in vitro (FIG. 20B), using LDH release assay. Furthermore, VHH1-28BBz CAR T cells completely eradicated the NT-3 tumors in NSG mice without affecting the body weight of the mice (FIGS. 20C, 20D, and 20F). VHH1-28BBz CAR T cell number in peripheral blood increased at day 14 after T cell injection and then reduced at day 21 after tumor eradication (FIG. 20E). This series of studies indicates that the CDH17 CARs are capable of and potent in killing and eradicating NETs in vivo and CDH17 serves as valuable target for NETs and other CDH17-expressing tumors. Further, as the CDH17 CAR Ts did not cause obvious toxicities in mice, without loss of body weight, these findings indicate that CDH17 serves as an effective and safe target for immunotherapy against NETs and other types of cancers expressing CDH17.

Figure 21H:
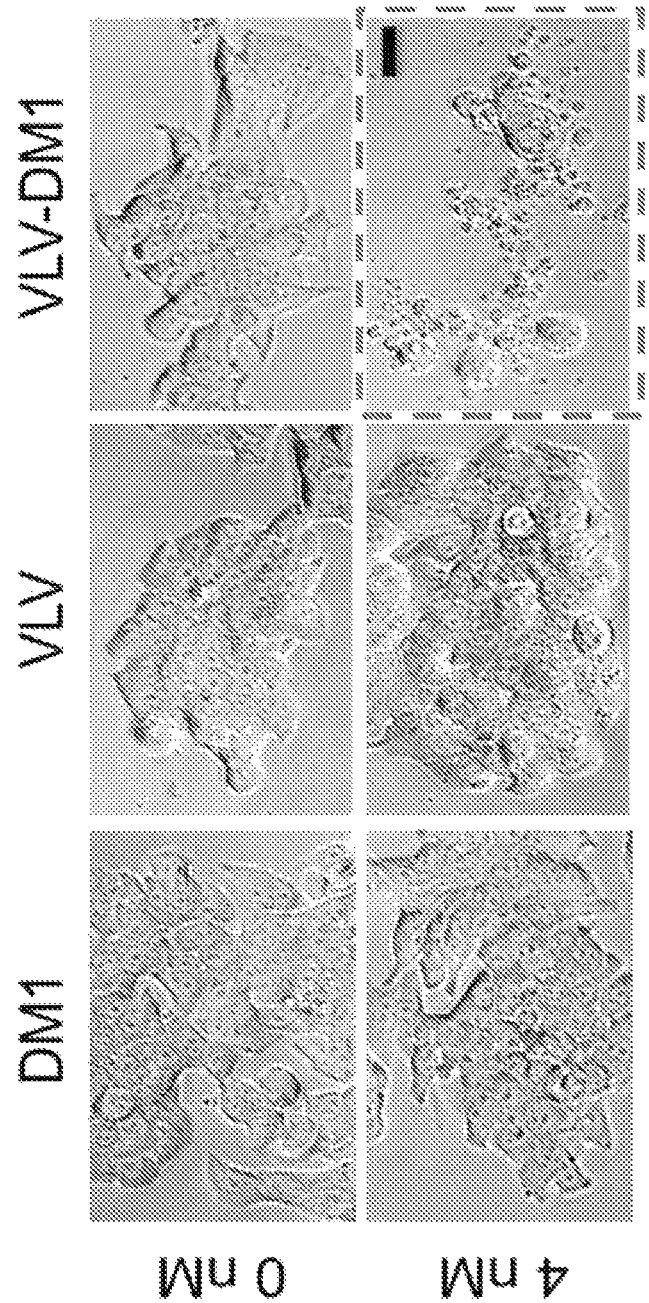

The effect of VHH1-ADC on suppressing NET tumors was evaluated. To test whether VHH1 ADC specifically kills NET cells, Mertansine (DM1), which is toxic to cancer cells by blocking microtubule assembly and DM1-conjugated anti-HER2 antibody has been approved for treating breast cancer, was conjugated to VHH1 homodimer connected by a linker (VHH1-linker-VHH1, aka VLV) (FIGS. 21A-21B). As a control, FITC labeled-VLV, when incubated with CDH17-expressing BON cells, was markedly internalized into BON cells (FIG. 21C, left), but not the CDH17-negative QGP1 cells (FIG. 21C, right). Flow data showed that both unconjugated VLV and VLV-DM1 bound to BON cells, albeit with slightly reduced affinity for VLV-DM1 (FIG. 21D), but not QGP1 cells (FIG. 21E). Furthermore, cytotoxicity assay showed that VLV-DM1 significantly killed BON cells (FIG. 21F), likely via internalized DM1, but not CDH17-negative QGP1 cells (FIG. 21G). The morphology data also clearly showed that the VLV-DM1 lysed the BON cells at 4 nM, but not unconjugated DM1 or VLV (FIG. 21H). These results demonstrated the impact of VHH1-ADC on killing NET cell line-derived xenograft and NET PDX in immunodeficient mice.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A chimeric antigen receptor (CAR) comprising a nanobody, a transmembrane domain, and an intracellular signaling domain, wherein the nanobody specifically binds to the first domain of CDH17, wherein the nanobody comprises a CDR1 region comprising the amino acid sequence of SEQ ID NO: 3, a CDR2 region comprising the amino acid sequence of SEQ ID NO: 4, and a CDR3 region comprising the amino acid sequence of SEQ ID NO: 5.

2. The CAR of claim 1, wherein the nanobody comprises the amino acid sequence of SEQ ID NO: 2.

3. The CAR of claim 1, wherein the nanobody is encoded by the nucleotide sequence of SEQ ID NO: 1.

4. The CAR of claim 1, wherein the CAR further comprises a hinge domain selected from the group consisting of a CD8 hinge, an IgG3s hinge, and an IgG4m hinge.

5. The CAR of claim 4, wherein the hinge domain comprises the amino acid sequence of any one of SEQ ID NOs: 20 or 38.

6. The CAR of claim 1, wherein the transmembrane domain is selected from the group consisting of CD8, CD28, and ICOS.

7. The CAR of claim 1, wherein the transmembrane domain comprises SEQ ID NO: 21.

8. The CAR of claim 1, wherein the intracellular signaling domain comprises 4-1BB and CD3 zeta.

9. The CAR of claim 1, wherein the intracellular signaling domain comprises SEQ ID NO: 22.

10. The CAR of claim 1, wherein the CAR comprises the amino acid sequence of any one of SEQ ID NOs: 34 or 36.

11. The CAR of claim 1, wherein the CAR is encoded by the nucleotide sequence of any one of SEQ ID NOs: 33 or 35.

12. A modified T cell or precursor thereof, comprising the CAR of claim 1.

13. A method for treating cancer in a subject in need thereof, the method comprising administering to the subject a modified T cell or precursor thereof comprising the CAR of claim 1.

14. The method of claim 13, wherein the cancer is acute myeloid leukemia (AML).

15. The method of claim 13, wherein the cancer is a neuroendocrine tumor (NET).

16. The method of claim 13, wherein the cancer is colorectal cancer.

17. A composition comprising a nucleic acid encoding a chimeric antigen receptor (CAR), the CAR comprising a nanobody, a transmembrane domain, and an intracellular signaling domain, wherein the nanobody specifically binds to the first domain of CDH17, wherein the nanobody comprises a CDR1 region comprising the amino acid sequence of SEQ ID NO: 3, a CDR2 region comprising the amino acid sequence of SEQ ID NO: 4, and a CDR3 region comprising the amino acid sequence of SEQ ID NO: 5.

* * * * *

SEQUENCE LISTING

<160> NUMBER OF SEQ ID NOS: 38

<210> SEQ ID NO 1
<211> LENGTH: 354
<212> TYPE: DNA
<213> ORGANISM: Artificial Sequence
<220> FEATURE:
<223> OTHER INFORMATION: VHH1 nanobody

<400> SEQUENCE: 1

```
caggtgcagc tgcaggagtc tggggggagga ttggtgcagc ctgggggctc gacaagactc      60
tcctgtgtat cgtcccgcac ctttagttat tatgacatgg gctggttccg ccaggctcca     120
gggaaggagc gtgagttcgt agcactgctt agttggaatg gggaaaatgc agagtattca     180
gactccgtga tgggccgttt caccgtctcc cgagggaata cccagaattc ggtgaatctg     240
caaatgaaca acctgaaacc tgaggacacg ggcatctatt actgcgcagt gacgcacggt     300
ggagcgcggt cggttcgttc ctggggccag gggacccagg tcaccgtctc ctca           354
```

<210> SEQ ID NO 2
<211> LENGTH: 118
<212> TYPE: PRT
<213> ORGANISM: Artificial Sequence
<220> FEATURE:
<223> OTHER INFORMATION: VHH1 nanobody

<400> SEQUENCE: 2

```
Gln Val Gln Leu Gln Glu Ser Gly Gly Gly Leu Val Gln Pro Gly Gly
1               5                   10                  15

Ser Thr Arg Leu Ser Cys Val Ser Ser Arg Thr Phe Ser Tyr Tyr Asp
            20                  25                  30

Met Gly Trp Phe Arg Gln Ala Pro Gly Lys Glu Arg Glu Phe Val Ala
        35                  40                  45

Leu Leu Ser Trp Asn Gly Glu Asn Ala Glu Tyr Ser Asp Ser Val Met
    50                  55                  60

Gly Arg Phe Thr Val Ser Arg Gly Asn Thr Gln Asn Ser Val Asn Leu
65                  70                  75                  80

Gln Met Asn Asn Leu Lys Pro Glu Asp Thr Gly Ile Tyr Tyr Cys Ala
                85                  90                  95

Val Thr His Gly Gly Ala Arg Ser Val Arg Ser Trp Gly Gln Gly Thr
            100                 105                 110

Gln Val Thr Val Ser Ser
        115
```

<210> SEQ ID NO 3
<211> LENGTH: 5
<212> TYPE: PRT
<213> ORGANISM: Artificial Sequence
<220> FEATURE:
<223> OTHER INFORMATION: VHH1 nanobody CDR1

<400> SEQUENCE: 3

Tyr Tyr Asp Met Gly
1               5

<210> SEQ ID NO 4
<211> LENGTH: 18
<212> TYPE: PRT
<213> ORGANISM: Artificial Sequence
<220> FEATURE:
<223> OTHER INFORMATION: VHH1 nanobody CDR2

<400> SEQUENCE: 4

Leu Leu Ser Trp Asn Gly Glu Asn Ala Glu Tyr Ser Asp Ser Val Met
1               5                   10                  15

Gly Arg

<210> SEQ ID NO 5
<211> LENGTH: 12
<212> TYPE: PRT
<213> ORGANISM: Artificial Sequence
<220> FEATURE:
<223> OTHER INFORMATION: VHH1 nanobody CDR3

<400> SEQUENCE: 5

Ala Val Thr His Gly Gly Ala Arg Ser Val Arg Ser
1               5                   10

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
atttcaggtg tcgtgagcgg                                                 20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
aggagaagga ccccacaagt                                                 20

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
cagctatcgc gattgcagt                                                  19

```
<210> SEQ ID NO 9
<211> LENGTH: 13
<212> TYPE: DNA
<213> ORGANISM: Artificial Sequence
<220> FEATURE:
<223> OTHER INFORMATION: SfiI site
<220> FEATURE:
<221> NAME/KEY: misc_feature
<222> LOCATION: (5)..(9)
<223> OTHER INFORMATION: n is a, c, g, or t

<400> SEQUENCE: 9
ggccnnnnng gcc                                                          13

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
gtcctggctg ctcttctaca agg                                               23

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
ggtacgtgct gttgaactgt tcc                                               23

<210> SEQ ID NO 12
<211> LENGTH: 64
<212> TYPE: DNA
<213> ORGANISM: Artificial Sequence
<220> FEATURE:
<223> OTHER INFORMATION: primer

<400> SEQUENCE: 12
gaggaggagg aggaggaggc ggggcccagg cggcccaggt gcagctgcag gagtctggrg        60
gagg                                                                    64

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
gaggaggagg aggaggagcc tggccggcct ggccactagt ggcggccgct gaggagacgg        60
tgacctgggt                                                              70

<210> SEQ ID NO 14
<211> LENGTH: 20
<212> TYPE: DNA
<213> ORGANISM: Artificial Sequence
<220> FEATURE:
<223> OTHER INFORMATION: sgRNA

<400> SEQUENCE: 14
atggccggct catcgaagca                                                   20
```

<210> SEQ ID NO 15
<211> LENGTH: 20
<212> TYPE: DNA
<213> ORGANISM: Artificial Sequence
<220> FEATURE:
<223> OTHER INFORMATION: sgRNA

<400> SEQUENCE: 15
cttcccatgc ttcgatgagc                                                     20

<210> SEQ ID NO 16
<211> LENGTH: 20
<212> TYPE: DNA
<213> ORGANISM: Artificial Sequence
<220> FEATURE:
<223> OTHER INFORMATION: sgRNA

<400> SEQUENCE: 16
cttcatgggg ccatagacct                                                     20

<210> SEQ ID NO 17
<211> LENGTH: 347
<212> TYPE: PRT
<213> ORGANISM: Artificial Sequence
<220> FEATURE:
<223> OTHER INFORMATION: VHH157 CAR

<400> SEQUENCE: 17

Met Ala Leu Pro Val Thr Ala Leu Leu Leu Pro Leu Ala Leu Leu Leu
1               5                   10                  15

His Ala Ala Arg Pro Gly Ser Ala Gln Ala Ala Gln Val Gln Leu
            20                  25                  30

Gln Glu Ser Gly Gly Gly Leu Val Gln Pro Gly Gly Ser Leu Ser Leu
        35                  40                  45

Ser Cys Thr Ala Ser Gly Phe Thr Phe Ser Ser Tyr Ser Met Ala Trp
    50                  55                  60

Val Arg Gln Ala Pro Gly Lys Gly Pro Glu Trp Val Ser Gly Ile Tyr
65                  70                  75                  80

Pro Ser Asp Gly Lys Thr Arg Tyr Ala Asp Phe Val Lys Gly Arg Phe
                85                  90                  95

Ser Ile Ser Arg Asp Asn Ala Lys Asn Met Leu Tyr Leu Gln Met Asn
            100                 105                 110

Asn Leu Glu Pro Glu Asp Thr Ala Leu Tyr Tyr Cys Ala Arg Gly Ile
        115                 120                 125

Thr Gly Leu Gly Pro Arg Gly Gln Gly Thr Gln Val Thr Val Ser Ser
    130                 135                 140

Ala Ala Ala Thr Ser Gly Gln Ala Gly Gln Ser Gly Glu Ser Lys Tyr
145                 150                 155                 160

Gly Pro Pro Cys Pro Pro Cys Pro Ala Ser Tyr Ile Trp Ala Pro Leu
                165                 170                 175

Ala Gly Thr Cys Gly Val Leu Leu Leu Ser Leu Val Ile Thr Leu Tyr
            180                 185                 190

Cys Lys Arg Gly Arg Lys Lys Leu Leu Tyr Ile Phe Lys Gln Pro Phe
        195                 200                 205

Met Arg Pro Val Gln Thr Thr Gln Glu Glu Asp Gly Cys Ser Cys Arg
    210                 215                 220

Phe Pro Glu Glu Glu Glu Gly Gly Cys Glu Leu Arg Val Lys Phe Ser
225                 230                 235                 240

Arg Ser Ala Asp Ala Pro Ala Tyr Lys Gln Gly Gln Asn Gln Leu Tyr
            245                 250                 255

Asn Glu Leu Asn Leu Gly Arg Arg Glu Glu Tyr Asp Val Leu Asp Lys
        260                 265                 270

Arg Arg Gly Arg Asp Pro Glu Met Gly Gly Lys Pro Arg Arg Lys Asn
    275                 280                 285

Pro Gln Glu Gly Leu Tyr Asn Glu Leu Gln Lys Asp Lys Met Ala Glu
290                 295                 300

Ala Tyr Ser Glu Ile Gly Met Lys Gly Glu Arg Arg Arg Gly Lys Gly
305                 310                 315                 320

His Asp Gly Leu Tyr Gln Gly Leu Ser Thr Ala Thr Lys Asp Thr Tyr
                325                 330                 335

Asp Ala Leu His Met Gln Ala Leu Pro Pro Arg
            340                 345

<210> SEQ ID NO 18
<211> LENGTH: 23
<212> TYPE: PRT
<213> ORGANISM: Artificial Sequence
<220> FEATURE:
<223> OTHER INFORMATION: signal peptide

<400> SEQUENCE: 18

Met Ala Leu Pro Val Thr Ala Leu Leu Leu Pro Leu Ala Leu Leu Leu
1               5                   10                  15

His Ala Ala Arg Pro Gly Ser
            20

<210> SEQ ID NO 19
<211> LENGTH: 123
<212> TYPE: PRT
<213> ORGANISM: Artificial Sequence
<220> FEATURE:
<223> OTHER INFORMATION: VHH157

<400> SEQUENCE: 19

Ala Ala Gln Ala Ala Gln Val Gln Leu Gln Glu Ser Gly Gly Gly Leu
1               5                   10                  15

Val Gln Pro Gly Gly Ser Leu Ser Leu Ser Cys Thr Ala Ser Gly Phe
            20                  25                  30

Thr Phe Ser Ser Tyr Ser Met Ala Trp Val Arg Gln Ala Pro Gly Lys
        35                  40                  45

Gly Pro Glu Trp Val Ser Gly Ile Tyr Pro Ser Asp Gly Lys Thr Arg
    50                  55                  60

Tyr Ala Asp Phe Val Lys Gly Arg Phe Ser Ile Ser Arg Asp Asn Ala
65                  70                  75                  80

Lys Asn Met Leu Tyr Leu Gln Met Asn Asn Leu Glu Pro Glu Asp Thr
                85                  90                  95

Ala Leu Tyr Tyr Cys Ala Arg Gly Ile Thr Gly Leu Gly Pro Arg Gly
            100                 105                 110

Gln Gly Thr Gln Val Thr Val Ser Ser Ala Ala
        115                 120

<210> SEQ ID NO 20
<211> LENGTH: 24
<212> TYPE: PRT
<213> ORGANISM: Artificial Sequence
<220> FEATURE:
<223> OTHER INFORMATION: IgG4mh

```
<400> SEQUENCE: 20

Ala Thr Ser Gly Gln Ala Gly Gln Ser Gly Glu Ser Lys Tyr Gly Pro
1               5                   10                  15

Pro Cys Pro Pro Cys Pro Ala Ser
            20

<210> SEQ ID NO 21
<211> LENGTH: 23
<212> TYPE: PRT
<213> ORGANISM: Artificial Sequence
<220> FEATURE:
<223> OTHER INFORMATION: CD8 transmembrane domain

<400> SEQUENCE: 21

Tyr Ile Trp Ala Pro Leu Ala Gly Thr Cys Gly Val Leu Leu Leu Ser
1               5                   10                  15

Leu Val Ile Thr Leu Tyr Cys
            20

<210> SEQ ID NO 22
<211> LENGTH: 154
<212> TYPE: PRT
<213> ORGANISM: Artificial Sequence
<220> FEATURE:
<223> OTHER INFORMATION: 4-1BB and CD3z

<400> SEQUENCE: 22

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Arg Val Lys Phe Ser Arg
        35                  40                  45

Ser Ala Asp Ala Pro Ala Tyr Lys Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly Arg Asp Pro Glu Met Gly Gly Lys Pro Arg Arg Lys Asn Pro
                85                  90                  95

Gln Glu Gly Leu Tyr Asn Glu Leu Gln Lys Asp Lys Met Ala Glu Ala
            100                 105                 110

Tyr Ser Glu Ile Gly Met Lys Gly Glu Arg Arg Arg Gly Lys Gly His
        115                 120                 125

Asp Gly Leu Tyr Gln Gly Leu Ser Thr Ala Thr Lys Asp Thr Tyr Asp
    130                 135                 140

Ala Leu His Met Gln Ala Leu Pro Pro Arg
145                 150

<210> SEQ ID NO 23
<211> LENGTH: 358
<212> TYPE: PRT
<213> ORGANISM: Artificial Sequence
<220> FEATURE:
<223> OTHER INFORMATION: VHH163 CAR

<400> SEQUENCE: 23

Met Ala Leu Pro Val Thr Ala Leu Leu Leu Pro Leu Ala Leu Leu Leu
1               5                   10                  15

His Ala Ala Arg Pro Gly Ser Ala Ala Gln Ala Ala Gln Val Gln Leu
            20                  25                  30
```

Gln Glu Ser Gly Gly Gly Leu Val Gln Pro Gly Gly Ser Leu Arg Leu
            35                  40                  45

Ser Cys Val Pro Ser Gly Phe Thr Phe Asp Gly Tyr Leu Ile Gly Trp
 50                  55                  60

Phe Arg Gln Ala Pro Gly Ser Glu Arg Lys Ala Val Ser Cys Ile Ser
 65                  70                  75                  80

Val Asn Gly Asp Arg Thr Asn Tyr Ala Asp Ser Val Lys Gly Arg Phe
                 85                  90                  95

Thr Ile Ser Arg Asp Asn Ala Lys Asn Thr Val Tyr Leu Gln Met Asn
                100                 105                 110

Ser Leu Arg Pro Asn Asp Thr Ala Ile Tyr Tyr Cys Ala Thr Arg Arg
            115                 120                 125

Gly Asn Arg Leu Tyr Asn Asn Asn Cys Pro Tyr Phe Glu Tyr Gly Thr
130                 135                 140

Trp Gly Gln Gly Thr Gln Val Thr Val Ser Ser Ala Ala Ala Thr Ser
145                 150                 155                 160

Gly Gln Ala Gly Gln Ser Gly Glu Ser Lys Tyr Gly Pro Pro Cys Pro
                165                 170                 175

Pro Cys Pro Ala Ser Tyr Ile Trp Ala Pro Leu Ala Gly Thr Cys Gly
            180                 185                 190

Val Leu Leu Leu Ser Leu Val Ile Thr Leu Tyr Cys Lys Arg Gly Arg
            195                 200                 205

Lys Lys Leu Leu Tyr Ile Phe Lys Gln Pro Phe Met Arg Pro Val Gln
            210                 215                 220

Thr Thr Gln Glu Glu Asp Gly Cys Ser Cys Arg Phe Pro Glu Glu Glu
225                 230                 235                 240

Glu Gly Gly Cys Glu Leu Arg Val Lys Phe Ser Arg Ser Ala Asp Ala
                245                 250                 255

Pro Ala Tyr Lys Gln Gly Gln Asn Gln Leu Tyr Asn Glu Leu Asn Leu
            260                 265                 270

Gly Arg Arg Glu Glu Tyr Asp Val Leu Asp Lys Arg Gly Arg Asp
            275                 280                 285

Pro Glu Met Gly Gly Lys Pro Arg Arg Lys Asn Pro Gln Glu Gly Leu
            290                 295                 300

Tyr Asn Glu Leu Gln Lys Asp Lys Met Ala Glu Ala Tyr Ser Glu Ile
305                 310                 315                 320

Gly Met Lys Gly Glu Arg Arg Arg Gly Lys Gly His Asp Gly Leu Tyr
                325                 330                 335

Gln Gly Leu Ser Thr Ala Thr Lys Asp Thr Tyr Asp Ala Leu His Met
            340                 345                 350

Gln Ala Leu Pro Pro Arg
            355

<210> SEQ ID NO 24
<211> LENGTH: 134
<212> TYPE: PRT
<213> ORGANISM: Artificial Sequence
<220> FEATURE:
<223> OTHER INFORMATION: VHH163

<400> SEQUENCE: 24

Ala Ala Gln Ala Ala Gln Val Gln Leu Gln Glu Ser Gly Gly Gly Leu
1               5                   10                  15

Val Gln Pro Gly Gly Ser Leu Arg Leu Ser Cys Val Pro Ser Gly Phe
            20                  25                  30

```
Thr Phe Asp Gly Tyr Leu Ile Gly Trp Phe Arg Gln Ala Pro Gly Ser
        35                  40                  45

Glu Arg Lys Ala Val Ser Cys Ile Ser Val Asn Gly Asp Arg Thr Asn
 50                  55                  60

Tyr Ala Asp Ser Val Lys Gly Arg Phe Thr Ile Ser Arg Asp Asn Ala
 65                  70                  75                  80

Lys Asn Thr Val Tyr Leu Gln Met Asn Ser Leu Arg Pro Asn Asp Thr
                85                  90                  95

Ala Ile Tyr Tyr Cys Ala Thr Arg Arg Gly Asn Arg Leu Tyr Asn Asn
            100                 105                 110

Asn Cys Pro Tyr Phe Glu Tyr Gly Thr Trp Gly Gln Gly Thr Gln Val
            115                 120                 125

Thr Val Ser Ser Ala Ala
        130
```

<210> SEQ ID NO 25
<211> LENGTH: 5
<212> TYPE: PRT
<213> ORGANISM: Artificial Sequence
<220> FEATURE:
<223> OTHER INFORMATION: VHH157 CAR CDR1

<400> SEQUENCE: 25

```
Ser Tyr Ser Met Ala
1               5
```

<210> SEQ ID NO 26
<211> LENGTH: 18
<212> TYPE: PRT
<213> ORGANISM: Artificial Sequence
<220> FEATURE:
<223> OTHER INFORMATION: VHH157 CAR CDR2

<400> SEQUENCE: 26

```
Gly Ile Tyr Pro Ser Asp Gly Lys Thr Arg Tyr Ala Asp Phe Val Lys
1               5                   10                  15

Gly Arg
```

<210> SEQ ID NO 27
<211> LENGTH: 9
<212> TYPE: PRT
<213> ORGANISM: Artificial Sequence
<220> FEATURE:
<223> OTHER INFORMATION: VHH157 CAR CDR3

<400> SEQUENCE: 27

```
Ala Arg Gly Ile Thr Gly Leu Gly Pro
1               5
```

<210> SEQ ID NO 28
<211> LENGTH: 5
<212> TYPE: PRT
<213> ORGANISM: Artificial Sequence
<220> FEATURE:
<223> OTHER INFORMATION: VHH163 CAR CDR1

<400> SEQUENCE: 28

```
Gly Tyr Leu Ile Gly
1               5
```

<210> SEQ ID NO 29
<211> LENGTH: 18

```
<212> TYPE: PRT
<213> ORGANISM: Artificial Sequence
<220> FEATURE:
<223> OTHER INFORMATION: VHH163 CAR CDR2

<400> SEQUENCE: 29

Cys Ile Ser Val Asn Gly Asp Arg Thr Asn Tyr Ala Asp Ser Val Lys
1               5                   10                  15

Gly Arg

<210> SEQ ID NO 30
<211> LENGTH: 20
<212> TYPE: PRT
<213> ORGANISM: Artificial Sequence
<220> FEATURE:
<223> OTHER INFORMATION: VHH163 CAR CDR3

<400> SEQUENCE: 30

Ala Thr Arg Arg Gly Asn Arg Leu Tyr Asn Asn Cys Pro Tyr Phe
1               5                   10                  15

Glu Tyr Gly Thr
            20

<210> SEQ ID NO 31
<211> LENGTH: 8721
<212> TYPE: DNA
<213> ORGANISM: Artificial Sequence
<220> FEATURE:
<223> OTHER INFORMATION: VHH157-BBz pLenti-CAR vector

<400> SEQUENCE: 31
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttccat agtaacgcca atagggactt      420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagaccctt tagtcagtgt ggaaaatctc tagcagtggc    1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
```

```
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ccgcgctga tcttcagacc tggaggagga     1560
gatatgaggg acaattggag aagtgaatta tataaatata aagtagtaaa aattgaacca    1620
ttaggagtag cacccaccaa ggcaaagaga agagtggtgc agagagaaaa aagagcagtg    1680
ggaataggag ctttgttcct tgggttcttg ggagcagcag gaagcactat gggcgcagcg    1740
tcaatgacgc tgacggtaca ggccagacaa ttattgtctg gtatagtgca gcagcagaac    1800
aatttgctga gggctattga ggcgcaacag catctgttgc aactcacagt ctggggcatc    1860
aagcagctcc aggcaagaat cctggctgtg gaaagatacc taaaggatca acagctcctg    1920
gggatttggg gttgctctgg aaaactcatt tgcaccactg ctgtgccttg gaatgctagt    1980
tggagtaata aatctctgga acagatttgg aatcacacga cctggatgga gtgggacaga    2040
gaaattaaca attacacaag cttaatacac tccttaattg aagaatcgca aaaccagcaa    2100
gaaaagaatg aacaagaatt attggaatta gataaatggg caagtttgtg gaattggttt    2160
aacataacaa attggctgtg gtatataaaa ttattcataa tgatagtagg aggcttggta    2220
ggtttaagaa tagttttgc tgtactttct atagtgaata gagttaggca gggatattca    2280
ccattatcgt ttcagaccca cctcccaacc ccgaggggac ccgacaggcc cgaaggaata    2340
gaagaagaag gtggagagag agacagagac agatccattc gattagtgaa cggatcggca    2400
ctgcgtgcgc caattctgca gacaaatggc agtattcatc cacaattta aaagaaaagg     2460 ggggattggg gggtacagtg caggggaaag aatagtagac ataatagcaa cagacataca    2520
aactaaagaa ttacaaaaac aaattacaaa aattcaaaat tttcgggttt attacaggga    2580
cagcagagat ccagtttggt tagtaccggg cccgctctag ccgtgaggct ccggtgcccg    2640
tcagtgggca gagcgcacat cgcccacagt ccccgagaag ttgggggag gggtcggcaa     2700 ttgaaccggt gcctagagaa ggtggcgcgg ggtaaactgg gaaagtgatg tcgtgtactg    2760
gctccgcctt tttcccgagg gtggggaga accgtatata agtgcagtag tcgccgtgaa    2820
cgttcttttt cgcaacgggt ttgccgcag aacacaggta agtgccgtgt gtggttcccg     2880
cgggcctggc ctctttacgg gttatggccc ttgcgtgcct tgaattactt ccacctggct    2940
gcagtacgtg attcttgatc ccgagcttcg ggttggaagt gggtgggaga gttcgaggcc    3000
ttgcgcttaa ggagcccctt cgcctcgtgc ttgagttgag gcctggcctg ggcgctgggg    3060
ccgccgcgtg cgaatctggt ggcaccttcg cgcctgtctc gctgctttcg ataagtctct    3120
agccatttaa aattttgat gacctgctgc gacgcttttt ttctggcaag atagtcttgt     3180
aaatgcgggc caagatctgc acactggtat tcggttttt ggggccgcgg gcggcgacgg     3240
ggcccgtgcg tcccagcgca catgttcggc gaggcgggc ctgcgagcgc ggccaccgag     3300
aatcggacgg gggtagtctc aagctggccg gcctgctctg gtgcctggcc tcgcgccgcc    3360
gtgtatcgcc ccgccctggg cggcaaggct ggccggtcg caccagttg cgtgagcgga     3420 aagatggccg cttccggcc ctgctgcagg gagctcaaaa tggaggacgc ggcgctcggg     3480
agagcgggcg ggtgagtcac ccacacaaag gaaagggcc tttccgtcct cagccgtcgc     3540
ttcatgtgac tccacggagt accgggcgcc gtccaggcac ctcgattagt tctcgagctt    3600
```

```
ttggagtacg tcgtctttag gttgggggga ggggttttat gcgatggagt ttccccacac    3660
tgagtgggtg gagactgaag ttaggccagc ttggcacttg atgtaattct ccttggaatt    3720
tgcccttttt gagtttggat cttggttcat tctcaagcct cagacagtgg ttcaaagttt    3780
ttttcttcca tttcaggtgt cgtgagcggc cgctgagtta actattctag aatggcctta    3840
ccagtgaccg ccttgctcct gccgctggcc ttgctgctcc acgccgccag gccgggatcc    3900
gcggcccagg cggcccaggt gcagctgcag gagtctgggg gaggcttggt gcagcctggg    3960
gggtctctga gcctctcctg tacagcctct ggattcacgt tcagtagtta ctccatggcc    4020
tgggtccgcc aggctccagg aagggaccc gaatgggtct cagggattta cccttctgat    4080
ggtaagacaa ggtatgcaga cttcgtgaag gccgattca gcatctccag agacaacgcc    4140
aagaatatgt tgtatctgca aatgaacaac ctggaacctg aggacacggc cctatattac    4200
tgtgcgagag gtatcaccgg attgggaccc cggggccagg ggacccaggt caccgtctcc    4260
tcagcggccg ccactagtgg ccaggccggc cagtccggag agagcaagta cggccctccc    4320
tgcccccctt gccctgctag ctacatctgg gcgcccttgg ccgggacttg tggggtcctt    4380
ctcctgtcac tggttatcac cctttactgc aaacggggca gaaagaaact cctgtatata    4440
ttcaaacaac catttatgag accagtacaa actactcaag aggaagatgg ctgtagctgc    4500
cgatttccag aagaagaaga aggaggatgt gaactgagag tgaagttcag caggagcgca    4560 gacgccccg cgtacaagca gggccagaac cagctctata cgagctcaa tctaggacga    4620 agagaggagt acgatgtttt ggacaagaga cgtggccggg accctgagat gggggggaaag    4680 ccgagaagga agaaccctca ggaaggcctg tacaatgaac tgcagaaaga taagatggcg    4740
gaggcctaca gtgagattgg gatgaaaggc gagcgccgga ggggcaaggg gcacgatggc    4800
ctttaccagg gtctcagtac agccaccaag gacacctacg acgcccttca catgcaggcc    4860
ctgccccctc gctaaagatc cgcccctctc cctcccccc cctaacgtt actggccgaa    4920 gccgcttgga ataaggccgg tgtgcgtttg tctatatgtt attttccacc atattgccgt    4980
cttttggcaa tgtgagggcc cggaaacctg gccctgtctt cttgacgagc attcctaggg    5040
gtctttcccc tctcgccaaa ggaatgcaag gtctgttgaa tgtcgtgaag gaagcagttc    5100
ctctggaagc ttcttgaaga caaacaacgt ctgtagcgac ccttt gcagg cagcggaacc    5160 ccccacctgg cgacaggtgc ctctgcggcc aaaagccacg tgtataagat acacctgcaa    5220
aggcggcaca accccagtgc cacgttgtga gttggatagt tgtggaaaga gtcaaatggc    5280
tctcctcaag cgtattcaac aaggggctga aggatgccca gaaggtaccc cattgtatgg    5340
gatctgatct ggggcctcgg tgcacatgct ttacatgtgt ttagtcgagg ttaaaaaaac    5400
gtctaggccc cccgaaccac ggggacgtgg ttttcctttg aaaaacacga tgataatatg    5460
gccacaacca tggtgagcaa gggcgaggag ctgttcaccg ggtggtgcc catcctggtc    5520 gagctggacg gcgacgtaaa cggccacaag ttcagcgtgt ccggcgaggg cgagggcgat    5580
gccacctacg gcaagctgac cctgaagttc atctgcacca ccggcaagct gcccgtgccc    5640
tggcccaccc tcgtgaccac cctgacctac ggcgtgcagt gcttcagccg ctaccccgac    5700
cacatgaagc agcacgactt cttcaagtcc gccatgcccg aaggctacgt ccaggagcgc    5760
accatcttct tcaaggacga cggcaactac aagacccgcg ccgaggtgaa gttcgagggc    5820
gacaccctgg tgaaccgcat cgagctgaag ggcatcgact tcaaggagga cggcaacatc    5880
ctggggcaca gctggagtac aactacaac agccacaacg tctatatcat ggccgacaag    5940
cagaagaacg gcatcaaggt gaacttcaag atccgccaca acatcgagga cggcagcgtg    6000
```

```
cagctcgccg accactacca gcagaacacc cccatcggcg acggcccgt gctgctgccc    6060
gacaaccact acctgagcac ccagtccgcc ctgagcaaag accccaacga gaagcgcgat    6120
cacatggtcc tgctggagtt cgtgaccgcc gccgggatca ctctcggcat ggacgagctg    6180
tacaagtaaa gcggccgcat cgataccgtc gacctcgatc gagacctaga aaacatgga    6240
gcaatcacaa gtagcaatac agcagctacc aatgctgatt gtgcctggct agaagcacaa    6300
gaggaggagg aggtgggttt tccagtcaca cctcaggtac ctttaagacc aatgacttac    6360
aaggcagctg tagatcttag ccactttta aaagaaaagg ggggactgga agggctaatt    6420
cactcccaac gaagacaaga tatccttgat ctgtggatct accacacaca aggctacttc    6480
cctgattggc agaactacac accagggcca gggatcagat atccactgac ctttggatgg    6540
tgctacaagc tagtaccagt tgagcaagag aaggtagaag aagccaatga aggagagaac    6600
acccgcttgt tacaccctgt gagcctgcat gggatggatg acccggagag agaagtatta    6660
gagtggaggt ttgacagccg cctagcattt catcacatgg cccgagagct gcatccggac    6720
tgtactgggt ctctctggtt agaccagatc tgagcctggg agctctctgg ctaactaggg    6780
aacccactgc ttaagcctca ataaagcttg ccttgagtgc ttcaagtagt gtgtgcccgt    6840
ctgttgtgtg actctggtaa ctagagatcc ctcagaccct tttagtcagt gtggaaaatc    6900
tctagcagca tgtgagcaaa aggccagcaa aaggccagga accgtaaaaa ggccgcgttg    6960
ctggcgtttt tccataggct ccgcccccct gacgagcatc acaaaaatcg acgctcaagt    7020
cagaggtggc gaaacccgac aggactataa agataccagg cgtttccccc tggaagctcc    7080
ctcgtgcgct ctcctgttcc gaccctgccg cttaccggat acctgtccgc ctttctccct    7140
tcgggaagcg tggcgctttc tcatagctca cgctgtaggt atctcagttc ggtgtaggtc    7200
gttcgctcca agctgggctg tgtgcacgaa ccccccgttc agcccgaccg ctgcgcctta    7260
tccggtaact atcgtcttga gtccaacccg gtaagcacg acttatcgcc actggcagca    7320
gccactggta acaggattag cagagcgagg tatgtaggcg gtgctacaga gttcttgaag    7380
tggtggccta actacggcta cactagaaga acagtatttg gtatctgcgc tctgctgaag    7440
ccagttacct tcggaaaaag agttggtagc tcttgatccg gcaaacaaac caccgctggt    7500
agcggtggtt tttttgtttg caagcagcag attacgcgca gaaaaaaagg atctcaagaa    7560
gatcctttga tcttttctac ggggtctgac gctcagtgga acgaaaactc acgttaaggg    7620
attttggtca tgagattatc aaaaaggatc ttcacctaga tccttttaaa ttaaaaatga    7680
agttttaaat caatctaaag tatatatgag taaacttggt ctgacagtta ccaatgctta    7740
atcagtgagg cacctatctc agcgatctgt ctatttcgtt catccatagt tgcctgactc    7800
cccgtcgtgt agataactac gatacgggag ggcttaccat ctggccccag tgctgcaatg    7860
ataccgcgag acccacgctc accggctcca gatttatcag caataaacca gccagccgga    7920
agggccgagc gcagaagtgg tcctgcaact ttatccgcct ccatccagtc tattaattgt    7980
tgccgggaag ctagagtaag tagttcgcca gttaatagtt tgcgcaacgt tgttgccatt    8040
gctacaggca tcgtggtgtc acgctcgtcg tttggtatgg cttcattcag ctccggttcc    8100
caacgatcaa ggcgagttac atgatccccc atgttgtgca aaaaagcggt tagctccttc    8160
ggtcctccga tcgttgtcag aagtaagttg gccgcagtgt tatcactcat ggttatggca    8220
gcactgcata attctcttac tgtcatgcca tccgtaagat gcttttctgt gactggtgag    8280
tactcaacca agtcattctg agaatagtgt atgcggcgac cgagttgctc ttgcccggcg    8340
```

| | | | | |
|---|---|---|---|---|
| tcaatacggg | ataataccgc | gccacatagc | agaactttaa | aagtgctcat cattggaaaa | 8400 |
| cgttcttcgg | ggcgaaaact | ctcaaggatc | ttaccgctgt | tgagatccag ttcgatgtaa | 8460 |
| cccactcgtg | cacccaactg | atcttcagca | tcttttactt | tcaccagcgt ttctgggtga | 8520 |
| gcaaaaacag | gaaggcaaaa | tgccgcaaaa | aagggaataa | gggcgacacg gaaatgttga | 8580 |
| atactcatac | tcttccttt | tcaatattat | tgaagcattt | atcagggtta ttgtctcatg | 8640 |
| agcggataca | tatttgaatg | tatttagaaa | aataaacaaa | tagggggttcc gcgcacattt | 8700 |
| ccccgaaaag | tgccacctga | c | | | 8721 |

<210> SEQ ID NO 32
<211> LENGTH: 8754
<212> TYPE: DNA
<213> ORGANISM: Artificial Sequence
<220> FEATURE:
<223> OTHER INFORMATION: VHH163-BBz pLenti-CAR vector

<400> SEQUENCE: 32

| | | | | | |
|---|---|---|---|---|---|
| gtcgacggat | cgggagatct | cccgatcccc | tatggtgcac | tctcagtaca atctgctctg | 60 |
| atgccgcata | gttaagccag | tatctgctcc | ctgcttgtgt | gttggaggtc gctgagtagt | 120 |
| gcgcgagcaa | aatttaagct | acaacaaggc | aaggcttgac | cgacaattgc atgaagaatc | 180 |
| tgcttagggt | taggcgtttt | gcgctgcttc | gcgatgtacg | ggccagatat acgcgttgac | 240 |
| attgattatt | gactagttat | taatagtaat | caattacggg | gtcattagtt catagcccat | 300 |
| atatggagtt | ccgcgttaca | taacttacgg | taaatggccc | gcctggctga ccgcccaacg | 360 |
| acccccgccc | attgacgtca | ataatgacgt | atgttcccat | agtaacgcca atagggactt | 420 |
| tccattgacg | tcaatgggtg | gagtatttac | ggtaaactgc | ccacttggca gtacatcaag | 480 |
| tgtatcatat | gccaagtacg | cccctattg | acgtcaatga | cggtaaatgg cccgcctggc | 540 |
| attatgccca | gtacatgacc | ttatgggact | ttcctacttg | gcagtacatc tacgtattag | 600 |
| tcatcgctat | taccatggtg | atgcggttt | ggcagtacat | caatgggcgt ggatagcggt | 660 |
| ttgactcacg | gggatttcca | agtctccacc | ccattgacgt | caatgggagt ttgttttggc | 720 |
| accaaaatca | acgggacttt | ccaaaatgtc | gtaacaactc | cgccccattg acgcaaatgg | 780 |
| gcggtaggcg | tgtacggtgg | gaggtctata | taagcagcgc | gttttgcctg tactgggtct | 840 |
| ctctggttag | accagatctg | agcctgggag | ctctctggct | aactagggaa cccactgctt | 900 |
| aagcctcaat | aaagcttgcc | ttgagtgctt | caagtagtgt | gtgcccgtct gttgtgtgac | 960 |
| tctggtaact | agagatccct | cagacccttt | tagtcagtgt | ggaaaatctc tagcagtggc | 1020 |
| gcccgaacag | ggacttgaaa | gcgaaaggga | aaccagagga | gctctctcga cgcaggactc | 1080 |
| ggcttgctga | agcgcgcacg | gcaagaggcg | aggggcggcg | actggtgagt acgccaaaaa | 1140 |
| ttttgactag | cggaggctag | aaggagagag | atgggtgcga | gagcgtcagt attaagcggg | 1200 |
| ggagaattag | atcgcgatgg | gaaaaaattc | ggttaaggcc | agggggaaag aaaaaatata | 1260 |
| aattaaaaca | tatagtatgg | gcaagcaggg | agctagaacg | attcgcagtt aatcctggcc | 1320 |
| tgttagaaac | atcagaaggc | tgtagacaaa | tactgggaca | gctacaacca tcccttcaga | 1380 |
| caggatcaga | agaacttaga | tcattatata | atacagtagc | aaccctctat tgtgtgcatc | 1440 |
| aaaggataga | gataaaagac | accaaggaag | ctttagacaa | gatagaggaa gagcaaaaca | 1500 |
| aaagtaagac | caccgcacag | caagcggccg | gccgcgctga | tcttcagacc tggaggagga | 1560 |
| gatatgaggg | acaattggag | aagtgaatta | tataaatata | aagtagtaaa aattgaacca | 1620 |
| ttaggagtag | cacccaccaa | ggcaaagaga | agagtggtgc | agagagaaaa aagagcagtg | 1680 |

```
ggaataggag ctttgttcct tgggttcttg ggagcagcag gaagcactat gggcgcagcg    1740
tcaatgacgc tgacggtaca ggccagacaa ttattgtctg gtatagtgca gcagcagaac    1800
aatttgctga gggctattga ggcgcaacag catctgttgc aactcacagt ctggggcatc    1860
aagcagctcc aggcaagaat cctgctgtg gaaagatacc taaaggatca acagctcctg     1920
gggatttggg gttgctctgg aaaactcatt tgcaccactg ctgtgccttg gaatgctagt    1980
tggagtaata atctctgga acagatttgg aatcacacga cctggatgga gtgggacaga    2040
gaaattaaca attacacaag cttaatacac tccttaattg aagaatcgca aaaccagcaa    2100
gaaaagaatg aacaagaatt attggaatta gataaatggg caagtttgtg gaattggttt    2160
aacataacaa attggctgtg gtatataaaa ttattcataa tgatagtagg aggcttggta    2220
ggtttaagaa tagttttttgc tgtactttct atagtgaata gagttaggca gggatattca    2280
ccattatcgt ttcagaccca cctcccaacc ccgaggggac ccgacaggcc cgaaggaata    2340
gaagaagaag tggagagag agacagagac agatccattc gattagtgaa cggatcggca    2400
ctgcgtgcgc caattctgca gacaaatggc agtattcatc cacaatttta aagaaaagg     2460 ggggattggg gggtacagtg caggggaaag aatagtagac ataatagcaa cagacataca    2520
aactaaagaa ttacaaaaac aaattacaaa aattcaaaat tttcgggttt attacaggga    2580
cagcagagat ccagtttggt tagtaccggg cccgctctag ccgtgaggct ccggtgcccg    2640
tcagtgggca gagcgcacat cgcccacagt ccccgagaag ttggggggag gggtcggcaa    2700
ttgaaccggt gcctagagaa ggtggcgcgg ggtaaactgg gaaagtgatg tcgtgtactg    2760
gctccgcctt tttcccgagg gtgggggaga accgtatata agtgcagtag tcgccgtgaa    2820 cgttctttttt cgcaacgggt ttgccgccag aacacaggta agtgccgtgt gtggttcccg    2880
cgggcctggc ctcttttacgg gttatggccc ttgcgtgcct tgaattactt ccacctggct    2940
gcagtacgtg attcttgatc ccgagcttcg ggttggaagt gggtgggaga gttcgaggcc    3000
ttgcgcttaa ggagccccctt cgcctcgtgc ttgagttgag gcctggcctg ggcgctgggg    3060
ccgccgcgtg cgaatctggt ggcaccttcg cgcctgtctc gctgctttcg ataagtctct    3120
agccatttaa aatttttgat gacctgctgc gacgcttttt ttctggcaag atagtcttgt    3180
aaatgcgggc caagatctgc acactggtat ttcggttttt ggggccgcgg gcggcgacgg    3240
ggcccgtgcg tcccagcgca catgttcggc gaggcgggc ctgcgagcgc ggccaccgag     3300
aatcggacgg gggtagtctc aagctggccg gcctgctctg gtgcctggcc tcgcgccgcc    3360
gtgtatcgcc ccgccctggg cggcaaggct ggcccggtcg gcaccagttg cgtgagcgga    3420
aagatggccg cttccggcc ctgctgcagg gagctcaaaa tggaggacgc ggcgctcggg      3480
agagcgggcg ggtgagtcac ccacacaaag gaaaagggcc tttccgtcct cagccgtcgc    3540
ttcatgtgac tccacggagt accgggcgcc gtccaggcac ctcgattagt tctcgagctt    3600
ttggagtacg tcgtctttag gttgggggga ggggttttat gcgatggagt ttccccacac    3660
tgagtgggtg gagactgaag ttaggccagc ttggcacttg atgtaattct ccttggaatt    3720
tgcccttttt gagtttggat cttggttcat tctcaagcct cagacagtgg ttcaaagttt    3780
ttttcttcca tttcaggtgt cgtgagcggc cgctgagtta actattctag aatgccttta    3840
ccagtgaccg ccttgctcct gccgctggcc ttgctgctcc acgccgccag gccgggatcc    3900
gcggcccagg cggcccaggt gcagctgcag gagtctggag gaggcttggt gcagcctggt    3960
gggtctctga gactctcctg tgtaccctct ggattcactt tcgatggtta tctcataggc    4020
```

```
tggttccgcc aggccccagg gagcgagcgg aaggcggtct catgtattag tgtgaatggt    4080
gatagaacaa actatgcaga ttccgtgaag ggccgattca ccatctccag agacaacgcc    4140
aagaacacgg tgtatctgca aatgaacagc ctgagaccta acgacacagc catttattac    4200
tgtgcgaccc gcaggggaaa tcgtctttat aataataact gcccatactt tgagtatggc    4260
acctggggcc aggggaccca ggtcaccgtc tcctcagcgg ccgccactag tggccaggcc    4320
ggccagtccg gagagagcaa gtacggcccc ccctgccccc cttgccctgc tagctacatc    4380
tgggcgccct tggccgggac ttgtggggtc cttctcctgt cactggttat caccctttac    4440
tgcaaacggg gcagaaagaa actcctgtat atattcaaac aaccatttat gagaccagta    4500
caaactactc aagaggaaga tggctgtagc tgccgatttc agaagaaga agaaggagga    4560 tgtgaactga gagtgaagtt cagcaggagc gcagacgccc ccgcgtacaa gcagggccag    4620
aaccagctct ataacgagct caatctagga cgaagagagg agtacgatgt tttggacaag    4680
agacgtggcc gggaccctga gatgggggga agccgagaa ggaagaaccc tcaggaaggc    4740
ctgtacaatg aactgcagaa agataagatg gcggaggcct acagtgagat tgggatgaaa    4800
ggcgagcgcc ggaggggcaa ggggcacgat ggcctttacc agggtctcag tacagccacc    4860
aaggacacct acgacgccct tcacatgcag gccctgcccc ctcgctaaag atccgcccct    4920
ctccctcccc ccccctaac gttactggcc gaagccgctt ggaataaggc cggtgtgcgt    4980
ttgtctatat gttattttcc accatattgc cgtcttttgg caatgtgagg gcccggaaac    5040
ctggccctgt cttcttgacg agcattccta ggggtctttc ccctctcgcc aaaggaatgc    5100
aaggtctgtt aatgtcgtg aaggaagcag ttcctctgga agcttcttga agacaaacaa    5160
cgtctgtagc gacccttgc aggcagcgga accccccacc tggcgacagg tgcctctgcg    5220
gccaaaagcc acgtgtataa gatacacctg caaaggcggc acaacccag tgccacgttg    5280 tgagttggat agttgtggaa agagtcaaat ggctctcctc aagcgtattc aacaaggggc    5340
tgaaggatgc ccagaaggta ccccattgta tgggatctga tctggggcct cggtgcacat    5400
gctttacatg tgtttagtcg aggttaaaaa aacgtctagg ccccccgaac cacggggacg    5460
tggttttcct ttgaaaaaca cgatgataat atggccacaa ccatggtgag caagggcgag    5520
gagctgttca ccggggtggt gcccatcctg gtcgagctgg acggcgacgt aaacggccac    5580
aagttcagcg tgtccggcga gggcgagggc gatgccacct acggcaagct gaccctgaag    5640
ttcatctgca ccaccggcaa gctgcccgtg cctggcccca ccctcgtgac caccctgacc    5700
tacggcgtgc agtgcttcag ccgctacccc gaccacatga gcagcacga cttcttcaag    5760 tccgccatgc ccgaaggcta cgtccaggag cgcaccatct tcttcaagga cgacggcaac    5820
tacaagaccc gcgccgaggt gaagttcgag ggcgacaccc tggtgaaccg catcgagctg    5880
aagggcatcg acttcaagga ggacggcaac atcctggggc acaagctgga gtacaactac    5940
aacagccaca acgtctatat catggccgac aagcagaaga acggcatcaa ggtgaacttc    6000
aagatccgcc acaacatcga ggacggcagc gtgcagctcg ccgaccacta ccagcagaac    6060
acccccatcg gcgacggccc cgtgctgctg cccgacaacc actacctgag cacccagtcc    6120
gccctgagca agacccccaa cgagaagcgc gatcacatgg tcctgctgga gttcgtgacc    6180
gccgccggga tcactctcgg catggacgag ctgtacaagt aaagcggccg catcgatacc    6240
gtcgacctcg atcgagacct agaaaaacat ggagcaatca caagtagcaa tacagcagct    6300
accaatgctg attgtgcctg gctagaagca caagaggagg aggaggtggg ttttccagtc    6360
acacctcagg tacctttaag accaatgact tacaaggcag ctgtagatct tagccacttt    6420
```

```
ttaaaagaaa agggggact ggaagggcta attcactccc aacgaagaca agatatcctt      6480
gatctgtgga tctaccacac acaaggctac ttccctgatt ggcagaacta cacaccaggg      6540
ccagggatca gatatccact gacctttgga tggtgctaca agctagtacc agttgagcaa      6600
gagaaggtag aagaagccaa tgaaggagag aacacccgct tgttacaccc tgtgagcctg      6660
catgggatgg atgacccgga gagagaagta ttagagtgga ggtttgacag ccgcctagca      6720
tttcatcaca tggcccgaga gctgcatccg gactgtactg ggtctctctg gttagaccag      6780
atctgagcct gggagctctc tggctaacta gggaacccac tgcttaagcc tcaataaagc      6840
ttgccttgag tgcttcaagt agtgtgtgcc cgtctgttgt gtgactctgg taactagaga      6900
tccctcagac ccttttagtc agtgtggaaa atctctagca gcatgtgagc aaaaggccag      6960
caaaaggcca ggaaccgtaa aaaggccgcg ttgctggcgt ttttccatag gctccgcccc      7020
cctgacgagc atcacaaaaa tcgacgctca agtcagaggt ggcgaaaccc gacaggacta      7080
taaagatacc aggcgtttcc ccctggaagc tccctcgtgc gctctcctgt tccgaccctg      7140
ccgcttaccg gatacctgtc cgcctttctc ccttcgggaa gcgtggcgct ttctcatagc      7200
tcacgctgta ggtatctcag ttcggtgtag gtcgttcgct ccaagctggg ctgtgtgcac      7260
gaaccccccg ttcagcccga ccgctgcgcc ttatccggta actatcgtct tgagtccaac      7320
ccggtaagac acgacttatc gccactggca gcagccactg gtaacaggat tagcagagcg      7380
aggtatgtag gcggtgctac agagttcttg aagtggtggc ctaactacgg ctacactaga      7440
agaacagtat ttggtatctg cgctctgctg aagccagtta ccttcggaaa aagagttggt      7500
agctcttgat ccggcaaaca aaccaccgct ggtagcggtg gtttttttgt ttgcaagcag      7560
cagattacgc gcagaaaaaa aggatctcaa gaagatcctt tgatcttttc tacgggtct      7620 gacgctcagt ggaacgaaaa ctcacgttaa gggattttgg tcatgagatt atcaaaaagg      7680
atcttcacct agatcctttt aaattaaaaa tgaagtttta atcaatcta aagtatatat       7740 gagtaaactt ggtctgacag ttaccaatgc ttaatcagtg aggcacctat ctcagcgatc      7800
tgtctatttc gttcatccat agttgcctga ctccccgtcg tgtagataac tacgatacgg      7860
gagggcttac catctggccc cagtgctgca atgataccgc gagacccacg ctcaccggct      7920
ccagatttat cagcaataaa ccagccagcc ggaagggccg agcgcagaag tggtcctgca      7980
actttatccg cctccatcca gtctattaat tgttgccggg aagctagagt aagtagttcg      8040
ccagttaata gtttgcgcaa cgttgttgcc attgctacag gcatcgtggt gtcacgctcg      8100
tcgtttggta tggcttcatt cagctccggt tcccaacgat caaggcgagt tacatgatcc      8160
cccatgttgt gcaaaaaagc ggttagctcc ttcggtcctc cgatcgttgt cagaagtaag      8220
ttggccgcag tgttatcact catggttatg gcagcactgc ataattctct tactgtcatg      8280
ccatccgtaa gatgcttttc tgtgactggt gagtactcaa ccaagtcatt ctgagaatag      8340
tgtatgcggc gaccgagttg ctcttgcccg gcgtcaatac gggataatac cgcgccacat      8400
agcagaactt taaaagtgct catcattgga aaacgttctt cggggcgaaa actctcaagg      8460
atcttaccgc tgttgagatc cagttcgatg taacccactc gtgcacccaa ctgatcttca      8520
gcatctttta ctttcaccag cgtttctggg tgagcaaaaa caggaaggca aaatgccgca      8580
aaaaagggaa taagggcgac acggaaatgt tgaatactca tactcttcct ttttcaatat      8640
tattgaagca tttatcaggg ttattgtctc atgagcggat acatatttga atgtatttag      8700
aaaaataaac aaataggggt tccgcgcaca tttccccgaa aagtgccacc tgac            8754
```

<210> SEQ ID NO 33
<211> LENGTH: 1047
<212> TYPE: DNA
<213> ORGANISM: Artificial Sequence
<220> FEATURE:
<223> OTHER INFORMATION: VHH1-BBz CAR

<400> SEQUENCE: 33

```
atggccttac cagtgaccgc cttgctcctg ccgctggcct tgctgctcca cgccgccagg      60
ccgggatccg cggcccaggc ggcccaggtg cagctgcagg agtctggggg aggattggtg     120
cagcctgggg gctcgacaag actctcctgt gtatcgtccc gcacctttag ttattatgac     180
atgggctggt tccgccaggc tccagggaag gagcgtgagt tcgtagcact gcttagttgg     240
aatgggaaa atgcagagta ttcagactcc gtgatgggcc gtttcaccgt ctcccgaggg     300
aataccccaga attcggtgaa tctgcaaatg aacaacctga acctgaggga cacgggcatc     360
tattactgcg cagtgacgca cggtggagcg cggtcggttc gttcctgggg ccaggggacc     420
caggtcaccg tctcctcagc ggccgccact agtggccagg ccggccagtc cggagagtct     480
aagtacggcc ctcccctgccc tccttgccca gctagctaca tctgggcgcc cttggccggg     540
acttgtgggg tccttctcct gtcactggtt atcacccttt actgcaaacg gggcagaaag     600
aaactcctgt atatattcaa acaaccattt atgagaccag tacaaactac tcaagaggaa     660
gatggctgta gctgccgatt tccagaagaa gaagaaggag gatgtgaact gagagtgaag     720
ttcagcagga gcgcagacgc ccccgcgtac aagcagggcc agaaccagct ctataacgag     780
ctcaatctag gacgaagaga ggagtacgat gttttggaca gagacgtgg ccgggaccct     840
gagatggggg gaaagccgag aaggaagaac cctcaggaag gcctgtacaa tgaactgcag     900
aaagataaga tggcggaggc ctacagtgag attgggatga aggcgagcg ccggagggc     960
aaggggcacg atggccttta ccagggtctc agtacagcca ccaaggacac ctacgacgcc     1020
cttcacatgc aggccctgcc ccctcgc                                         1047
```

<210> SEQ ID NO 34
<211> LENGTH: 349
<212> TYPE: PRT
<213> ORGANISM: Artificial Sequence
<220> FEATURE:
<223> OTHER INFORMATION: VHH1-BBz CAR

<400> SEQUENCE: 34

```
Met Ala Leu Pro Val Thr Ala Leu Leu Leu Pro Leu Ala Leu Leu Leu
1               5                   10                  15

His Ala Ala Arg Pro Gly Ser Ala Ala Gln Ala Gln Val Gln Leu
            20                  25                  30

Gln Glu Ser Gly Gly Gly Leu Val Gln Pro Gly Gly Ser Thr Arg Leu
        35                  40                  45

Ser Cys Val Ser Ser Arg Thr Phe Ser Tyr Tyr Asp Met Gly Trp Phe
    50                  55                  60

Arg Gln Ala Pro Gly Lys Glu Arg Glu Phe Val Ala Leu Leu Ser Trp
65                  70                  75                  80

Asn Gly Glu Asn Ala Glu Tyr Ser Asp Ser Val Met Gly Arg Phe Thr
                85                  90                  95

Val Ser Arg Gly Asn Thr Gln Asn Ser Val Asn Leu Gln Met Asn Asn
            100                 105                 110

Leu Lys Pro Glu Asp Thr Gly Ile Tyr Tyr Cys Ala Val Thr His Gly
        115                 120                 125
```

Gly Ala Arg Ser Val Arg Ser Trp Gly Gln Gly Thr Gln Val Thr Val
            130                 135                 140

Ser Ser Ala Ala Ala Thr Ser Gly Gln Ala Gly Gln Ser Gly Glu Ser
145                 150                 155                 160

Lys Tyr Gly Pro Pro Cys Pro Pro Cys Pro Ala Ser Tyr Ile Trp Ala
                165                 170                 175

Pro Leu Ala Gly Thr Cys Gly Val Leu Leu Leu Ser Leu Val Ile Thr
            180                 185                 190

Leu Tyr Cys Lys Arg Gly Arg Lys Lys Leu Leu Tyr Ile Phe Lys Gln
        195                 200                 205

Pro Phe Met Arg Pro Val Gln Thr Thr Gln Glu Glu Asp Gly Cys Ser
    210                 215                 220

Cys Arg Phe Pro Glu Glu Glu Glu Gly Gly Cys Glu Leu Arg Val Lys
225                 230                 235                 240

Phe Ser Arg Ser Ala Asp Ala Pro Ala Tyr Lys Gln Gly Gln Asn Gln
                245                 250                 255

Leu Tyr Asn Glu Leu Asn Leu Gly Arg Arg Glu Glu Tyr Asp Val Leu
            260                 265                 270

Asp Lys Arg Arg Gly Arg Asp Pro Glu Met Gly Gly Lys Pro Arg Arg
        275                 280                 285

Lys Asn Pro Gln Glu Gly Leu Tyr Asn Glu Leu Gln Lys Asp Lys Met
    290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg
            340                 345

<210> SEQ ID NO 35
<211> LENGTH: 1173
<212> TYPE: DNA
<213> ORGANISM: Artificial Sequence
<220> FEATURE:
<223> OTHER INFORMATION: VHH1-28BBz CAR

<400> SEQUENCE: 35 atggcttac cagtgaccgc cttgctcctg ccgctggcct tgctgctcca cgccgccagg    60
ccgggatccg cggcccaggc ggcccaggtg cagctgcagg agtctggggg aggattggtg   120
cagcctgggg gctcgacaag actctcctgt gtatcgtccc gcacctttag ttattatgac   180
atgggctggt tccgccaggc tccagggaag gagcgtgagt tcgtagcact gcttagttgg   240 aatgggaaa atgcagagta ttcagactcc gtgatgggcc gtttcaccgt ctcccgaggg   300
aatacccaga attcggtgaa tctgcaaatg aacaacctga acctgagga cacgggcatc   360 tattactgcg cagtgacgca cggtggagcg cggtcggttc gttcctgggg ccaggggacc   420
caggtcaccg tctcctcagc ggccgccact agttccggag agagcaagta cggccctccc   480 tgccccctt gcctgatat cttttggtg ctggtggtgg ttggtggagt cctggcttgc   540
tatagcttgc tagtaacagt ggcctttatt attttctggg tgaggagtaa gaggagcagg   600
ctcctgcaca gtgactacat gaacatgact cccgccgcc ccgggcccac cgcaagcat   660 taccagccct atgccccacc acgcgacttc gcagcctatc gctccgctag caaacggggc   720
agaaagaaac tcctgtatat attcaaacaa ccatttatga ccagtaca aactactcaa   780

```
gaggaagatg gctgtagctg ccgatttcca gaagaagaag aaggaggatg tgaactgaga    840
gtgaagttca gcaggagcgc agacgccccc gcgtacaagc agggccagaa ccagctctat    900
aacgagctca atctaggacg aagagaggag tacgatgttt tggacaagag acgtggccgg    960
gaccctgaga tgggggaaa gccgagaagg aagaaccctc aggaaggcct gtacaatgaa   1020
ctgcagaaag ataagatggc ggaggcctac agtgagattg ggatgaaagg cgagcgccgg   1080
aggggcaagg ggcacgatgg cctttaccag ggtctcagta cagccaccaa ggacacctac   1140
gacgcccttc acatgcaggc cctgccccct cgc                                1173
```

<210> SEQ ID NO 36
<211> LENGTH: 391
<212> TYPE: PRT
<213> ORGANISM: Artificial Sequence
<220> FEATURE:
<223> OTHER INFORMATION: VHH1-28BBz CAR

<400> SEQUENCE: 36

```
Met Ala Leu Pro Val Thr Ala Leu Leu Leu Pro Leu Ala Leu Leu Leu
1               5                   10                  15

His Ala Ala Arg Pro Gly Ser Ala Ala Gln Ala Ala Gln Val Gln Leu
            20                  25                  30

Gln Glu Ser Gly Gly Gly Leu Val Gln Pro Gly Gly Ser Thr Arg Leu
        35                  40                  45

Ser Cys Val Ser Ser Arg Thr Phe Ser Tyr Tyr Asp Met Gly Trp Phe
    50                  55                  60

Arg Gln Ala Pro Gly Lys Glu Arg Glu Phe Val Ala Leu Leu Ser Trp
65                  70                  75                  80

Asn Gly Glu Asn Ala Glu Tyr Ser Asp Ser Val Met Gly Arg Phe Thr
                85                  90                  95

Val Ser Arg Gly Asn Thr Gln Asn Ser Val Asn Leu Gln Met Asn Asn
            100                 105                 110

Leu Lys Pro Glu Asp Thr Gly Ile Tyr Tyr Cys Ala Val Thr His Gly
        115                 120                 125

Gly Ala Arg Ser Val Arg Ser Trp Gly Gln Gly Thr Gln Val Thr Val
    130                 135                 140

Ser Ser Ala Ala Ala Thr Ser Ser Gly Glu Ser Lys Tyr Gly Pro Pro
145                 150                 155                 160

Cys Pro Pro Cys Pro Asp Ile Phe Trp Val Leu Val Val Val Gly Gly
                165                 170                 175

Val Leu Ala Cys Tyr Ser Leu Leu Val Thr Val Ala Phe Ile Ile Phe
            180                 185                 190

Trp Val Arg Ser Lys Arg Ser Arg Leu Leu His Ser Asp Tyr Met Asn
        195                 200                 205

Met Thr Pro Arg Arg Pro Gly Pro Thr Arg Lys His Tyr Gln Pro Tyr
    210                 215                 220

Ala Pro Pro Arg Asp Phe Ala Ala Tyr Arg Ser Ala Ser Lys Arg Gly
225                 230                 235                 240

Arg Lys Lys Leu Leu Tyr Ile Phe Lys Gln Pro Phe Met Arg Pro Val
                245                 250                 255
```

```
Gln Thr Thr Gln Glu Glu Asp Gly Cys Ser Cys Arg Phe Pro Glu Glu
            260                 265                 270

Glu Glu Gly Gly Cys Glu Leu Arg Val Lys Phe Ser Arg Ser Ala Asp
        275                 280                 285

Ala Pro Ala Tyr Lys Gln Gly Gln Asn Gln Leu Tyr Asn Glu Leu Asn
    290                 295                 300

Leu Gly Arg Arg Glu Glu Tyr Asp Val Leu Asp Lys Arg Arg Gly Arg
305                 310                 315                 320

Asp Pro Glu Met Gly Gly Lys Pro Arg Arg Lys Asn Pro Gln Glu Gly
                325                 330                 335

Leu Tyr Asn Glu Leu Gln Lys Asp Lys Met Ala Glu Ala Tyr Ser Glu
            340                 345                 350

Ile Gly Met Lys Gly Glu Arg Arg Arg Gly Lys Gly His Asp Gly Leu
        355                 360                 365

Tyr Gln Gly Leu Ser Thr Ala Thr Lys Asp Thr Tyr Asp Ala Leu His
    370                 375                 380

Met Gln Ala Leu Pro Pro Arg
385                 390

<210> SEQ ID NO 37
<211> LENGTH: 68
<212> TYPE: PRT
<213> ORGANISM: Artificial sequence
<220> FEATURE:
<223> OTHER INFORMATION: CD28 transmembrane and CD28 intracellular
      domain

<400> SEQUENCE: 37

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 38
<211> LENGTH: 17
<212> TYPE: PRT
<213> ORGANISM: Artificial Sequence
<220> FEATURE:
<223> OTHER INFORMATION: modified IgG4h

<400> SEQUENCE: 38

Ala Thr Ser Ser Gly Glu Ser Lys Tyr Gly Pro Pro Cys Pro Pro Cys
1               5                   10                  15

Pro
```